United States Patent

Nakai et al.

Patent Number: 4,689,327
Date of Patent: Aug. 25, 1987

[54] N-SUBSTITUTED-2-[2-[2-(4-PHENYLPIPER-AZINE-1-YL)ETHOXY]PHENYL]-THIAZOLIDINE-3-CARBOXAMIDES USEFUL AS CARDIOTONIC AGENT

[75] Inventors: Hideo Nakai; Hiroshi Wada, both of Omiya; Taku Nagao, Meguro; Hideo Yabana, Omiya, all of Japan

[73] Assignee: Tanabe Seiyaku Co., Ltd., Osaka, Japan

[21] Appl. No.: 748,394

[22] Filed: Jun. 24, 1985

[30] Foreign Application Priority Data

Jun. 30, 1984 [GB] United Kingdom ............... 8416720
Jan. 10, 1985 [GB] United Kingdom ............... 8500576
Mar. 16, 1985 [GB] United Kingdom ............... 8506888

[51] Int. Cl.$^4$ ................ A61K 31/495; C07D 417/10
[52] U.S. Cl. .................................. 514/252; 544/337; 544/369
[58] Field of Search ................ 544/369, 337; 514/252

[56] References Cited

FOREIGN PATENT DOCUMENTS 212174 12/1982 Japan.
41872 3/1983 Japan.

Primary Examiner—Donald G. Daus
Assistant Examiner—C. Shen
Attorney, Agent, or Firm—Birch, Stewart, Kolasch & Birch

[57] ABSTRACT

A novel thiazolidine derivative of the formula:

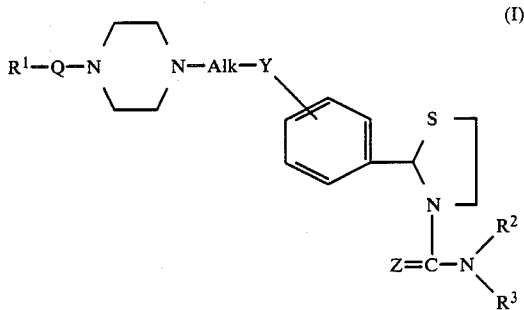

wherein $R^1$ is a substituted or unsubstituted phenyl group, Q is a single bond, a lower alkylene group or a lower alkenylene group, $R^2$ and $R^3$ are the same or different and each is hydrogen atom, a lower alkyl group, a cycloalkyl group, a lower alkanoyl group, a lower alkoxycarbonyl group, a lower alkylsulfonyl group, a benzoyl group, a phenyl group or a di(lower alkyl)phosphoryl group, Alk is a lower alkylene group, and Y and Z are the same or different and each is oxygen atom or sulfur atom, or a pharmaceutically acceptable salt thereof, which is useful as a cardiotonic agent is disclosed together with processes for the preparation of the compound and a pharmaceutical composition containing said compound.

18 Claims, No Drawings

N-SUBSTITUTED-2-[2-[2-(4-PHENYLPIPERAZINE-1-YL)ETHOXY]PHENYL]-THIAZOLIDINE-3-CARBOXAMIDES USEFUL AS CARDIOTONIC AGENT

This invention relates to a novel thiazolidine derivative, a salt thereof, processes for preparing the same, and a pharmaceutical composition containing said compound as an active ingredient. More particularly, it relates to a novel thiazolidine derivative of the formula:

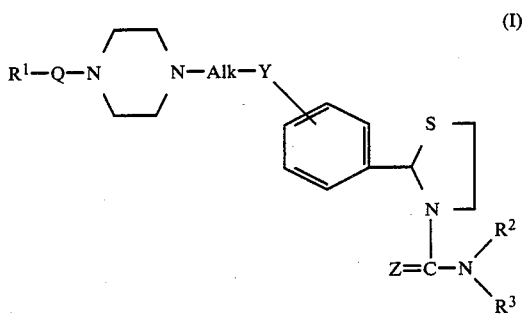

wherein $R^1$ is a substituted or unsubstituted phenyl group, Q is a single bond, a lower alkylene group or a lower alkenylene group, $R^2$ and $R^3$ are the same or different and each is a hydrogen atom, a lower alkyl group, a cycloalkyl group, a lower alkanoyl group, a lower alkoxycarbonyl group, a lower alkylsulfonyl group, a benzoyl group, a phenyl group or a di(-loweralkyl)phosphoryl group, Alk is a lower alkylene group, and Y and Z are the same or different and each is oxygen atom or sulfur atom, or a pharmaceutically acceptable salt thereof.

In the present specification, the term "lower alkyl" denotes a straight or branched alkyl having 1 to 5 carbon atoms, the term "cycloalkyl" denotes a cycloalkyl having 3 to 7 carbon atoms, and the term "lower alkylene" denotes a straight or branched alkylene having 1 to 5 carbon atoms. The term "lower alkenylene" denotes a straight or branched alkenylene having 2 to 6 carbon atoms, "lower alkanoyl" denotes a straight or branched alkanoyl having 2 to 6 carbon atoms, and the term "lower alkanoic acid" denotes a straight or branched alkanoic acid having 2 to 6 carbon atoms. The term "lower alkoxy" denotes a straight or branched alkoxy having 1 to 5 carbon atoms and the term "lower alkoxycarbonyl" denotes a straight or branched alkoxycarbonyl having 2 to 6 carbon atoms.

The compound (I) of the present invention and a salt thereof are novel and useful as cardiotonic agents. For example, (−)-N-methyl-2-{2-[2-(4-phenylpiperazin-1-yl)ethyloxy]phenyl}thiazolidine-3-carboxamide oxalate when administered intravenously to dogs at a dose of 0.003 mg/kg shows approximately 36% increase in left ventricular contractility, and said cardiotonic effect of the compound of the present invention lasts for about 40 minutes. Moreover, when examined by the use of isolated heart of guinea pig (Langendorff's method), (+) or (±)-N-methyl-2-{2-[2-(4-phenylpiperazin-1-yl)ethyloxy]phenyl}thiazolidine-3-carboxamide oxalate at a dose of 3 μg shows an increase in cardiac contractile force.

Examples of the compounds of the present invention are those of the formula (I) in which $R^1$ is phenyl which is unsubstituted or substituted with at least one substituent selected from the group consisting of a halogen atom (e.g., fluorine, chlorine or bromime), a lower alkyl (e.g., methyl, ethyl, propyl, butyl or pentyl), a lower alkylthio (e.g., methylthio, ethylthio, propylthio, butylthio or pentylthio), a lower alkoxy (e.g., methoxy, ethoxy, propoxy, butoxy or pentyloxy) and nitro; the group Q is a single bond, a lower alkylene (e.g., methylene, ethylene, trimethylene, tetramethylene or pentamethylene) or a lower alkenylene (e.g., vinylene, propenylene, butenylene or pentenylene); Alk is a lower alkylene (e.g., methylene, ethylene, trimethylene, tetramethylene or pentamethylene); $R^2$ and $R^3$ are the same or different and each is hydrogen atom, a lower alkyl (e.g., methyl, ethyl, propyl, butyl or pentyl), a cycloalkyl (e.g., cyclopropyl, cyclobutyl, cyclopentyl, cyclohexyl or cycloheptyl), a lower alkanoyl (e.g., acetyl, propionyl, butyryl, valeryl or hexanoyl), a lower alkoxycarbonyl (e.g., methoxycarbonyl, ethoxycarbonyl, propoxycarbonyl, butoxycarbonyl or pentyloxycarbonyl), a lower alkylsulfonyl (e.g., methylsulfonyl, ethylsulfonyl, propylsulfonyl, butylsulfonyl or pentylsulfonyl), benzoyl, phenyl or a di(lower alkyl)phosphoryl (e.g., dimethylphosphoryl, diethylphosphoryl, dipropylphosphoryl, dibutylphosphoryl or dipentylphosphoryl); and Y and Z are the same or different and each is oxygen atom or sulfur atom. Preferred compounds are the compounds of the formula (I) in which $R^1$ is phenyl which is unsubstituted or substituted with at least one substituent selected from the group consisting of halogen atom, lower alkyl, lower alkylthio, lower alkoxy and nitro; the group Q is a single bond, lower alkylene or lower alkenylene; Alk is lower alkylene; $R^2$ is hydrogen atom, lower alkyl, cycloalkyl, lower alkanoyl, lower alkoxycarbonyl, lower alkylsulfonyl, benzoyl, phenyl or di(lower alkyl)phosphoryl and $R^3$ is hydrogen atom or lower alkyl; or $R^2$ is lower alkyl and $R^3$ is lower alkanoyl or benzoyl; and Y and Z are the same or different and each is oxygen atom or sulfur atom. Other preferred compounds are those of the formula (I) in which $R^1$ is phenyl which is unsubstituted or substituted with at least one substituent selected from the group consisting of fluorine, chlorine, alkyl having one to 3 carbon atoms, alkoxy having one to 3 carbon atoms, alkylthio having one to 3 carbon atoms and nitro; Q is a single bond, alkylene having one to 3 carbon atoms or propenylene (—CH=CH—CH$_2$—), Alk is alkylene having 2 to 5 carbon atoms; $R^2$ is hydrogen atom, alkyl having one to 4 carbon atoms, cycloalkyl having 4 to 6 carbon atoms, alkanoyl having 2 to 5 carbon atoms, alkoxycarbonyl having 2 to 4 carbon atoms, benzoyl, phenyl or di(alkyl)phosphoryl having 2 to 6 carbon atoms and $R^3$ is hydrogen atom or alkyl having one to 4 carbon atoms; or $R^2$ is alkyl having one to 4 carbon atoms and $R^3$ is alkanoyl having 2 to 5 carbon atoms or benzoyl; and Y and Z are the same or different and each is an oxygen atom or sulfur atom.

Other preferred compounds are those of the formula (I) in which $R^1$ is phenyl, fluorophenyl or methylphenyl, Q is a single bond, Alk is ethylene, $R^2$ is hydrogen atom or methyl, $R^3$ is hydrogen atom, methyl or acetyl and Y and Z are the same or different and each is oxygen atom or sulfur atom. In the formula (I) it is preferred that, when the carbon atom of the benzene ring which carries a thiazolidine group is taken as the 1-position, the substituent:

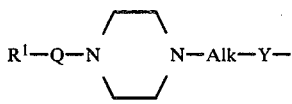

is substituted at the 2- or 4-position of said benzene ring. Still other preferred compounds are those of the formula:

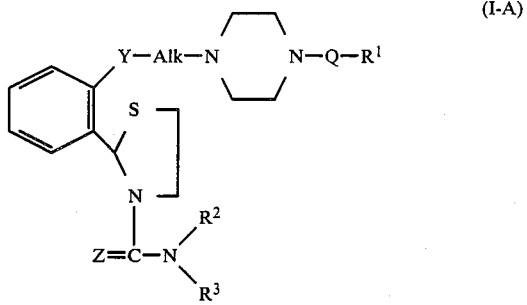

wherein $R^1$ is a substituted or unsubstituted phenyl group, Q is a single bond, a lower alkylene group or a lower alkenylene group, $R^2$ and $R^3$ are the same or different and each is hydrogen atom, a lower alkyl group, a cycloalkyl group, a lower alkanoyl group, a lower alkoxycarbonyl group, a lower alkylsulfonyl group, a benzoyl group, a phenyl group or di(lower alkyl)phosphoryl group, Alk is a lower alkylene group, and Y and Z are the same or different and each is oxygen atom or sulfur atom. Further preferred compounds are those of the formula (I-A) in which $R^1$ is phenyl which is unsubstituted or substituted with at least one substituent selected from the group consisting of chlorine, fluorine, alkyl having one to 3 carbon atoms, alkoxy having one to 3 carbon atoms, alkylthio having one to 3 carbon atoms and nitro; Q is a single bond, alkylene having one to 3 carbon atoms or propenylene; Alk is alkylene having 2 to 5 carbon atoms; $R^2$ is hydrogen atom, alkyl having one to 4 carbon atoms, cycloalkyl having 4 to 6 carbon atoms, alkanoyl having 2 to 5 carbon atoms, alkoxycarbonyl having 2 to 4 carbon atoms, benzoyl, phenyl or di(alkyl)phosphoryl having 2 to 6 carbon atoms and $R^3$ is hydrogen atom or alkyl having one to 4 carbon atoms; or $R^2$ is alkyl having one to 4 carbon atoms and $R^3$ is alkanoyl having 2 to 5 carbon atoms or benzoyl; and Y and Z are the same or different and each is oxygen atom or sulfur atom. Still further preferred compounds are those of the formula (I-A) in which $R^1$ is phenyl, fluorophenyl, chlorophenyl, methylphenyl or methoxyphenyl; Q is a single bond; Alk is ethylene or trimethylene; $R^2$ is hydrogen atom or alkyl having one to 3 carbon atoms, $R^3$ is hydrogen atom, alkyl having one to 3 carbon atoms or alkanoyl having 2 to 4 carbon atoms, and Y and Z are the same or different and each is oxygen atom or sulfur atom. Other preferred compounds are those of the formula (I-A) in which $R^1$ is phenyl, fluorophenyl or methylphenyl, Q is a single bond, Alk is ethylene, $R^2$ is hydrogen atom or methyl, $R^3$ is hydrogen atom, methyl or acetyl and Y and Z are the same or different and each is oxygen atom or sulfur atom. Still other preferred compounds are those of the formula (I-A) in which $R^1$ is phenyl, fluorophenyl or methylphenyl, Q is a single bond, Alk is ethylene, $R^2$ is hydrogen atom or methyl, $R^3$ is hydrogen atom, methyl or acetyl, Y is oxygen atom and Z is oxygen atom or sulfur atom. Most preferred compounds are those of the formula (I-A) in which $R^1$ is phenyl or fluorophenyl, Q is a single bond, Alk is ethylene, $R^2$ is methyl, $R^3$ is hydrogen atom or acetyl and Y and Z are oxygen atom.

The compound of the formula (I) has an asymmetric carbon at the 2-position of the thiazolidine ring and can exist in the form of two optical isomers. The present invention includes within its scope either one of these isomers and a racemic modification thereof.

The compound (I) of the present invention can be prepared, for example, by the step or steps of:

[Process (A)] reacting a thiazolidine derivative of the formula:

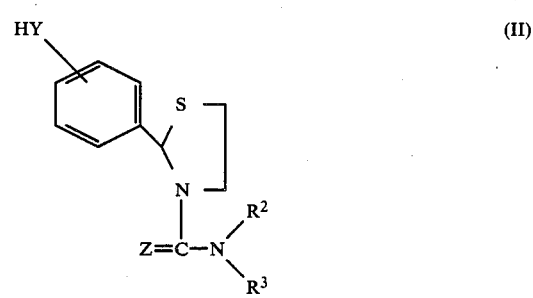

wherein $R^2$, $R^3$, Y and Z are the same as defined above, or a salt thereof with a piperazine derivative of the formula:

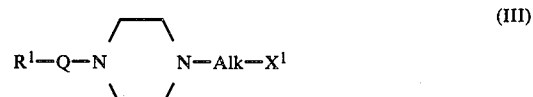

wherein $X^1$ is a reactive residue and $R^1$, Q and Alk are the same as defined above, or a salt thereof; or

[Process (B)] reacting a thiazolidine derivative of the formula:

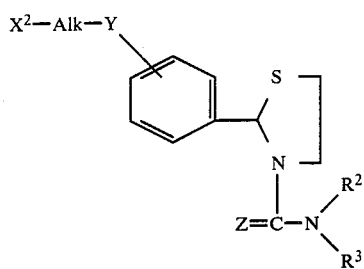
(IV)

wherein $X^2$ is a reactive residue and Alk, $R^2$, $R^3$, Y and Z are the same as defined above, or a salt thereof with a piperazine derivative of the formula:

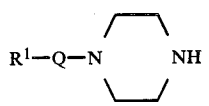
(V)

wherein $R^1$ and Q are the same as defined above, or a salt thereof; or

[Process (C)] reacting a thiazolidine derivative of the formula:

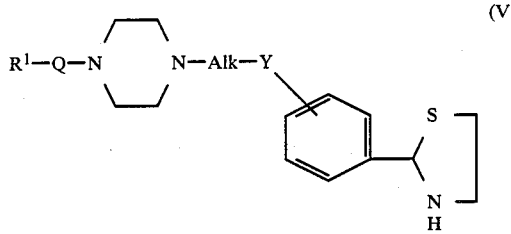
(VI)

wherein $R^1$, Q, Y and Alk are the same as defined above, or a salt thereof with a compound of the formula:

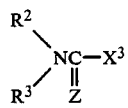
(VII)

wherein $X^3$ is a reactive residue and $R^2$, $R^3$ and Z are the same as defined above; or

[Process (D)] reacting a thiazolidine derivative of the formula:

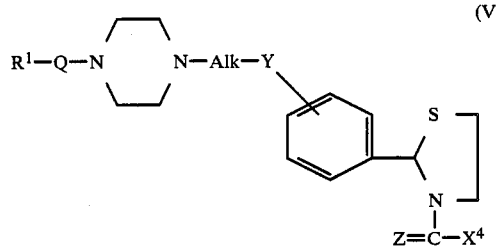
(VIII)

wherein $X^4$ is a reactive residue and $R^1$, Q, Alk, Y and Z are the same as defined above, or a salt thereof with an amine compound of the formula:

(IX)

wherein $R^2$ and $R^3$ are the same as defined above, or a salt thereof.

Alternatively, the compound (I) in which Z is oxygen atom [i.e., a thiazolidine derivative (I-a)] may be prepared by the step of:

[Process (E)] reacting a thiazolidine derivative of the formula:

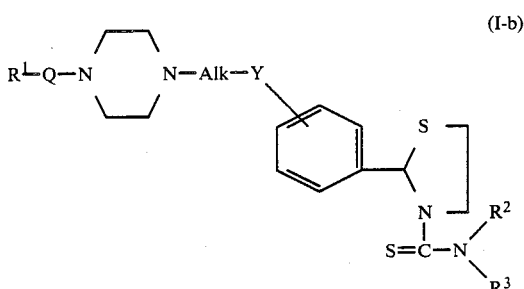
(I-b)

wherein $R^1$, $R^2$, $R^3$, Q, Y and Alk are the same as defined above, or a salt thereof with a glycidic compound of the formula:

(X)

wherein $R^4$ is a lower alkyl group or a substituted or unsubstituted phenyl group and $R^5$ is a lower alkyl group.

The compound (I) in which $R^3$ is hydrogen atom [i.e., a thiazolidine derivative (I-c)] may be prepared, for example, by the step of:

[Process (F)] reacting the thiazolidine derivative (VI) or a salt thereof with a compound of the formula:

$$R^2-NC=Z \quad (XI)$$

wherein $R^2$ and Z are the same as defined above.

Moreover, the compound (I) in which $R^2$ is a lower alkyl group and $R^3$ is a lower alkyl group, a cycloalkyl group, a lower alkanoyl group, a lower alkoxycarbonyl group, a lower alkylsulfonyl group, a benzoyl group or a phenyl group [i.e., a thiazolidine derivative (I-d)] may be prepared, for example, by the step of:

[Process (G)] reacting a thiazolidine derivative of the formula:

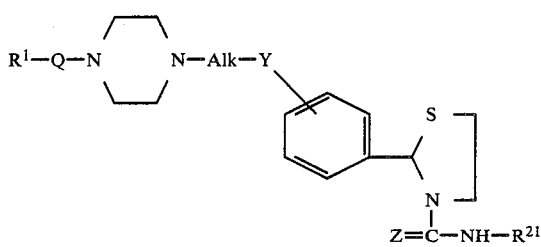

(I-e)

wherein $R^{21}$ is a lower alkyl group and $R^1$, Y, Q, Z and Alk are the same as defined above, or a salt thereof with a compound of the formula:

$$R^{31}X^5 \quad (XII)$$

wherein $R^{31}$ is a lower alkyl group, a cycloalkyl group, a lower alkanoyl group, a lower alkoxycarbonyl group, a lower alkylsulfonyl group, a benzoyl group or a phenyl group and $X^5$ is a reactive residue.

Further, the compound (I) in which $R^2$ is a lower alkanoyl group, a lower alkoxycarbonyl group, a lower alkylsulfonyl group or a benzoyl group and $R^3$ is hydrogen atom [i.e., a thiazolidine derivative (I-f)] may be prepared, for example, by the step of:

[Process (H)] hydrolyzing a thiazolidine derivative of the formula:

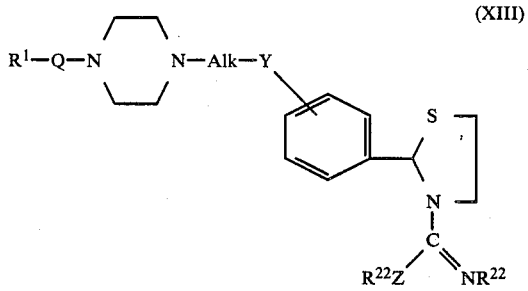

(XIII)

wherein $R^{22}$ is a lower alkanoyl group, a lower alkoxycarbonyl group, a lower alkylsulfonyl group or a benzoyl group and $R^1$, Q, Y, Z and Alk are the same as defined above, or a salt thereof.

Furthermore, the compound (I) in which both $R^2$ and $R^3$ are hydrogen atom [i.e., a thiazolidine derivative (I-g)] may be prepared, for example, by the step of:

[Process (I)] hydrolyzing the compound (I-f) or a salt thereof.

The starting compounds (II), (III), (IV), (V), (VI), (VIII), (IX) and (XIII) may be used either in free form or in the form of a salt thereof. Any conventional acid addition salts such as hydrochloride, hydrobromide, sulfate, nitrate and so forth may be used as the salts of the compounds (III), (V), (VI), (VIII), (IX) and (XIII). Alkali metal salts such as sodium salt or potassium salt, organic amine salts and so forth may be used as the salts of the compounds (II) and (IV). Moreover, the compounds (I-b), (I-e) and (I-f) of the present invention may be used in the above-mentioned reactions either in free form or in the form of salts thereof such as, for example, hydrochloride, hydrobromide, sulfate, nitrate, sodium salt, potassium salt and any other suitable salts. Further, examples of the starting compounds (III), (IV), (VII), (VIII) and (XII) include those in which the reactive residue defined for each one of the groups $X^1$, $X^2$, $X^3$, $X^4$ and $X^5$ is a halogen atom such as chlorine or bromine, a substituted or unsubstituted phenylsulfonyloxy group such as tosyloxy group, a lower alkylsulfonyloxy group such as methanesulfonyloxy group, or hydroxy group. When $R^{31}$ is a lower alkanoyl group, examples of the compound (XII) also includes a lower alkanoic acid or an acid anhydride thereof.

(Processes A, B, C and D)

All these reactions can be accomplished in the presence or absence of an acid acceptor in a solvent. Examples of the acid acceptors which may be used in these reactions include inorganic bases such as potassium hydroxide, sodium hydroxide, potassium carbonate, sodium carbonate, potassium bicarbonate or sodium bicarbonate, organic bases such as triethylamine, N-methylmorpholine, pyridine or diisopropylethylamine, and the like. Dimethylformamide, dimethylsulfoxide, acetonitrile, dioxane, tetrahydrofuran, acetone, methanol and ethanol are suitable as the reaction solvent for Processes (A) and (B), and tetrahydrofuran, dioxane, pyridine and dimethylformamide are suitable as the solvent for Process (C). On the other hand, examples of suitable solvents for Process (D) are tetrahydrofuran, toluene, acetonitrile and dioxane. It is preferred to carry out Processes (A) and (B) at about 50° to 110° C., especially at about 60° to 80° C. It is also preferred to carry out Process (C) at about 0° to 80° C., especially at about 25° to 60° C., and to carry out Process (D) at about 0° to 70° C., especially at about 10° to 50° C.

(Process E)

The reaction of the thiazolidine derivative (I-b) or a salt thereof with the glycidic compound (X) can be carried out in a solvent. Examples of the group represented by $R^4$ are a lower alkyl group such as methyl, ethyl, propyl or butyl, and a substituted or unsubstituted phenyl group such as phenyl, methylphenyl, methoxyphenyl or ethoxyphenyl. On the other hand, examples of the group represented by $R^5$ are a lower alkyl group such as methyl, ethyl, propyl or butyl. The glycidic compound (X) may exist in the form of cis- or trans-isomer, and either one of these isomers may be used in the reaction. Lower alkanols such as methanol, ethanol or propanol, tetrahydrofuran, dioxane and benzene are suitable as the solvent. The reaction temperature is preferably in the range of about 40° to 100° C., more preferably in the range of about 60° to 80° C.

(Process F)

The condensation reaction of the compound (VI) or a salt thereof and the compound (XI) can be carried out in a solvent. Examples of the solvent are methanol, ethanol, tetrahydrofuran, dioxane or acetonitrile. It is preferred to carry out the reaction at a temperature of about 25° to 100° C., especially at about 60° to 80° C. Alternatively, when $R^2$ is hydrogen, the compound (I-c) may be prepared by reacting the compound (VI) with an alkali metal salt of the compound (XI) ($R^2$=hydrogen) such as potassium isocyanate, sodium isocyanate, potassium isothiocyanate or sodium isothiocyanate in the presence of an acid (e.g., acetic acid, hydrochloric acid or sulfuric acid) in a solvent, since the compound (XI) in which $R^2$ is hydrogen is prepared from said alkali metal salt of the compound (XI) and the acid. Examples of the solvent are water, tetrahydrofuran, dioxane, lower alkanol (e.g., methanol, ethanol, propanol) or a mixture thereof. It is preferred to carry out the reaction at a temperature of about 0° to 60° C., especially at about 10° to 25° C.

(Process G)

The reaction of the compound (I-e) or a salt thereof and the compound (XII) may be carried out in a conventional manner. For instance, the reaction of the compound (I-e) with the compound (XII) ($X^5$=OH) may be carried out in the presence of a dehydrating agent (e.g., carbonyldiimidazole or dicyclohexylcarbodiimide) in a solvent. On the other hand, the reaction of the compound (I-e) with the compound (XII) ($X^5$=halogen atom, a substituted or unsubstituted phenylsulfonyloxy group, or a lower alkylsulfonyloxy group) or with the lower alkanoic acid anhydride may be carried out in a solvent in the absence or presence of an acid acceptor such as those described in Processes (A) to (D). Examples of the solvent are tetrahydrofuran, dioxane, benzene and toluene. The reaction may be carried out at a temperature of about 0° to 80° C., preferably at about 25° to 60° C.

(Processes H and I)

The hydrolysis of the compound (XIII) or (I-f) or a salt thereof can be accomplished in a conventional manner. For example, said hydrolysis may be carried out by treating the compound (XIII) or (I-f) with a base in a solvent. Examples of the base are alkali metal hydroxide such as sodium hydroxide or potassium hydroxide, and the like. The same solvent as used in Process (F) may be used in this reaction. It is preferred to carry out the reaction at a temperature of about 0° to 100° C.

When the compound (I) thus obtained is a racemic modification, said modification may be, if required, resolved into each optical isomer thereof. For example, the racemic modification of the compound (I) in which $R^2$ is lower alkyl and $R^3$ is hydrogen atom may be resolved into each optical isomer thereof by the steps of reacting said compound with an optically active 1-(2-naphthylsulfonyl)pyrrolidine-2-carbonyl halide to give a pair of diastereoisomers, separating said diastereoisomers from each other by selective crystallization or by column chromatography, and then hydrolyzing the each diastereoisomers.

The starting compounds (II), (IV), (VI), (VIII) and (XIII) are novel compounds. Among them, the starting compound (II) may be prepared, for example, by reacting a compound of the formula:

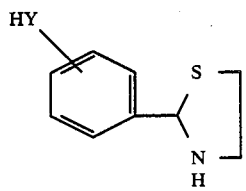
(XIV)

wherein Y is the same as defined above, with the compound (VII) in the same manner as described in Process (C). Alternatively, the compound (II) in which $R^3$ is a group other than di(lower alkyl)phosphoryl group may be prepared by reacting the compound (XIV) with the compound (XI) in the same manner as described in Process (F) to give a compound of the formula:

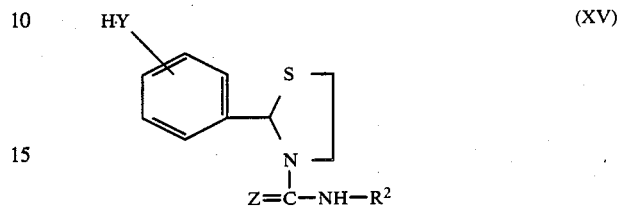
(XV)

wherein $R^2$, Y and Z are the same as defined above, and when $R^2$ is a lower alkyl group, optionally reacting the thus-obtained product with the compound (XII) in the same manner as described in Process (G). The compound (IV) may be prepared by reacting the compound (II) with a compound of the formula:

$$X^2\text{-Alk-}X^6 \quad (XVI)$$

wherein $X^6$ is a reactive residue such as halogen atom, a substituted or unsubstituted phenylsulfonyloxy group or a lower alkylsulfonyloxy group and Alk and $X^2$ are the same as defined above, at about 0° to 100° C. in the presence of an acid acceptor such as those described in Processes (A) to (D).

The compound (IV) may also be prepared by reacting a compound of the formula:

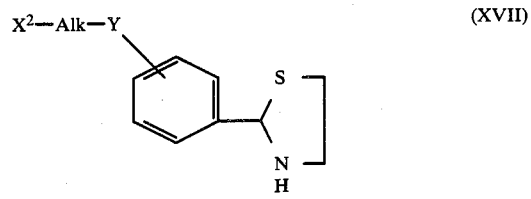
(XVII)

wherein Alk, Y and $X^2$ are the same as defined above, with the compound (VII) in the same manner as described in Process (C). Alternatively, the compound (IV) in which $R^3$ is a group other than di(lower alkyl)-phosphoryl group may be prepared by reacting the compound (XVII) with the compound (XI) in the same manner as described in Process (F) to give a compound of the formula:

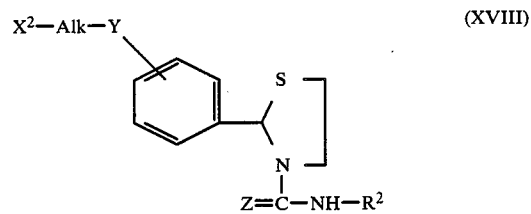
(XVIII)

wherein $R^2$, Alk, Y, Z and $X^2$ are the same as defined above, and when $R^2$ is a lower alkyl group, optionally reacting the thus-obtained product with the compound (XII) in the same manner as described in Process (G). The compound (VI) may be prepared by condensing a compound of the formula:

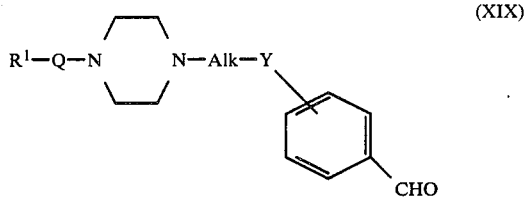

wherein $R^1$, Q, Alk and Y are the same as defined above, with cysteamine or a salt thereof at about 25° to 100° C. in the absence or presence of an acid acceptor such as those described in Processes (A) to (D). The reaction of the compound (VI) or a salt thereof with a compound of the formula: $Z=C-(X^4)_2$ (XX) ($X^4$ and Z: same as defined above) gives the compound (VIII), and also the reaction of the compound (I-g) or a salt thereof with a compound of the formula: $R^{22}X^7$ (XXI) ($X^7$=halogen atom, a substituted or unsubstituted phenylsulfonyloxy group or a lower alkylsulfonyloxy group; and $R^{22}$ is the same as defined above) gives the compound (XIII). These reactions may be carried out at a temperature of about 0° to 80° C. in the absence or presence of an acid acceptor such as those described in Processes (A) to (D).

The compounds (II), (IV), (VI), (VIII), (XIII), (I-b), (I-e), (I-f) and (I-g) obtained above may be used in the subsequent step or steps without isolation and/or purification from the reaction mixture.

The compound (I) of the present invention can be used as a medicine in the form of either a free form or a pharmaceutically acceptable salt thereof. Any pharmaceutically acceptable salts of the compound (I) may be used for this purpose, and such salts include, for example, inorganic acid addition salts (e.g., hydrochloride, sulfate, nitrate, phosphate or hydrobromide), organic acid addition salts (e.g., acetate, oxalate, fumarate, succinate, maleate, citrate, lactate, glucuronate, pyruvate, tartrate, sulfamate, benzenesulfonate or methanesulfonate) and alkali metal salts (e.g., sodium or potassium salt). These salts may easily be prepared by treating a free form of the compound (I) with an acid or an alkali agent in a conventional manner.

The compound (I) of the present invention and a salt thereof have potent and long-lasting cardiotonic effects, and are useful for treatment or prophylaxis of congestive heart failure. For example, the compound (I) and a salt thereof are useful for the treatment, prophylaxis and/or amelioration of various symptoms such as, for example, edema, dyspnea, cyanosis and hypoxia which are usually observed in patients with heart failure.

Moreover, the compound (I) of the present invention or a salt thereof shows no substantial adrenergic β-receptor stimulating action and is especially characterized by its selective activation of heart muscle and/or its low side effects (e.g., the effect on heart rate).

The compound (I) and a pharmaceutically acceptable salt thereof can be administered by either oral or parenteral route. However, as they show excellent cardiotonic activity by oral administration, they are particularly suitable for use by the oral route. For oral administration, the compound (I) and a salt thereof may be used in the form of conventional preparations, e.g., tablets, powders, capsules or granules, which may contain conventional carriers, e.g., calcium carbonate, calcium phosphate, corn starch, potato starch, sucrose, lactose, talc or magnesium stearate. They may also be used in liquid preparations, e.g., aqueous or oily suspensions, solutions, syrups or elixirs. For parenteral administration, the compound (I) and a salt thereof may be used for example in the form of an injection preparation or suppository. The injection preparation may be in the form of a solution or a suspension which may contain distilled water, an essential oil (e.g., peanut oil or corn oil) or hydrophobic solvent (e.g., polyethylene glycol, polypropylene glycol, lanoline or coconut oil). These preparations may be sterilized and further may contain for example other conventional additives, e.g. preservatives or stabilizers.

The dose of the compound (I) or a salt thereof may vary according to the administration route, the age, body weight and condition of the patient and the kind and severity of the disease, but is preferably in the range of 0.001 to 10 mg/kg/day, more preferably 0.003 to 5 mg/kg/day.

Practical and presently-preferred embodiments of the present invention are illustratively shown by the following Experiments and Examples, but should not be construed to be limited thereto.

EXPERIMENT 1

Method: Male mongrel dogs weighing 10 to 20 kg were anesthetized with sodium pentobarbitol (30 mg/kg, i.v.). Thoracotomy was performed at the left fourth intercostal space. Left ventricular pressure was measured by a small pressure transducer inserted into the left ventricle. Cardiotonic activity of a test compound was assessed by an increase in the first derivative of left ventricular pressure. The test compound was dissolved in 5% glucose solution and administered intravenously to dogs.

Results: The results are shown in Table 1.

TABLE 1
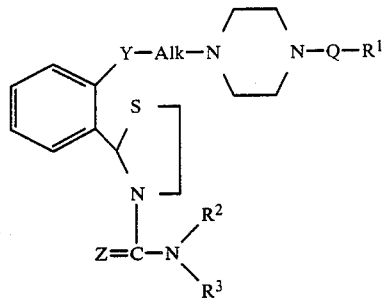
(I-A)
| R¹ | Alk | Y | Z | R² | R³ | optical isomer | Dose (mg/kg) | Increase (%) in left ventricular contractility | Duration of action (minute) |
|---|---|---|---|---|---|---|---|---|---|
| C₆H₅- | —(CH₂)₂— | O | O | CH₃ | H | ± | 0.003 | 30 | 30 |
| C₆H₅- | " | " | " | " | " | − | 0.003 | 36 | 40 |
| C₆H₅- | " | " | " | " | " | + | 0.01 | 20 | 30 |
| C₆H₅- | " | S | " | " | " | ± | 0.03 | 19 | 20 |
| C₆H₅- | " | O | S | " | " | − | 0.01 | 22 | 25 |
| F-C₆H₄- | " | " | " | " | " | ± | 0.003 | 20 | 30 |
| F-C₆H₄- | " | " | O | " | " | ± | 0.01 | 40 | 40 |
| F-C₆H₄- | " | " | " | H | " | ± | 0.01 | 40 | 20 |
| F-C₆H₄- | " | " | " | CH₃ | CH₃ | ± | 0.03 | 70 | 30 |
| F-C₆H₄- | " | " | " | " | CH₃CO | ± | 0.03 | 40 | 40 |

TABLE 1-continued (I-A)

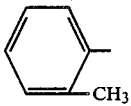

| Test compound (I-A) (Q = single bond) | | | | | | | Cardiotonic activity | |
|---|---|---|---|---|---|---|---|---|
| R¹ | Alk | Y | Z | R² | R³ | optical isomer | Dose (mg/kg) | Increase (%) in left ventricular contractility | Duration of action (minute) |

| R¹ | Alk | Y | Z | R² | R³ | optical isomer | Dose (mg/kg) | Increase (%) in left ventricular contractility | Duration of action (minute) |
|---|---|---|---|---|---|---|---|---|---|
|  | " | " | " | " | H | ± | 0.01 | 30 | 35 |
| 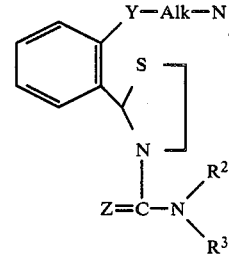 | —(CH₂)₃— | S | S | " | " | ± | 0.03 | 26 | 20 |

Experiment 2

Method: The isolated hearts of guinea pigs (weighing: about 280 g) were perfused with the Langendorff's method. Locke-Ringer's solution containing 2% of defibrinated rabbit blood was used as a perfusing solution (at 30° C.). Contractile force was measured by means of a strain gauge transducer. A test compound was dissolved in a saline salution and administered into an aortic cannula.

Results: The results are shown in Table 2.

TABLE 2

(I-A)

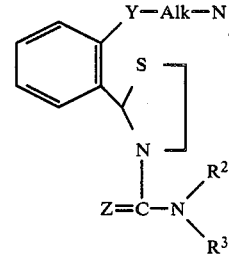

| Test Compound (I-A) (R² = CH₃, R³ = H, Q = single bond) | | | | | Cardiotonic activity Minimum effective dose* (μg/heart) |
|---|---|---|---|---|---|
| R¹ | Alk | Y | Z | Optical isomer | |
| 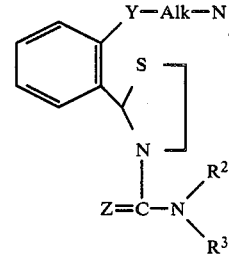 | —(CH₂)₂— | O | O | ± | 3 |
| 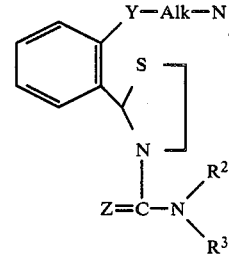 | " | " | " | — | 10 |

TABLE 2-continued (I-A)

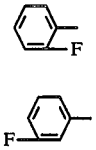

| Test Compound (I-A) (R² = CH₃, R³ = H, Q = single bond) | | | | | Cardiotonic activity Minimum effective dose* (μg/heart) |
|---|---|---|---|---|---|
| R¹ | Alk | Y | Z | Optical isomer | |
| 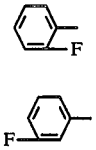 | " | " | " | + | 3 |
| " | " | S | S | ± | 3 |
| " | " | O | " | + | 1 |
| " | " | " | " | — | 10 |
| (with F) | " | " | " | ± | 1 |
| (F-phenyl) | " | " | O | ± | 10 |

TABLE 2-continued (I-A)

[Structure: Y—Alk—N(piperazine)N—Q—R¹, with phenyl ring fused to thiazolidine bearing Z=C—N(R²)(R³)]

Note:
*The minimum effective dose means a minimum amount which is necessary to produce an increase in cardiac contractile force of the isolated guinea pig's heart.

| Test Compound (I-A) (R² = CH₃, R³ = H, Q = single bond) | | | | Cardiotonic activity Minimum effective dose* (μg/heart) |
|---|---|---|---|---|
| R¹ | Alk | Y | Z Optical isomer | |
| F—⟨phenyl⟩— | " | " | S  ± | 1 |
| CH₃O—⟨phenyl⟩— | " | " | "  ± | 3 |
| ⟨phenyl⟩—OCH₃ (meta) | " | " | "  ± | 3 |

EXAMPLE 1

A mixture of 2.38 g of N-methyl-2-(2-hydroxyphenyl)thiazolidine-3-carboxamide, 1.38 g of potassium carbonate, 0.7 g of sodium iodide, 3.36 g of 1-(2-chloroethyl)-4-phenylpiperazine and 25 ml of dimethylformamide is stirred at 90° C. for 24 hours. The mixture is concentrated under reduced pressure to remove dimethylformamide. Water is added to the residue, and the aqueous mixture is extacted with ethyl acetate. The extract is washed with dilute sodium hydroxide solution and water, successively. The ethyl acetate solution is dried and then concentrated under reduced pressure to remove solvent. The residue is purified by silica gel chromatography (sovent, benzene:ethyl acetate—1:5). 1.89 g of N-methyl-2-{2-[2-(4-phenylpiperazin-1-yl)ethyloxy]phenyl}thiazolidine-3-carboxamide are obtained.

M.p. 127°–129° C. (recrystallized from ethyl acetate-n-hexane).

M.P. 133°–135° C. (recrystallized from ethyl acetate-ether)

Oxalate:
M.p. 169.5°–172.5° C. (decomp.) (recrystallized from acetone)

Hemifumarate:
M.p. 169°–170° C. (decomp.) (recrystallized from ethanol-ether)

Hemisuccinate:
M.p. 122°–124° C. (decomp.) (recrystallized from acetone-ether)

Methanesulfonate monohydrate:
M.p. 110°–117° C. (decomp.) (recrystallized from acetone)

Hydrochloride:
M.p. 195°–197° C. (decomp.) (recrystallized from methanol-acetone-ether)

Dihydrochloride:
M.p. 206°–207° C. (decomp.) (recrystallized from methanol-ether)

EXAMPLES 2 TO 7

The following compounds are obtained from the corresponding thiazolidine and piperazine compounds in the same manner as described in Example 1.

TABLE 3

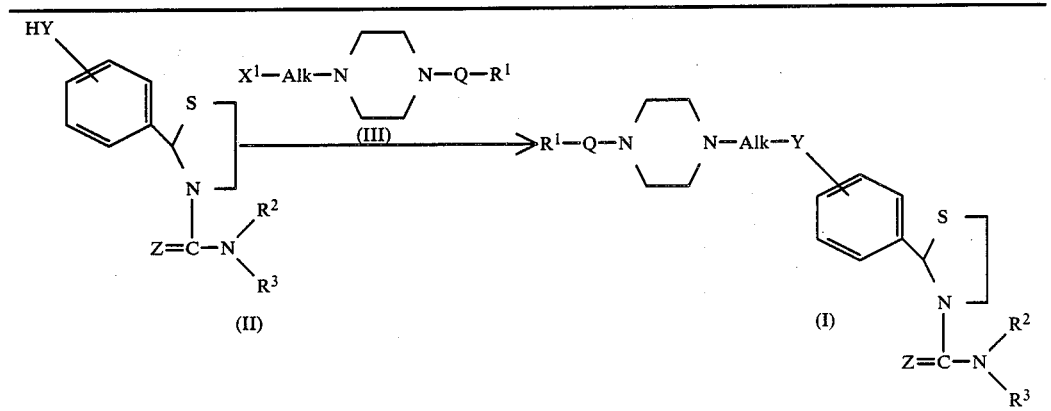

(Q = Single bond, R² = CH₃, R³ = H, X¹ = Cl)

| Ex. Nos. | Compound (I) | | | | | Properties |
|---|---|---|---|---|---|---|
| | R¹ | Alk | Y | position* | Z | |
| 2 | ⟨phenyl⟩—F | —(CH₂)₂— | O | 2 | O | M.p. 156–157° C. (recrystallized from acetone-n-hexane) Hemifurate: M.p. 173–176° C. (decomp.) (recrystallized from acetone) Oxalate: M.p. 173–175° C. (decomp.) (recrystallized from acetone) |

TABLE 3-continued

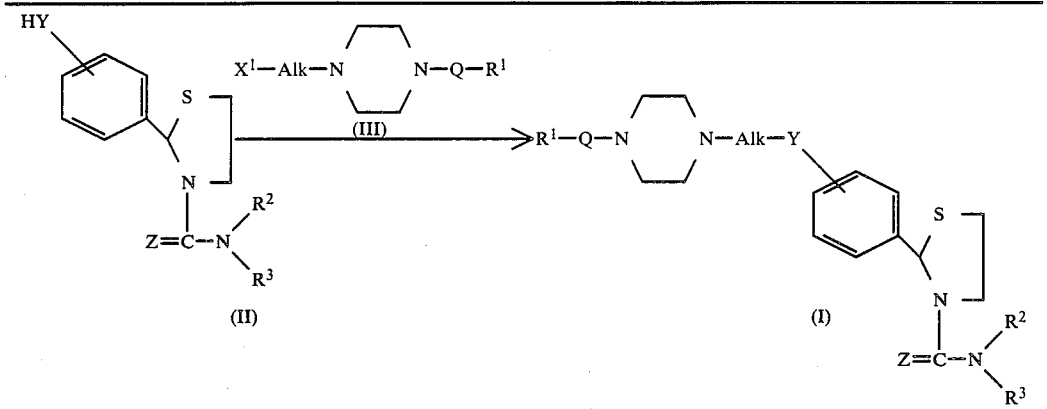

(Q = Single bond, R² = CH₃, R³ = H, X¹ = Cl)

| Ex. Nos. | R¹ (Compound (I)) | Alk | Y | position* | Z | Properties |
|---|---|---|---|---|---|---|
| 3 | 3-F-phenyl | " | " | " | S | Yield: 56.7% M.p. 138–139° C. (recrystallized from ethyl acetate-n-hexane) Fumarate: M.p. 162–164° C. (decomp.) (recrystallized from methanol-acetone) |
| 4 | phenyl | —(CH₂)₃— | " | " | " | Yield: 51.5% M.p. 120–123° C. (recrystallized from ethanol-ether) fumarate: M.p. 125–128° C. (decomp.) (recrystallized from ethanol-ether) |
| 5 | 3-F-phenyl | " | " | 4 | O | IR$\nu_{max}^{nujol}$ (cm⁻¹): 3420, 3330, 1630 Oxalate: M.p. 134–135° C. (decomp.) (recrystallized from ethanol) |
| 6 | 3-F-phenyl | " | " | " | S | M.p. 145–147° C. (recrystallized from ethyl acetate-n-hexane) Trihydrochloride: M.p. 170–175° C. (decomp.) (recrystallized from methanol-ether) |
| 7 | 2-OCH₃-phenyl | " | " | " | " | oil Trihydrochloride: M.p. 173–180° C. (decomp.) |

*Position means the position of the group

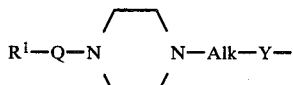

which is substituted on the benzene ring (the carbon atom of benzene ring which carries a thiazolidine group is taken as the 1-position).

TABLE 3-continued

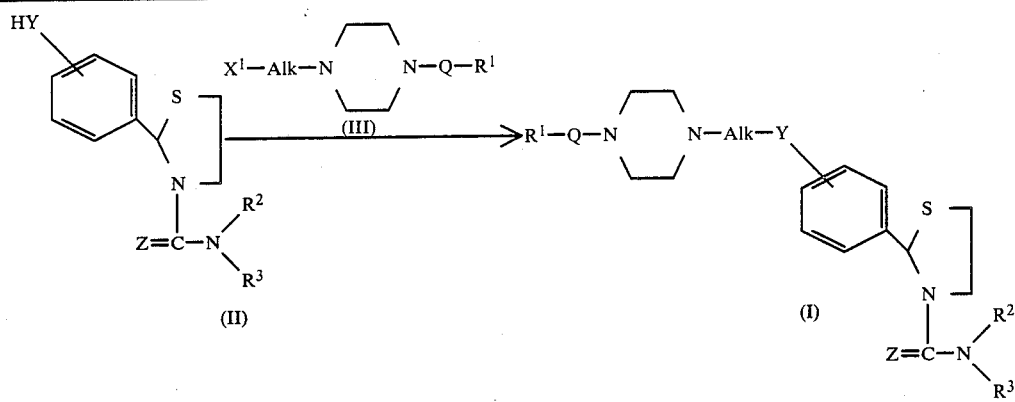

(Q = Single bond, $R^2$ = $CH_3$, $R^3$ = H, $X^1$ = Cl)

| | Compound (I) | | | | | |
|---|---|---|---|---|---|---|
| Ex. Nos. | $R^1$ | Alk | Y | position* | Z | Properties |

EXAMPLE 8

A mixture of 1.81 g of N-methyl-2-{2-(2-chloroethyloxy)phenyl]thiazolidine-3-carboxamide, 0.97 g of N-phenylpiperazine, 0.83 g of potassium carbonate, 0.90 g of sodium iodide and 25 ml of dimethylformamide is stirred at 90° C. for 18 hours. The mixture is concentrated under reduced pressure to remove solvent. Water is added to the residue, and the aqueous mixture is extracted with ethyl acetate. The extract is washed with water, dried and then concentrated under reduced pressure to remove solvent. The residue is crystallized with isopropyl ether, and the crystals are recrystallized from a mixture of ethyl acetate and n-hexane. 1.48 g of N-methyl-2-{2-[2-(4-phenylpiperazin-1-yl)ethyloxy]-phenyl}thiazolidine-3-carboxamide are obtained. Yield: 57.8%

The physico-chemical properties of this compound are identical with those of the compound obtained in Example 1.

EXAMPLES 9 TO 55

The following compounds are obtained from the corresponding thiazolidine and piperazine compounds in the same manner as described in Example 8.

TABLE 4

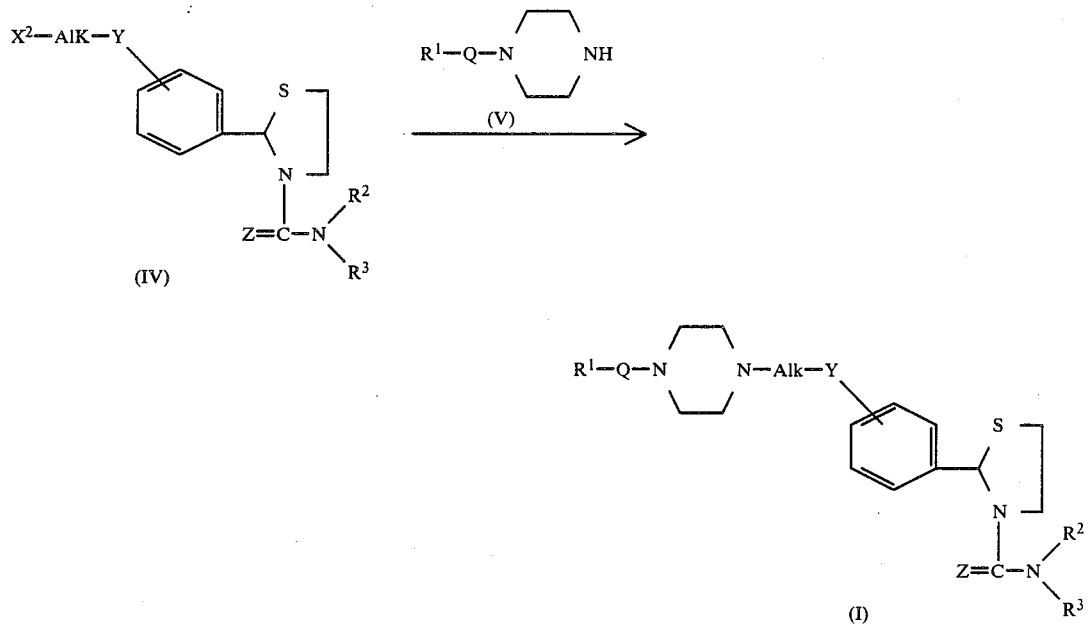

(R² = CH₃, R³ = H, X² is Cl except that X² of Example 37 is Br)

| Ex. Nos. | R¹ | Q and Alk | Y | position* | Z | Properties (Compound (I)) |
|---|---|---|---|---|---|---|
| 9 | 3-F-phenyl | Q = Single bond<br>Alk = —(CH₂)₂— | O | 2 | O | Yield: 52.9%<br>M.p. 156–157° C. (recrystallized from acetone-n-hexane)<br>Hemifumarate:<br>M.p. 173–176° C. (decomp.)<br>(recrystallized from acetone)<br>Oxalate:<br>M.p. 173–175° C. (decomp.)<br>(recrystallized from acetone) |
| 10 | 2-F-phenyl | Q = Single bond<br>Alk = —(CH₂)₂— | " | " | " | Oxalate:<br>M.p. 175–176° C. (decomp.)<br>(recrystallized from acetone)<br>Yield: 89.5% |
| 11 | 4-F-phenyl | Q = Single bond<br>Alk = —(CH₂)₂— | " | " | " | Yield: 77%<br>M.p. 134–136° C. (recrystallized from ethyl acetate-n-hexane)<br>Oxalate:<br>M.p. 120–123° C. (decomp.)<br>(recrystallized from acetone) |
| 12 | 3-Cl-phenyl | Q = Single bond<br>Alk = —(CH₂)₂— | " | " | " | Yield: 66%<br>M.p. 119–121° C. (recrystallized from ethyl acetate-ether)<br>Oxalate:<br>M.p. 138–139° C. (decomp.)<br>(recrystallized from ethanol-ether) |
| 13 | 2-CH₃-phenyl | Q = Single bond<br>Alk = —(CH₂)₂— | " | " | " | Yield: 73%<br>M.p. 162–163° C. (recrystallized from chloroform-ether)<br>Oxalate:<br>M.p. 183–184° C. (decomp.)<br>(recrystallized from ethanol) |
| 14 | 3-CH₃-phenyl | Q = Single bond<br>Alk = —(CH₂)₂— | " | " | " | Yield: 71%<br>M.p. 112–114° C. (recrystallized from ethyl acetate-ether)<br>Oxalate:<br>M.p. 153–154° C. (decomp.)<br>(recrystallized from ethanol-ether) |

TABLE 4-continued

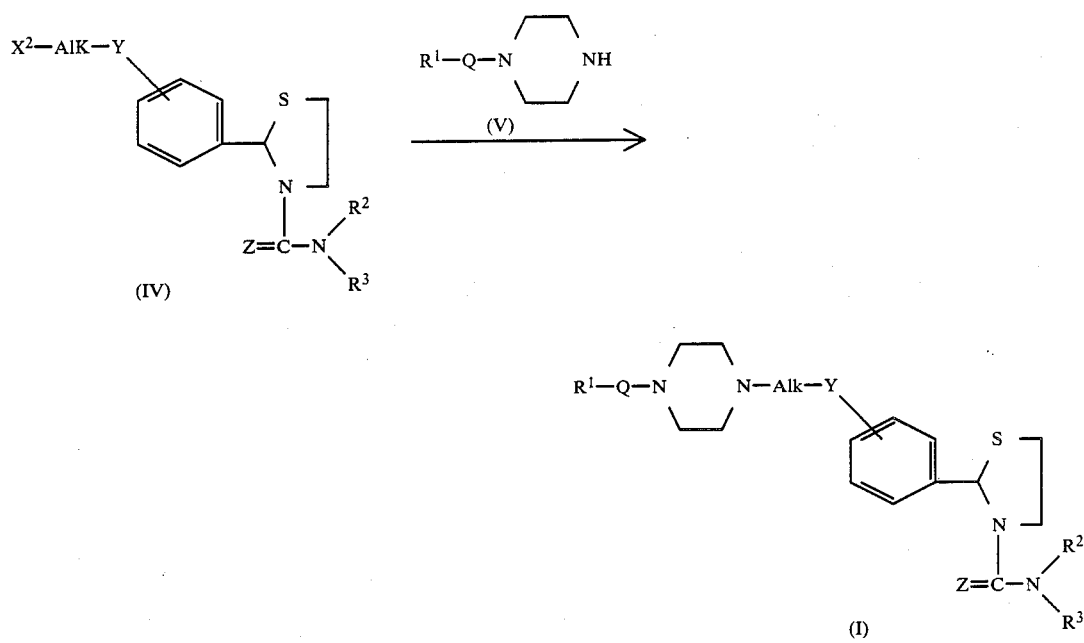

(R² = CH₃, R³ = H, X² is Cl except that X² of Example 37 is Br)

| Ex. Nos. | R¹ | Q and Alk | Y | position* | Z | Properties |
|---|---|---|---|---|---|---|
| 15 | 3-OCH₃-phenyl | Q = Single bond<br>Alk = —(CH₂)₂— | " | " | " | Yield: 78%<br>M.p. 123–124° C. (recrystallized from chloroform-ether)<br>Oxalate:<br>M.p. 151–152° C. (decomp.)<br>(recrystallized from ethanol-ether) |
| 16 | 3-F-phenyl | Q = Single bond<br>Alk = —(CH₂)₂— | " | " | S | M.p. 138–139.5° C. (recrystallized from ethyl acetate-n-hexane)<br>Fumarate:<br>M.p. 162–164° C. (decomp.)<br>(recrystallized from methanol-acetone) |
| 17 | phenyl | Q = Single bond<br>Alk = —(CH₂)₂— | S | " | " | M.p. 141–145° C.<br>Oxalate:<br>M.p. 195–196° C. (decomp.)<br>(recrystallized from ethanol-methanol) |
| 18 | phenyl | Q = Single bond<br>Alk = —(CH₂)₂— | " | " | O | Yield: 61.4%<br>M.p. 126–128° C. (recrystallized from ethanol-ether)<br>Oxalate hemihydrate:<br>M.p. 175–177° C. (decomp.)<br>(recrystallized from ethanol-ether) |
| 19 | 3-F-phenyl | Q = Single bond<br>Alk = —(CH₂)₂— | " | " | S | Yield: 69.8%<br>M.p. 115–120° C.<br>Oxalate<br>M.p. 176–178° C. (decomp.)<br>(recrystallized from methanol-ethanol-ether) |
| 20 | 3-F-phenyl | Q = Single bond<br>Alk = —(CH₂)₂— | " | " | O | Yield: 67.3%<br>M.p. 127–128° C. (recrystallized from ethanol-ether)<br>Oxalate:<br>M.p. 141–143° C. (decomp.)<br>(recrystallized from ethanol-ether) |

TABLE 4-continued

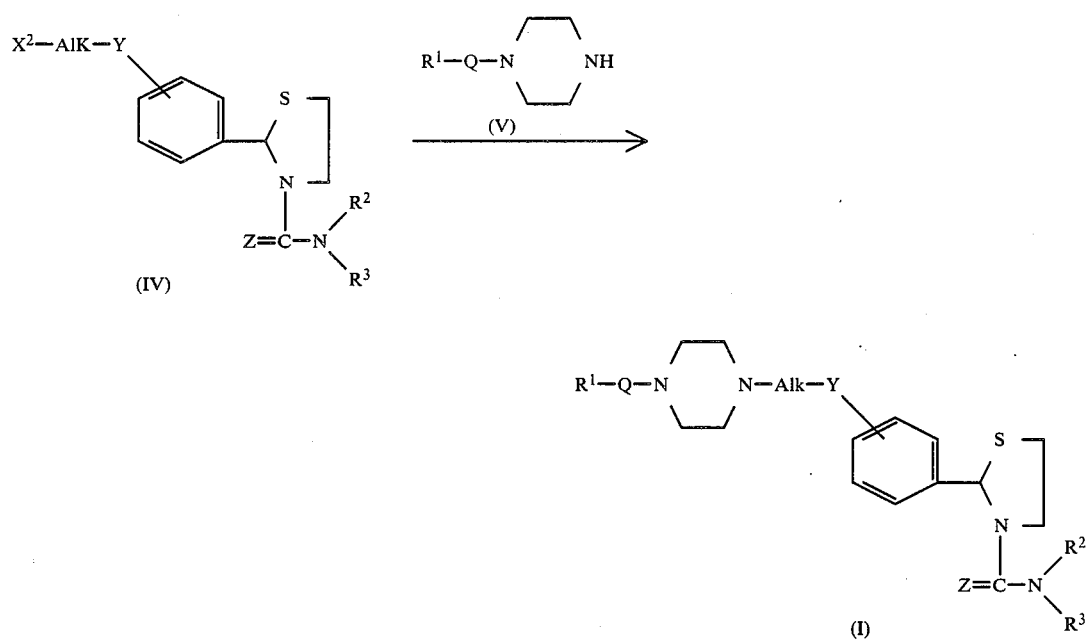

($R^2 = CH_3$, $R^3 = H$, $X^2$ is Cl except that $X^2$ of Example 37 is Br)

| Ex. Nos. | $R^1$ | Q and Alk | Y | position* | Z | Properties |
|---|---|---|---|---|---|---|
| 21 | phenyl | Q = Single bond<br>Alk = —(CH$_2$)$_3$— | O | " | " | Yield: 65.7%<br>M.p. 85.5–90° C. (recrystallized from ethyl acetate-n-hexane)<br>Oxalate:<br>M.p. 118–130° C. (decomp.)<br>(recrystallized from ethanol-ether) |
| 22 | 2-F-phenyl | Q = Single bond<br>Alk = —(CH$_2$)$_3$— | " | " | " | Yield: 58%<br>M.p. 121–129° C. (recrystallized from ethyl acetate-isopropyl ether-n-hexane)<br>Oxalate:<br>M.p. 126–134° C. (decomp.)<br>(recrystallized from ethanol-ether) |
| 23 | 3-F-phenyl | Q = Single bond<br>Alk = —(CH$_2$)$_3$— | " | " | " | Yield: 67.7%<br>M.p. 103–105° C. (recrystallized from ethyl acetate-n-hexane)<br>Oxalate:<br>M.p. 150–151.5° C. (decomp.)<br>(recrystallized from ethanol-ether) |
| 24 | phenyl | Q = Single bond<br>Alk = —(CH$_2$)$_3$— | S | " | " | Yield: 83.4%<br>M.p. 111–114° C.<br>Oxalate ½C$_2$H$_5$OH:<br>M.p. 125–127° C. (decomp.)<br>(recrystallized from ethanol-ether) |
| 25 | 3-F-phenyl | Q = Single bond<br>Alk = —(CH$_2$)$_3$— | " | " | " | Yield: 86.4%<br>M.p. 115–119° C.<br>Oxalate:<br>M.p. 136–138° C. (decomp.)<br>(recrystallized from ethanol-ether) |
| 26 | 3-F-phenyl | Q = Single bond<br>Alk = —(CH$_2$)$_3$— | " | " | S | Yield: 70.2%<br>M.p. 105–109° C.<br>Oxalate:<br>M.p. 169.5–171° C. (decomp.)<br>(recrystallized from methanol-ether) |

TABLE 4-continued

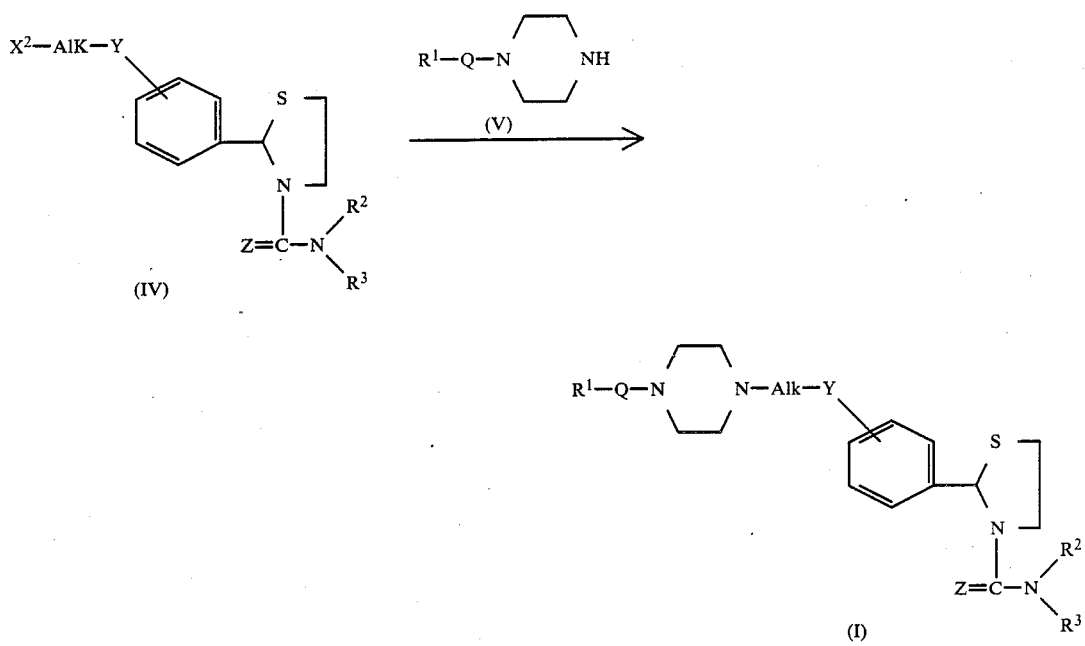

($R^2 = CH_3$, $R^3 = H$, $X^2$ is Cl except that $X^2$ of Example 37 is Br)

| Ex. Nos. | $R^1$ | Q and Alk | Y | position* | Z | Properties |
|---|---|---|---|---|---|---|
| 27 | phenyl | Q = Single bond<br>Alk = $-(CH_2)_4-$ | O | " | " | M.p. 105–110° C. (recrystallized from isopropyl alcohol)<br>Fumarate:<br>M.p. 145–147° C. (decomp.)<br>(recrystallized from acetone-n-hexane) |
| 28 | 4-Cl-phenyl | Q = Single bond<br>Alk = $-(CH_2)_4-$ | " | " | " | M.p. 117–122° C. (recrystallized from ethyl acetate-n-hexane)<br>Oxalate:<br>M.p. 164–168° C. (decomp.)<br>(recrystallized from methanol-ether) |
| 29 | phenyl | Q = $-CH_2-$<br>Alk = $-(CH_2)_3-$ | " | " | O | Yield: 72.7%<br>M.p. 125.5–126.5° C. (recrystallized from ethyl acetate-n-hexane)<br>Dimaleate:<br>M.p. 172–174° C. (decomp.)<br>(recrystallized from acetone) |
| 30 | 3-F-phenyl | Q = $-CH_2-$<br>Alk = $-(CH_2)_3-$ | " | " | S | Yield: 68.1%<br>M.p. 78–83° C. (recrystallized from ether-n-hexane)<br>2.7 hydrochloride:<br>M.p. 205–208° C. (decomp.)<br>(recrystallized from methanol-acetone-ether) |
| 31 | 3-OCH$_3$-phenyl | Q = $-CH_2-$<br>Alk = $-(CH_2)_3-$ | " | " | " | Yield: 69.4%<br>M.p. 105–110° C. (recrystallized from acetone-n-hexane)<br>Difumarate:<br>M.p. 152–156° C. (decomp.)<br>(recrystallized from acetone) |
| 32 | phenyl | Q = $-(CH_2)_2-$<br>Alk = $-(CH_2)_2-$ | " | " | " | Yield: 58.4%<br>M.p. 124–125.5° C. (recrystallized from isopropyl alcohol-isopropyl ether)<br>Fumarate:<br>M.p. 170–175° C. (decomp.)<br>(recrystallized from methanol) |

TABLE 4-continued

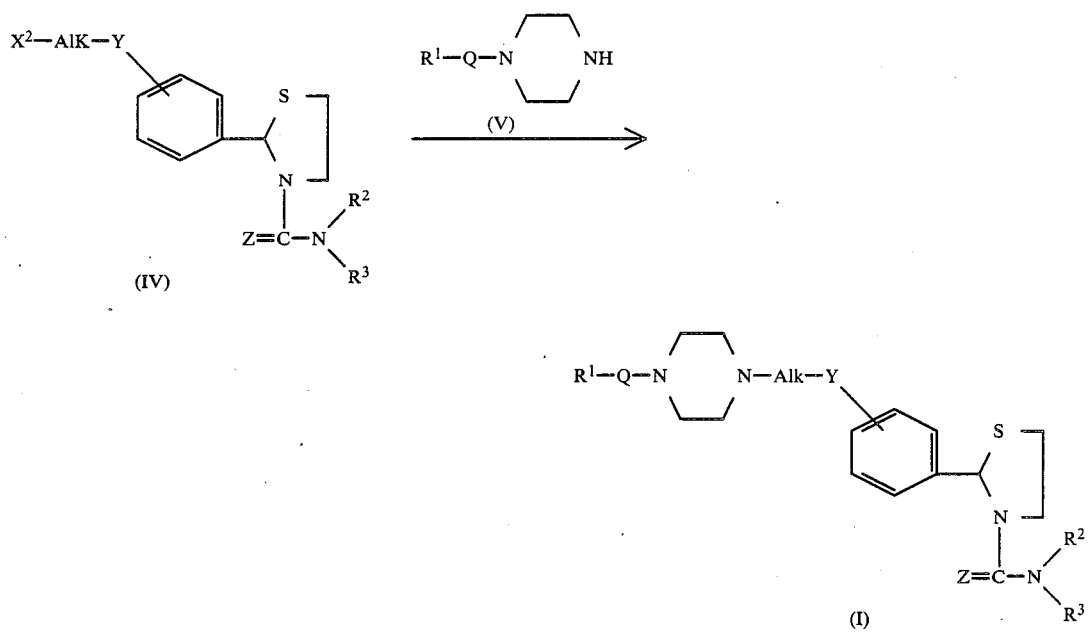

($R^2$ = $CH_3$, $R^3$ = H, $X^2$ is Cl except that $X^2$ of Example 37 is Br)

| Ex. Nos. | $R^1$ | Q and Alk | Y | position* | Z | Properties |
|---|---|---|---|---|---|---|
| 33 | phenyl | Q = —(CH$_2$)$_2$—<br>Alk = —(CH$_2$)$_3$— | " | " | " | Yield: 74.7%<br>M.p. 114–115° C. (recrystallized from isopropyl alcohol-isopropyl ether)<br>Difumarate:<br>M.p. 178–181° C. (decomp.)<br>(recrystallized from methanol) |
| 34 | phenyl | Q = —(CH$_2$)$_3$—<br>Alk = —(CH$_2$)$_2$— | " | " | " | M.p. 103–106° C. (recrystallized from ether-n-hexane)<br>Difumarate:<br>M.p. 177–178° C. (decomp.)<br>(recrystallized from acetone) |
| 35 | phenyl | Q = —(CH$_2$)$_3$—<br>Alk = —(CH$_2$)$_3$— | " | " | " | M.p. 55–60° C. (recrystallized from ether-n-hexane)<br>Difumarate:<br>M.p. 167–169° C. (decomp.)<br>(recrystallized from methanol-ether) |
| 36 | phenyl | Q = —CH=CHCH$_2$—<br>Alk = —(CH$_2$)$_2$— | " | " | " | M.p. 141–144° C. (recrystallized from ethyl acetate-n-hexane)<br>Dioxalate monohydrate:<br>M.p. 196–198° C. (decomp.)<br>(recrystallized from acetone) |
| 37 | phenyl | Q = Single bond<br>Alk = —(CH$_2$)$_2$— | " | 4 | O | Yield: 79%<br>M.p. 85–91° C. (recrystallized from ethyl acetate-n-hexane)<br>Oxalate:<br>M.p. 125–130° C. (decomp.) |
| 38 | phenyl | Q = Single bond<br>Alk = —(CH$_2$)$_2$— | " | " | S | Yield: 65.9%<br>oil<br>Trihydrochloride:<br>M.p. 164–167° C. (decomp.)<br>(recrystallized from ethanol-acetone-ether) |
| 39 | 3-fluorophenyl | Q = Single bond<br>Alk = —(CH$_2$)$_2$— | " | " | " | Yield: 67.8%<br>M.p. 123–125° C. (recrystallized from ethyl acetate-n-hexane)<br>Oxalate:<br>M.p. 153–155° C. (decomp.)<br>(recrystallized from acetone) |

TABLE 4-continued

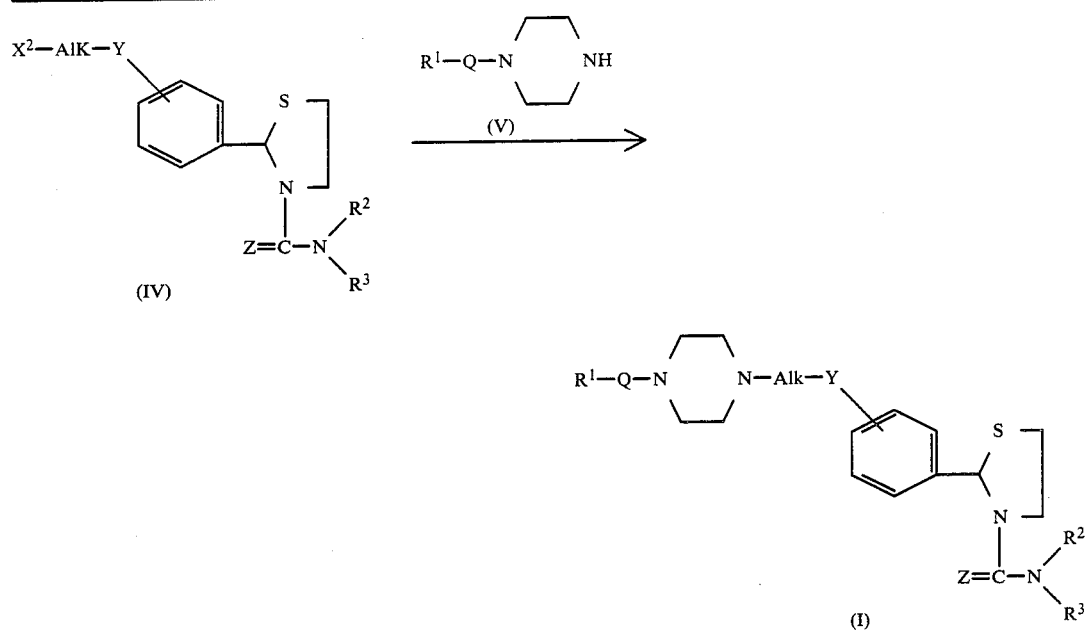

($R^2 = CH_3$, $R^3 = H$, $X^2$ is Cl except that $X^2$ of Example 37 is Br)

| Ex. Nos. | $R^1$ | Q and Alk | Y | position* | Z | Properties |
|---|---|---|---|---|---|---|
| 40 | 2-F-phenyl | Q = Single bond<br>Alk = —(CH₂)₂— | " | " | " | Yield: 61.9%<br>M.p. 101–103° C. (recrystallized from ethyl acetate-n-hexane)<br>Oxalate:<br>M.p. 80–90° C. (decomp.)<br>(recrystallized from acetone) |
| 41 | 2-CH₃-phenyl | Q = Single bond<br>Alk = —(CH₂)₂— | " | " | " | Yield: 50.7%<br>M.p. 134–136° C. (recrystallized from ethyl acetate-n-hexane)<br>2.5 hydrochloride:<br>M.p. 168–171° C. (decomp.)<br>(recrystallized from methanol-ether) |
| 42 | 3-CH₃-phenyl | Q = Single bond<br>Alk = —(CH₂)₂— | " | " | " | Yield: 62.8%<br>M.p. 85–95° C. (recrystallized from benzene-n-hexane)<br>(containing ⅓ benzene)<br>Oxalate:<br>M.p. 115–120° C. (decomp.)<br>(recrystallized from ethanol-ether) |
| 43 | 4-CH₃O-phenyl | Q = Single bond<br>Alk = —(CH₂)₂— | " | " | " | Yield: 70.4%<br>oil<br>Trihydrochloride:<br>M.p. 167–169° C. (decomp.)<br>(recrystallized from ethanol-acetone-ether) |
| 44 | phenyl | Q = Single bond<br>Alk = —(CH₂)₂— | S | " | " | oil<br>Oxalate:<br>M.p. 159–163° C. (decomp.)<br>(recrystallized from methanol) |
| 45 | phenyl | Q = Single bond<br>Alk = —(CH₂)₂— | " | " | O | Yield: 67%<br>oil<br>Oxalate hemihydrate:<br>M.p. 120–125° C. (recrystallized from ethanol) |
| 46 | phenyl | Q = Single bond<br>Alk = —(CH₂)₃— | O | " | " | Yield: 70%<br>M.p. 129–130° C. (recrystallized from ethyl acetate-n-hexane)<br>Oxalate:<br>M.p. 122–127° C. (decomp.) |

TABLE 4-continued

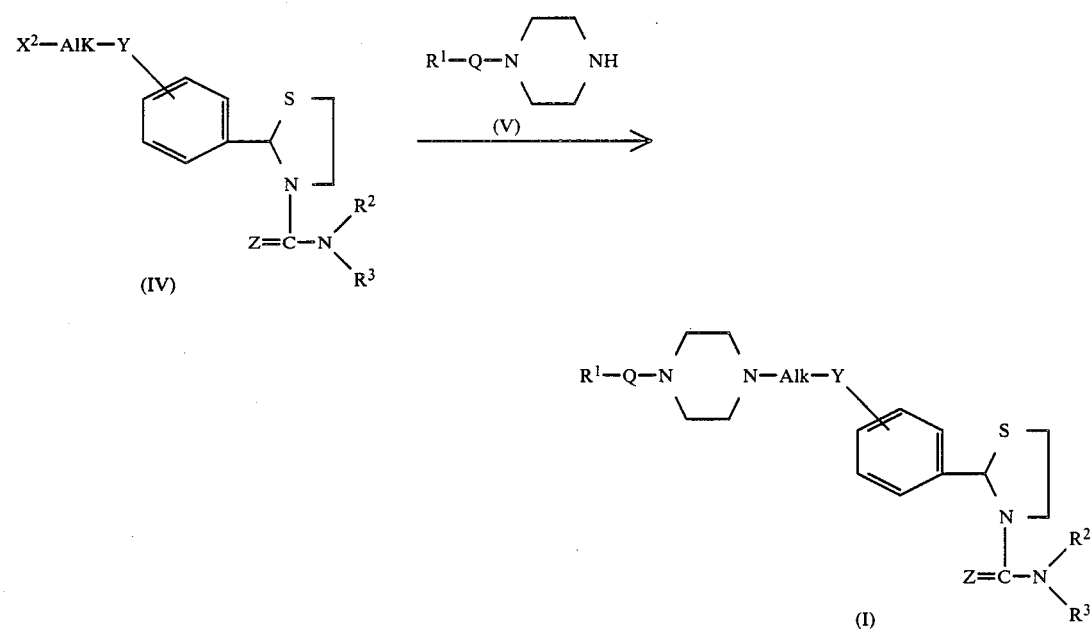

(IV)

(V)

(I)

($R^2$ = $CH_3$, $R^3$ = H, $X^2$ is Cl except that $X^2$ of Example 37 is Br)

Compound (I)

| Ex. Nos. | $R^1$ | Q and Alk | Y | position* | Z | Properties |
|---|---|---|---|---|---|---|
| 47 | 3-F-phenyl | Q = Single bond<br>Alk = —(CH$_2$)$_3$— | " | " | " | Yield: quantitative<br>oil<br>IR $\nu^{liq}_{max}$ (cm$^{-1}$): 3420, 3330, 1630<br>Oxalate:<br>M.p. 134–135° C. (decomp.)<br>(recrystallized from ethanol) |
| 48 | 2-F-phenyl | Q = Single bond<br>Alk = —(CH$_2$)$_3$— | " | " | S | Yield: 65.5%<br>M.p. 170–171.5° C. (recrystallized<br>from chloroform-methanol)<br>Fumarate:<br>M.p. 155–159° C. (decomp.)<br>(recrystallized from acetone) |
| 49 | 4-Cl-phenyl | Q = Single bond<br>Alk = —(CH$_2$)$_3$— | " | " | " | M.p. 133–136° C. (recrystallized<br>from ethanol)<br>Oxalate:<br>M.p. 108–115° C. (decomp.)<br>(recrystallized from ethanol-acetone-ether) |
| 50 | 2-CH$_3$-phenyl | Q = Single bond<br>Alk = —(CH$_2$)$_3$— | " | " | " | Yield: 60.6%<br>M.p. 119.5–121.5° C. (recrystallized<br>from ethanol-ether)<br>Fumarate:<br>M.p. 135–140° C. (recrystallized<br>from methanol-acetone-isopropyl<br>ether) |
| 51 | 3-CH$_3$-phenyl | Q = Single bond<br>Alk = —(CH$_2$)$_3$— | " | " | " | Yield: 69.7%<br>M.p. 131.5–132.5° C. (recrystallized<br>from ethanol-ether)<br>Fumarate:<br>M.p. 131.5–137° C. (decomp.)<br>(recrystallized from acetone-isopropyl<br>ether) |
| 52 | 4-CH$_3$O-phenyl | Q = Single bond<br>Alk = —(CH$_2$)$_3$— | " | " | " | M.p. 158–161° C. (recrystallized<br>from ethanol)<br>Trihydrochloride:<br>M.p. 180–186° C. (decomp.)<br>(recrystallized from methanol-ether) |
| 53 | phenyl | Q = Single bond<br>Alk = —(CH$_2$)$_3$— | S | " | " | M.p. 123–127° C. (recrystallized<br>from ethyl acetate)<br>Oxalate CH$_3$OH:<br>M.p. 124–126° C. (recrystallized<br>from methanol) |

TABLE 4-continued

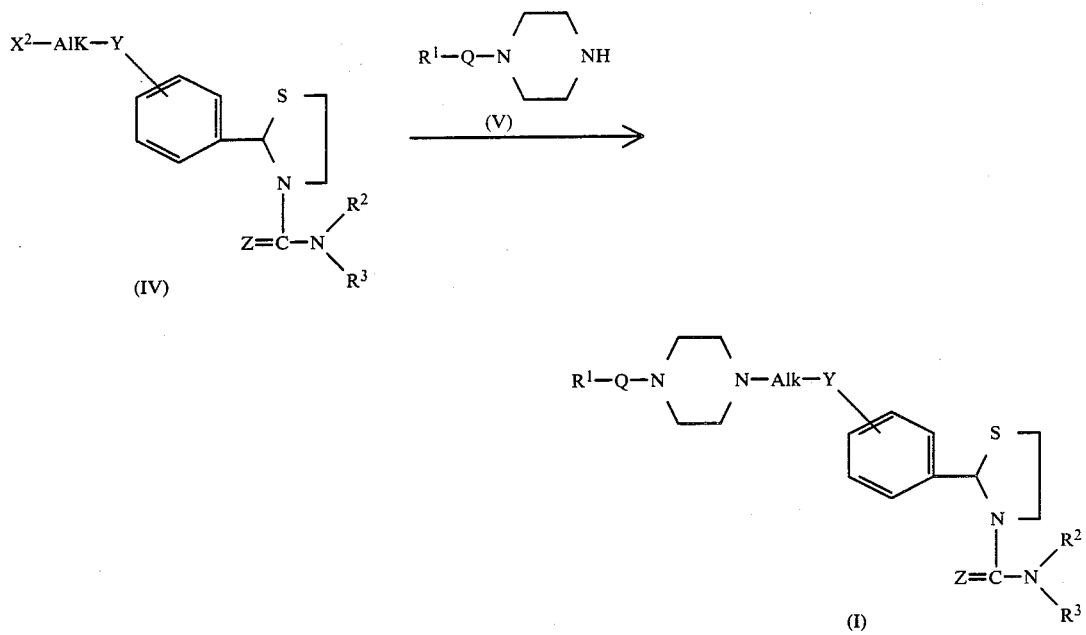

(R² = CH₃, R³ = H, X² is Cl except that X² of Example 37 is Br)

| Ex. Nos. | R¹ | Q and Alk | Y | position* | Z | Properties |
|---|---|---|---|---|---|---|
| 54 | phenyl | Q = Single bond<br>Alk = —(CH₂)₃— | " | " | O | Yield: 71%<br>M.p. 101.5–106.5° C. (recrystallized from isopropyl ether-ethanol)<br>Oxalate:<br>M.p. 129.5–135.5° C. (decomp.)<br>recrystallized from ethanol) |
| 55 | phenyl | Q = Single bond<br>Alk = —(CH₂)₄— | O | " | S | Yield: 92%<br>oil<br>Oxalate:<br>M.p. 112–115° C. (decomp.)<br>(recrystallized from methanol-acetone-ether) |

*Same as defined in the footnote of Table 3

EXAMPLE 56

1.66 g of potassium carbonate are added to a solution of 3.09 g of 2-}2-[2-(4-(3-fluorophenyl)piperazin-1-yl)ethyloxy]phenyl}thiazolidine in 40 ml of dimethylformamide, and 1.29 g of N,N-dimethylcarbamoyl chloride are added thereto. The mixture is stirred at room temperature for 2 hours and further stirred at 50° C. for 5 hours. The mixture is poured into water, and the aqueous mixture is extracted with ethyl acetate. The extract is washed with water, dried and then concentrated under reduced pressure to remove solvent. The residue is purified by silica gel chromatography (solvent, benzene:ethyl acetate:methanol=10:10:0.3), and the resultant product is recrystallized from isopropyl ether. 1.82 g of N,N-dimethyl-2-{2-[2-(4-(3-fluorophenyl)piperazin-1-yl)ethyloxy]phenyl}thiazolidine-3-carboxamide are obtained.

M.p. 90.5°–93° C.

Oxalate:

M.p. 171°–172.5° C. (decomp.) (recrystallized from acetone-ethanol-ether)

EXAMPLES 57 TO 59

The following compounds are obtained from the corresponding thiazolidine compound and carbamoyl (or thiocarbamoyl) compound in the same manner as described in Example 56.

TABLE 5

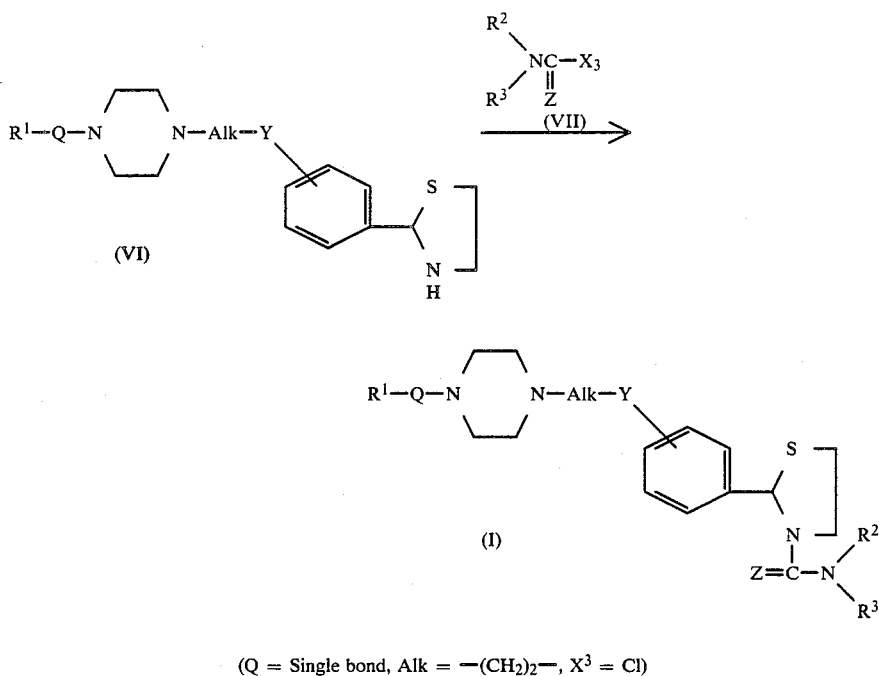

(Q = Single bond, Alk = —(CH$_2$)$_2$—, X$^3$ = Cl)

| Ex. Nos. | Compound (I) R$^1$ | Y | position* | Z | R$^2$ | R$^3$ | Properties |
|---|---|---|---|---|---|---|---|
| 57 | phenyl | O | 2 | O | CH$_3$ | CH$_3$ | Yield: 58.4%<br>M.p. 100–102° C. (recrystallized from isopropyl ether)<br>Oxalate: M.p. 167–168.5° C. (decomp.)<br>(recrystallized from acetone) |
| 58 | 3-chlorophenyl | " | " | " | " | " | Yield: quantitative<br>oil<br>Oxalate: M.p. 155–158° C. (decomp.)<br>(recrystallized from acetone) |
| 59 | phenyl | S | " | " | " | " | oil<br>IR$\nu_{max}^{liq}$ (cm$^{-1}$): 1640<br>Oxalate hemihydrate:<br>M.p. 129–135° C. (decomp.)<br>(recrystallized from methanol - ether) |

*Same as defined in the footnote of Table 3

EXAMPLE 60

A solution of 2.0 g of 2-{2-[2-(4-phenylpiperazin-1-yl)ethyloxy]phenyl}thiazolidine in 30 ml of tetrahydrofuran is added to a solution of 2.15 g of phosgene in 30 ml of toluene, and the mixture is concentrated under reduced pressure to remove solvent. 50 ml of tetrahydrofuran and a solution of 1.6 g of methylamine in 30 ml of toluene are added to the residue, respectively. The mixture is stirred at room temperature for 30 minutes, and ethyl acetate is added thereto. The mixture is washed with water, dried and concentrated under reduced pressure to remove solvent. The residue is purified by silica gel chromatography (solvent, benzene:ethyl acetate=1:5), and the resultant product is recrystallized from a mixture of ethyl acetate and n-hexane. 1.50 g of N-methyl-2-{2-[2-(4-phenylpiperazin-1-yl)ethyloxy]phenyl}thiazolidine-3-carboxamide are obtained. yield: 65%.

The physico-chemical properties of this product are identical with those of the compound obtained in Example 1.

EXAMPLE 61 TO 62

The following compounds are obtained from the corresponding thiazolidine compounds, thiophosgene and amine compounds in the same manner as described in Example 60.

TABLE 6

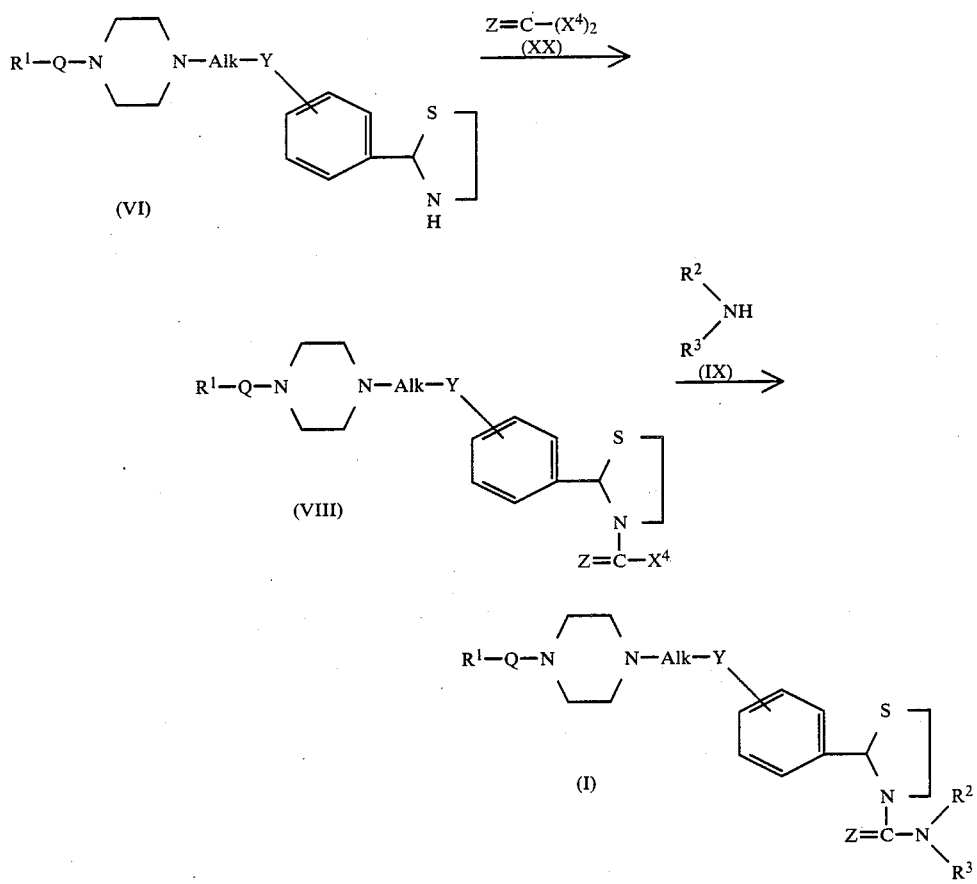

(Q = Single bond, Alk = —(CH$_2$)$_2$—, Z = S, X$^4$ = Cl)

| Ex. Nos. | R$^1$ | Y | position* | R$^2$ | R$^3$ | Properties |
|---|---|---|---|---|---|---|
| 61 | phenyl | O | 2 | CH$_3$ | CH$_3$ | oil<br>IR$\nu_{max}^{liq}$ (cm$^{-1}$): 1600, 1500<br>Mass (m/e): 456 (M$^+$)<br>Oxalate: M.p. 90–100° C. (recrystallized from acetone) |
| 62 | 3-fluorophenyl | " | " | " | " | Yield: 59.8%<br>oil<br>IR$\nu_{max}^{liq}$ (cm$^{-1}$): 1600, 1580<br>Mass (m/e): 474 (M$^+$)<br>Oxalate: M.p. 79–84° C. (recrystallized from acetone) |

*Same as defined in the footnote of Table 3

EXAMPLE 63

480 mg of (+)-N-methyl-2-{2-[2-(4-phenylpiperazin-1-yl)ethyloxy]phenyl}thiazolidine-3-carbothioamide and 339 mg of methyl trans-3-(4-methoxyphenyl)glycidate are dissolved in 40 ml of ethanol, and the solution is refluxed for 11 hours under heating. 339 mg of methyl trans-3-(4-methoxyphenyl)glycidate are added to the mixture, and the mixture is further refluxed for 3 hours. The mixture is concentrated under reduced pressure to remove solvent. The residue is purified by silica gel chromatography (solvent, chloroform:ethanol=40:1), and the resultant product is recrystallized from a mixture of ethyl acetate and n-hexane. 350 mg of (+)-N-methyl-2-{2-[2-(4-phenylpiperazin-1-yl)ethyloxy]phenyl}thiazolidine-3-carboxamide are obtained. Yield: 75.7%.

M.p. 151°–152° C.

[α]$_D^{20}$+152.4° (c=0.210, chloroform).

Oxalate ⅓ hydrate:

M.p. 170°–172° C. (decomp.) (recrystallized from acetone).

[α]$_D^{20}$+88.6° (c=0.102, methanol).

EXAMPLES 64 TO 66

The following compounds are obtained from the corresponding thiazolidine and glycidic compounds in the same manner as described in Example 63.

TABLE 7

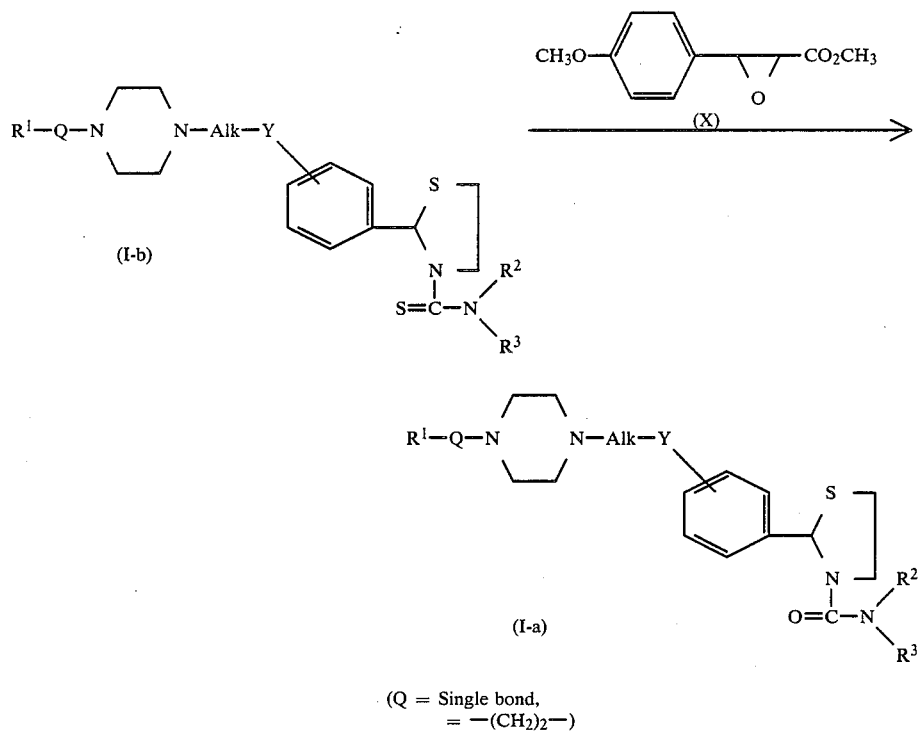

(Q = Single bond,
= —(CH$_2$)$_2$—)

| Ex. Nos. | Compound (I) R$^1$ | Y | position* | R$^2$ | R$^3$ | Properties |
|---|---|---|---|---|---|---|
| 64** | ⌬ (phenyl) | O | 2 | CH$_3$ | H | Yield: 76.7%<br>M.p. 151–152° C. (recrystallized from ethyl acetate-n-hexane)<br>[α]$_D^{20}$ - 154.1° (c = 0.231, chloroform)<br>Oxalate ⅓ hydrate: M.p. 170–172° C. (decomp.) (recrystallized from acetone)<br>[α]$_D^{20}$ - 90.9° (c = 0.130, methanol) |
| 65 | ⌬ (phenyl) | " | " | " | " | Yield: 85.7%<br>M.p. 127–129° C. (recrystallized from ethyl acetate-n-hexane)<br>Oxalate: M.p. 169.5–172.5° C. (decomp.) (recrystallized from acetone) |
| 66 | ⌬-F (fluorophenyl) | " | " | " | " | Yield: 83.3%<br>M.p. 156–157° C. (recrystallized from acetone-n-hexane)<br>Oxalate: M.p. 173–175° C. (decomp.) (recrystallized from acetone) |

*Same as defined in the footnote of Table 3
**The levororatory isomer of the compound

EXAMPLE 67

A mixture of 0.57 g of cysteamine hydrochloride, 0.21 g of sodium hydroxide and 20 ml of ethanol is stirred at room temperature for 10 minutes, and 1.55 g of 2-[2-(4-phenylpiperazin-1-yl)ethyloxy]benzaldehyde are added thereto.

The mixture is refluxed for one hour and then concentrated under reduced pressure to remove solvent. The residue is dissolved in 20 ml of tetrahydrofuran, and 0.32 g of methyl isocyanate is added thereto. The mixture is stirred at room temperature for 2 hours and then concentrated under reduced pressure to remove solvent. Water is added to the residue, and the aqueous mixture is extracted with ethyl acetate. The extract is washed with water, dried and then concentrated under reduced pressure to remove solvent. The residue is recrystallized from a mixture of ethyl acetate and n-hexane. 1.70 g of N-methyl-2-{2-[2-(4-phenylpiperazin-1-yl)ethyloxy]phenyl}thiazolidine-3-carboxamide are obtained. Yield: 79.8%.

The physico-chemical properties of this produce are identical with those of the compound obtained in Example 1.

EXAMPLES 68 to 122

The following compounds are obtained from the corresponding aldehyde compounds, cysteamine and isocyanate (or isothiocyanate) compounds in the same manner as described in Example 67.

TABLE 8

($R^2 = CH_3$)

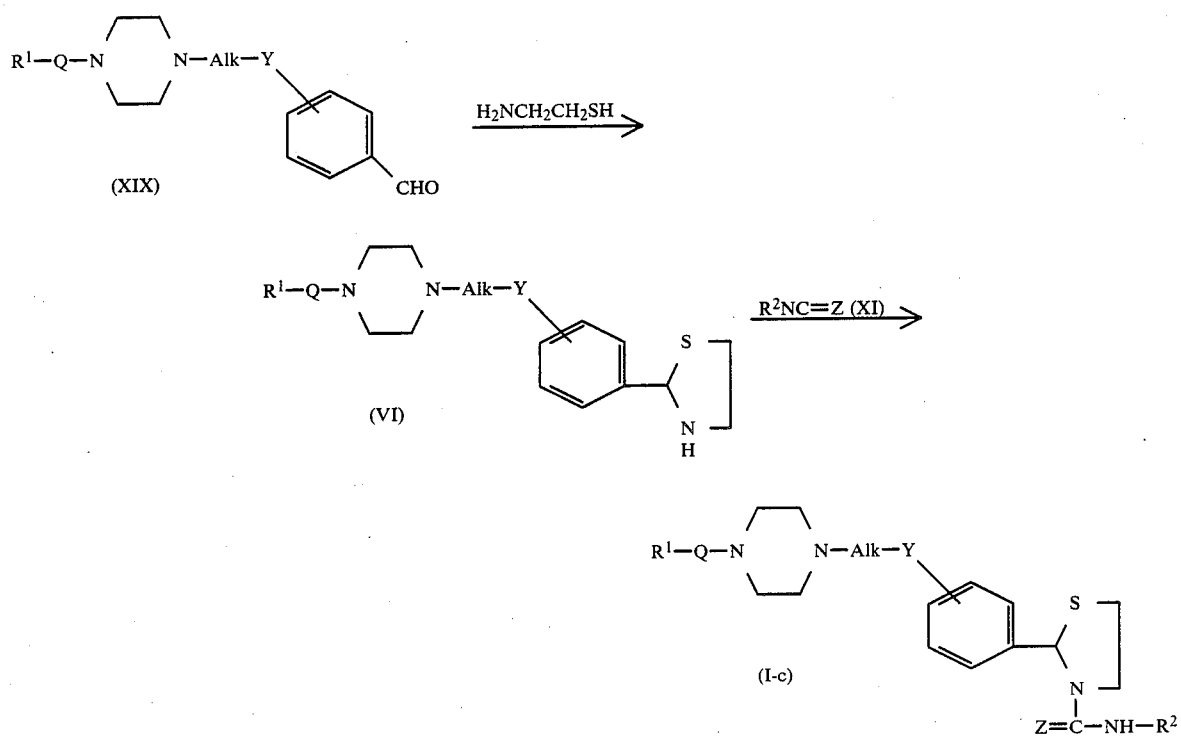

| Ex. Nos. | $R^1$ | Q and Alk | Y | position* | Z | Properties |
|---|---|---|---|---|---|---|
| 68 | phenyl | Q = Single bond<br>Alk = —(CH$_2$)$_2$— | O | 2 | S | Yield: 72%<br>M.p. 124–126° C. (recrystallized from ethyl acetate-n-hexane)<br>Fumarate:<br>M.p. 166–168° C. (decomp.)<br>(recrystallized from acetone-ethanol) |
| 69 | 3-F-phenyl | Q = Single bond<br>Alk = —(CH$_2$)$_2$— | " | " | " | M.p. 138–139.5° C. (recrystallized from ethyl acetate-n-hexane)<br>Fumarate:<br>M.p. 162–164° C. (decomp.)<br>(recrysatllized from acetone-methanol) |
| 70 | 2-F-phenyl | Q = Single bond<br>Alk = —(CH$_2$)$_2$— | " | " | " | Yield: 70%<br>M.p. 143–145° C. (recrystallized from ethyl acetate-n-hexane)<br>Fumarate:<br>M.p. 178–179° C. (decomp.)<br>(recrystallized from methanol-ether) |
| 71 | 4-F-phenyl | Q = Single bond<br>Alk = —(CH$_2$)$_2$— | " | " | " | Yield: 65%<br>M.p. 132–133° C. (recrystallized from ethyl acetate-n-hexane)<br>Fumarate:<br>M.p. 163–164° C. (decomp.)<br>(recrystallized from methanol-acetone-n-hexane) |
| 72 | 2-Cl-phenyl | Q = Single bond<br>Alk = —(CH$_2$)$_2$— | " | " | " | Yield: 79%<br>M.p. 145–151° C. (recrystallized from ethyl acetate-n-hexane)<br>Fumarate:<br>M.p. 180–181° C. (decomp.)<br>(recrystallized from methanol-acetone-n-hexane) |

TABLE 8-continued ($R^2 = CH_3$)

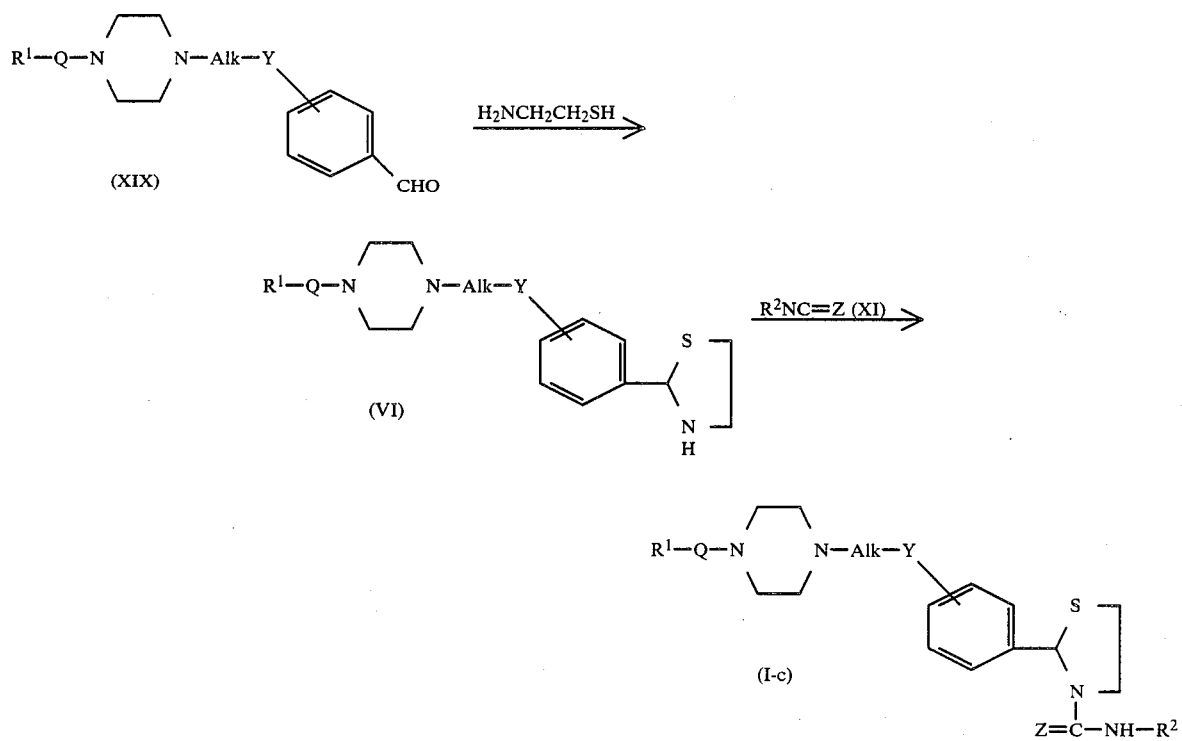

| Ex. Nos. | $R^1$ | Q and Alk | Y | position* | Z | Properties |
|---|---|---|---|---|---|---|
| 73 | 3-Cl-C6H4 | Q = Single bond<br>Alk = —(CH$_2$)$_2$— | " | " | " | Yield: 58%<br>M.p. 147–148° C. (recrystallized from ethyl acetate-n-hexane)<br>Fumarate:<br>M.p. 151–153° C. (decomp.)<br>(recrystallized from methanol-ether) |
| 74 | 4-Cl-C6H4 | Q = Single bond<br>Alk = —(CH$_2$)$_2$— | " | " | " | Yield: 52%<br>M.p. 130–133° C. (recrystallized from ethyl acetate-n-hexane)<br>Fumarate:<br>M.p. 155–160° C. (decomp.)<br>(recrystallized from acetone-ether) |
| 75 | 2-CH3-C6H4 | Q = Single bond<br>Alk = —(CH$_2$)$_2$— | " | " | " | Yield: 68%<br>M.p. 171–174° C. (recrystallized from ethyl acetate-ethanol)<br>Fumarate:<br>M.p. 186–188° C. (decomp.)<br>(recrystallized from acetone) |
| 76 | 3-CH3-C6H4 | Q = Single bond<br>Alk = —(CH$_2$)$_2$— | " | " | " | M.p. 132–136° C. (recrystallized from ethanol)<br>Fumarate hemihydrate:<br>M.p. 157–160° C. (decomp.)<br>(recrystallized from acetone) |
| 77 | 4-CH3-C6H4 | Q = Single bond<br>Alk = —(CH$_2$)$_2$— | " | " | " | Yield: 71%<br>M.p. 157–160° C. (recrystallized from ethanol)<br>½ Fumarate hemihydrate:<br>M.p. 170–171.5° C. (decomp.)<br>(recrystallized from ethanol) |

TABLE 8-continued ($R^2 = CH_3$)

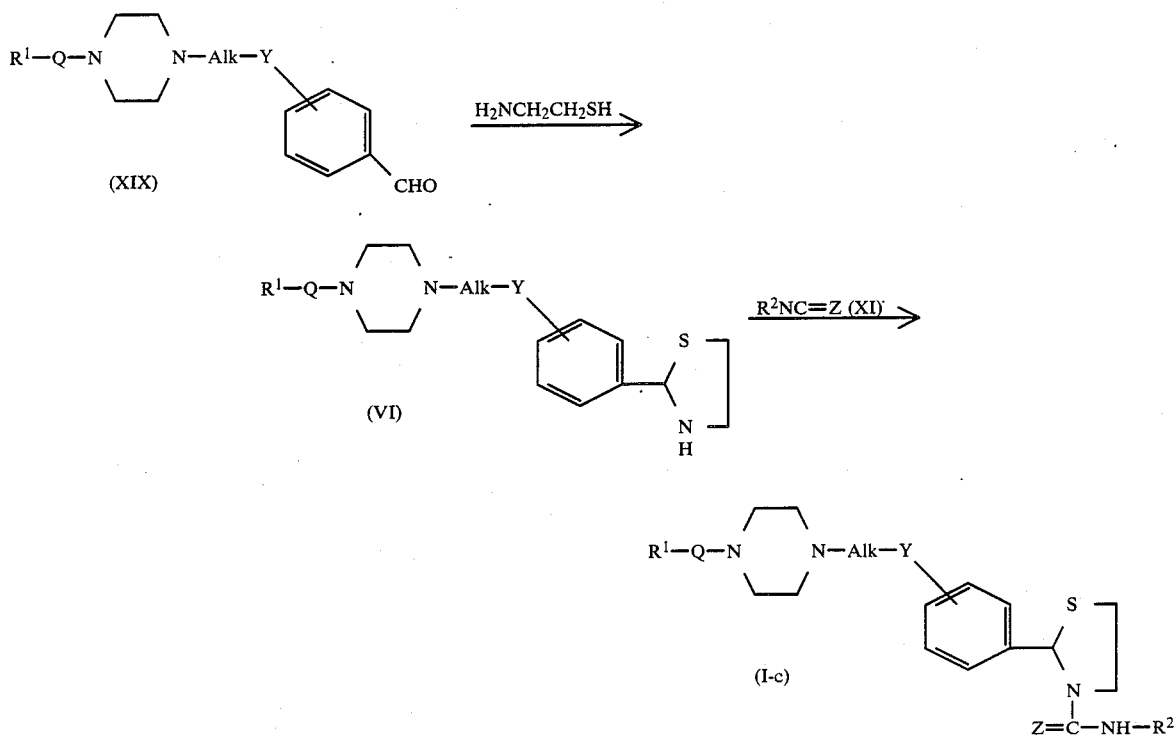

| Ex. Nos. | $R^1$ | Q and Alk | Y | position* | Z | Properties |
|---|---|---|---|---|---|---|
| 78 | 2-OCH₃-phenyl | Q = Single bond<br>Alk = —(CH₂)₂— | " | " | " | Yield: 86%<br>M.p. 161–162.5° C. (recrystallized from ethyl acetate-n-hexane)<br>Fumarate monohydrate:<br>M.p. 181–183° C. (decomp.)<br>(recrystallized from methanol-acetone-n-hexane) |
| 79 | 3-OCH₃-phenyl | Q = Single bond<br>Alk = —(CH₂)₂— | " | " | " | Yield: 50%<br>M.p. 135–138° C. (recrystallized from isopropyl ether-ethanol)<br>Fumarate:<br>M.p. 155–159° C. (decomp.)<br>(recrystallized from isopropyl ether-ethanol) |
| 80 | 4-CH₃O-phenyl | Q = Single bond<br>Alk = —(CH₂)₂— | " | " | " | Yield: 55%<br>M.p. 135–137° C. (recrystallized from ethyl acetate-n-hexane)<br>Fumarate:<br>M.p. 155–160° C. (decomp.) |
| 81 | 3-CH₃S-phenyl | Q = Single bond<br>Alk = —(CH₂)₂— | " | " | " | Yield: 86%<br>M.p. 126–128° C. (recrystallized from ethanol)<br>Fumarate:<br>M.p. 158–160° C. (decomp.)<br>(recrystallized from acetone) |
| 82 | 4-CH₃S-phenyl | Q = Single bond<br>Alk = —(CH₂)₂— | " | " | " | Yield: 62%<br>M.p. 125–129° C. (recrystallized from ethanol)<br>Dihydrochloride:<br>M.p. 182–187° C. (decomp.)<br>(recrystallized from ethanol) |

TABLE 8-continued ($R^2 = CH_3$)

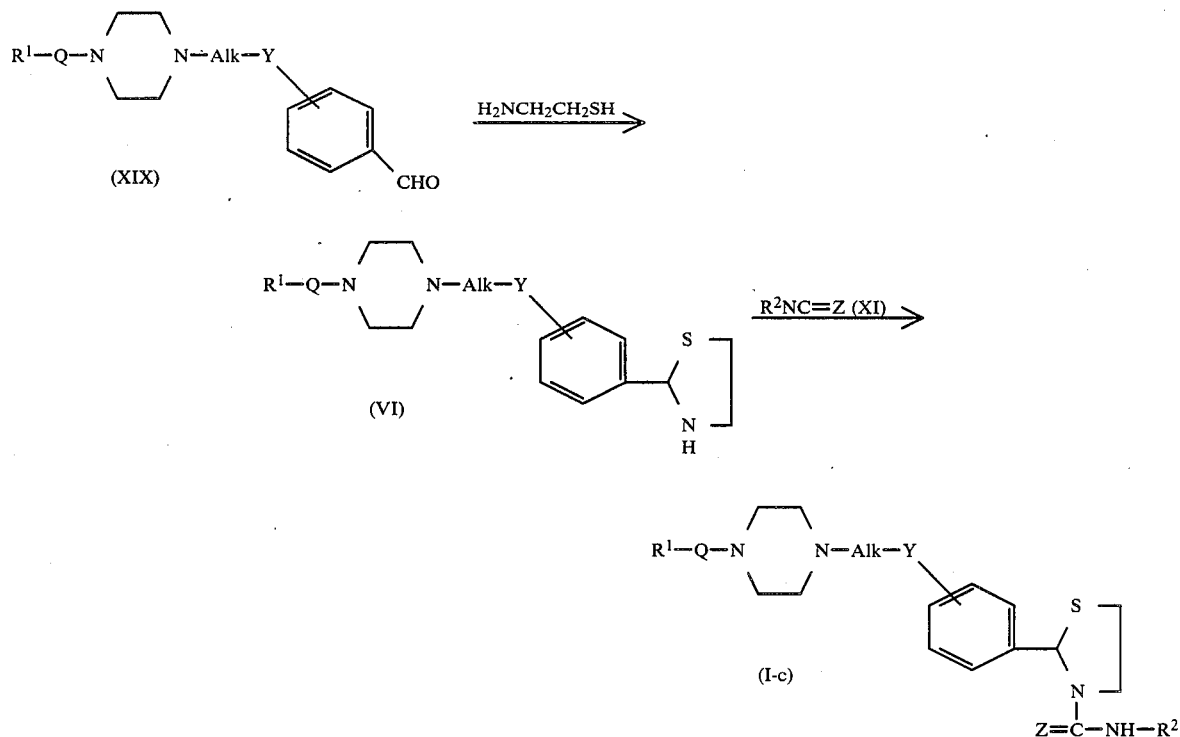

| Ex. Nos. | $R^1$ | Q and Alk | Y | position* | Z | Properties |
|---|---|---|---|---|---|---|
| 83 | $NO_2$-C6H4- | Q = Single bond<br>Alk = $-(CH_2)_2-$ | " | " | " | Yield: 80%<br>M.p. 116-119° C. (recrystallized from chloroform-ethyl acetate-n-hexane)<br>Hydrochloride:<br>M.p. 218-220° C. (decomp.)<br>(recrystallized from dimethyl-formamide-ethyl acetate) |
| 84 | C6H5- | Q = Single bond<br>Alk = $-(CH_2)_3-$ | " | " | " | Yield: 93.2%<br>M.p. 120-123° C. (recrystallized from ethyl acetate-n-hexane)<br>Fumarate:<br>M.p. 125-128° C. (decomp.)<br>(recrystallized from ethanol-ether) |
| 85 | 2-F-C6H4- | Q = Single bond<br>Alk = $-(CH_2)_3-$ | " | " | " | Yield: 71%<br>M.p. 116-118° C. (recrystallized from ether-ethyl acetate-n-hexane)<br>Fumarate:<br>M.p. 138-140° C. (decomp.)<br>(recrystallized from acetone-n-hexane) |
| 86 | 3-F-C6H4- | Q = Single bond<br>Alk = $-(CH_2)_3-$ | " | " | " | Yield: 85%<br>M.p. 133-134° C. (recrystallized from ethanol-water)<br>Fumarate:<br>M.p. 147-148° C. (decomp.)<br>(recrystallized from acetone-n-hexane) |
| 87 | 4-F-C6H4- | Q = Single bond<br>Alk = $-(CH_2)_3-$ | " | " | " | Yield: 77.6%<br>M.p. 113-116° C. (recrystallized from ethyl acetate-n-hexane)<br>Fumarate:<br>M.p. 115-118° C. (decomp.)<br>(recrystallized from acetone-ethanol-ether) |

TABLE 8-continued ($R^2 = CH_3$)

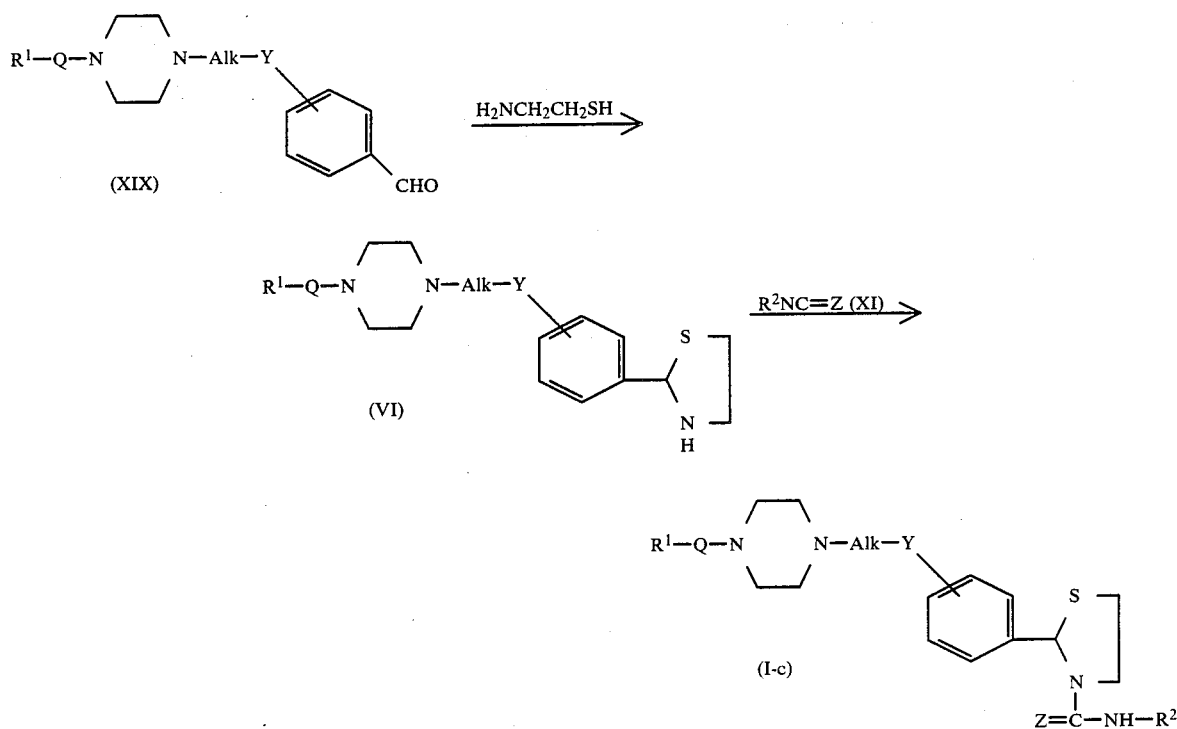

| Ex. Nos. | $R^1$ | Q and Alk | Y | position* | Z | Properties |
|---|---|---|---|---|---|---|
| 88 | 2-Cl-phenyl | Q = Single bond<br>Alk = —(CH$_2$)$_3$— | " | " | " | Yield: 86%<br>M.p. 111–116° C. (recrystallized from ethyl acetate-n-hexane)<br>Fumarate:<br>M.p. 149–151.5° C. (decomp.)<br>(recrystallized from acetone-n-hexane) |
| 89 | 3-Cl-phenyl | Q = Single bond<br>Alk = —(CH$_2$)$_3$— | " | " | " | Yield: 81%<br>M.p. 149–152° C. (recrystallized from ethyl acetate-n-hexane)<br>Fumarate:<br>M.p. 143.5–145° C. (decomp.)<br>(recrystallized from acetone-n-hexane) |
| 90 | 4-Cl-phenyl | Q = Single bond<br>Alk = —(CH$_2$)$_3$— | " | " | " | Yield: 65%<br>M.p. 126–130° C. (recrystallized from ethyl acetate-n-hexane)<br>Fumarate:<br>M.p. 133–138° C. (decomp.)<br>(recrystallized from ethanol-ether) |
| 91 | 2-CH$_3$-phenyl | Q = Single bond<br>Alk = —(CH$_2$)$_3$— | " | " | " | Yield: 91%<br>M.p. 110–112° C. (recrystallized from ethyl acetate-n-hexane)<br>Fumarate:<br>M.p. 162–164° C. (decomp.)<br>(recrystallized from acetone-n-hexane) |
| 92 | 3,5-di-CH$_3$-phenyl | Q = Single bond<br>Alk = —(CH$_2$)$_3$— | " | " | " | Yield: 91%<br>M.p. 140–141.5° C. (recrystallized from ethanol-water)<br>Fumarate:<br>M.p. 140–142° C. (decomp.)<br>(recrystallized from acetone-n-hexane) |

TABLE 8-continued (R² = CH₃)

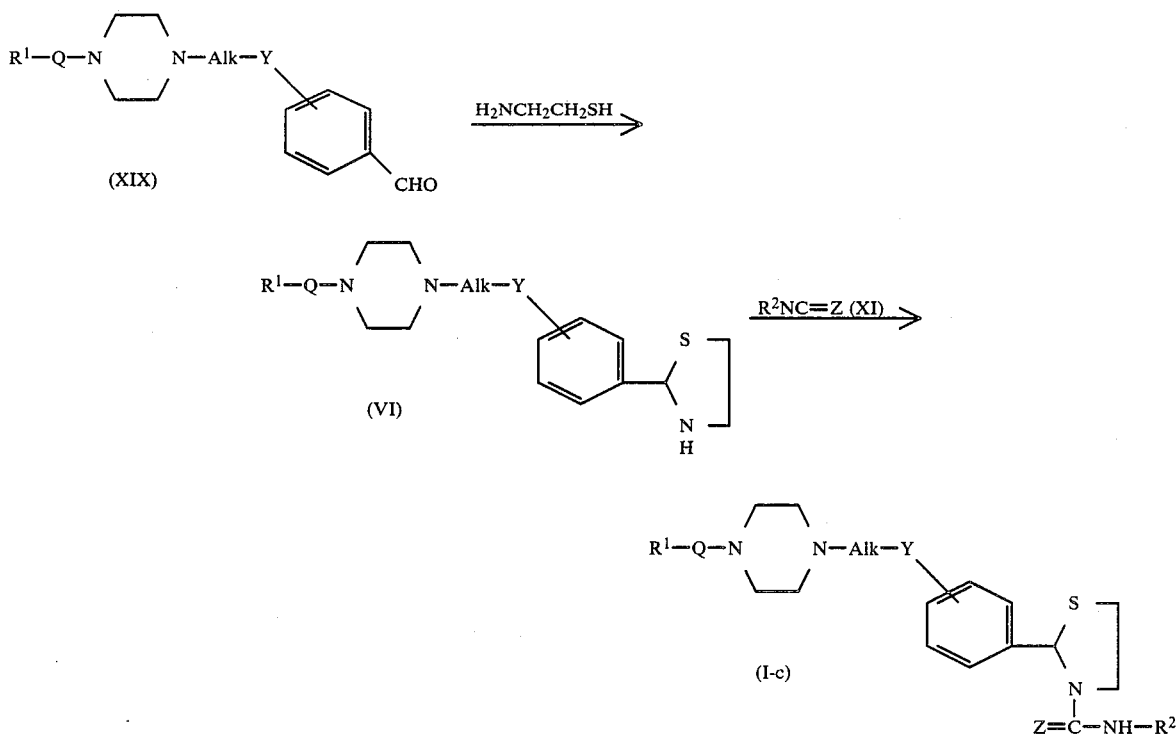

| Ex. Nos. | R¹ | Q and Alk | Y | position* | Z | Properties |
|---|---|---|---|---|---|---|
| 93 | CH₃-〔phenyl〕- | Q = Single bond<br>Alk = —(CH₂)₃— | " | " | " | Yield: 83.9%<br>M.p. 163–165° C. (recrystallized from ethanol)<br>Fumarate:<br>M.p. 135–138° C. (decomp.)<br>(recrystallized from ethanol-acetone-ether) |
| 94 | 〔phenyl-OCH₃〕- | Q = Single bond<br>Alk = —(CH₂)₃— | " | " | " | Yield: 69%<br>M.p. 110–115° C. (recrystallized from ethyl acetate-n-hexane)<br>Fumarate:<br>M.p. 159–161° C. (decomp.)<br>(recrystallized from acetone-n-hexane) |
| 95 | 〔phenyl-OCH₃〕- | Q = Single bond<br>Alk = —(CH₂)₃— | " | " | " | Yield: 63%<br>M.p. 149–154° C.<br>Oxalate:<br>M.p. 154–157° C. (decomp.)<br>(recrystallized from ethanol-methanol) |
| 96 | CH₃O-〔phenyl〕- | Q = Single bond<br>Alk = —(CH₂)₃— | " | " | " | Yield: 83%<br>M.p. 158–161° C. (recrystallized from ethyl acetate-n-hexane)<br>Fumarate:<br>M.p. 129–132° C. (decomp.)<br>(recrystallized from ethanol-acetone) |
| 97 | 〔phenyl-SCH₃〕- | Q = Single bond<br>Alk = —(CH₂)₃— | " | " | " | Yield: 65.4%<br>M.p. 135–139° C. (recrystallized from ethanol-n-hexane)<br>Fumarate:<br>M.p. 125–130° C. (decomp.)<br>(recrystallized from acetone-n-hexane) |

TABLE 8-continued ($R^2 = CH_3$)

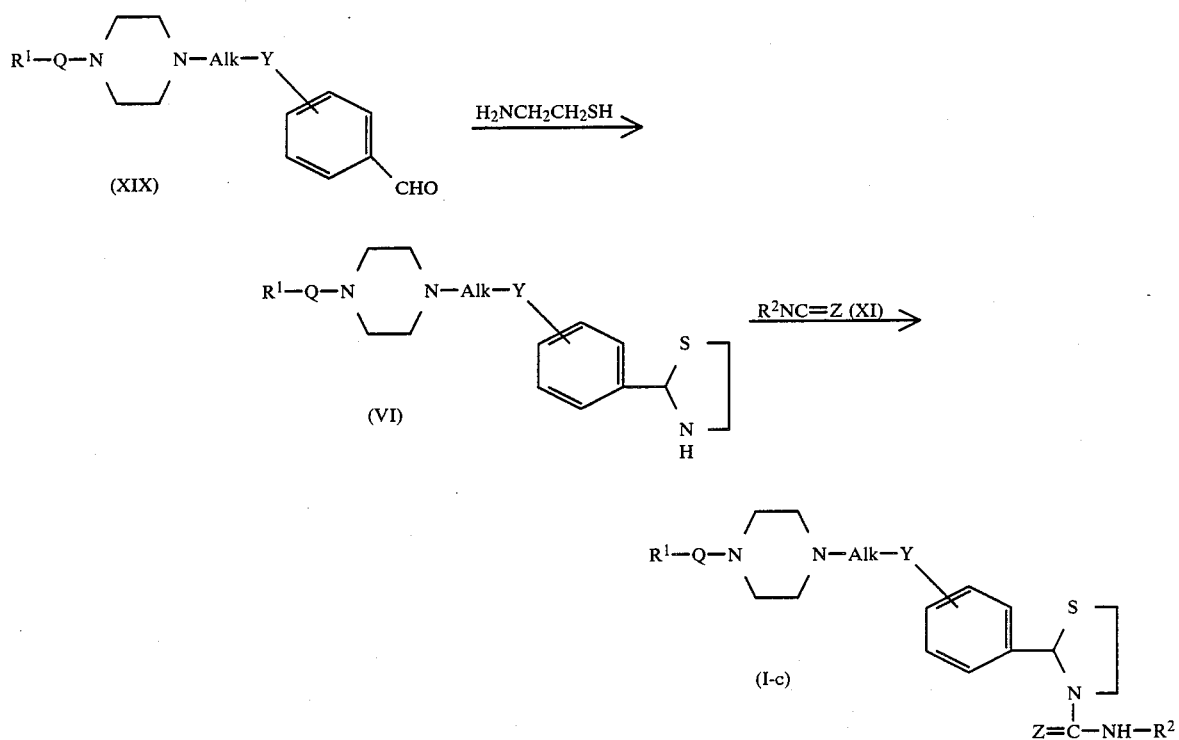

| Ex. Nos. | $R^1$ | Q and Alk | Y | position* | Z | Properties |
|---|---|---|---|---|---|---|
| 98 | CH₃S—C₆H₄— | Q = Single bond<br>Alk = —(CH₂)₃— | " | " | " | Yield: 78%<br>M.p. 160–161° C. (recrystallized from chloroform-ethanol)<br>Fumarate:<br>M.p. 135–137° C. (decomp.)<br>(recrystallized from acetone) |
| 99 | NO₂—C₆H₄— | Q = Single bond<br>Alk = —(CH₂)₃— | " | " | " | Yield: 77%<br>M.p. 191–193° C. (recrystallized from chloroform-ethyl acetate-n-hexane)<br>Oxalate:<br>M.p. 197–199° C. (decomp.)<br>(recrystallized from methanol-ether) |
| 100 | C₆H₅— | Q = Single bond<br>Alk = —(CH₂)₃— | S | " | " | Yield: 70%<br>M.p. 110–114° C. (recrystallized from ethyl acetate-n-hexane)<br>Oxalate C₂H₅OH:<br>M.p. 131–141° C. (decomp.)<br>(recrystallized from ethanol-methanol-ether) |
| 101 | 3-F-C₆H₄— | Q = Single bond<br>Alk = —(CH₂)₄— | O | " | O | Yield: 53%<br>M.p. 127–129° C. (recrystallized from ethyl acetate-n-hexane)<br>Oxalate:<br>M.p. 179.5–180.5° C. (decomp.)<br>(recrystallized from water-acetone-n-hexane) |
| 102 | 3-F-C₆H₄— | Q = Single bond<br>Alk = —(CH₂)₄— | " | " | S | Yield: 53%<br>M.p. 72–74° C. (recrystallized from ether-n-hexane)<br>Fumarate:<br>M.p. 165–167° C. (decomp.)<br>(recrystallized from acetone-n-hexane) |

TABLE 8-continued ($R^2$ = $CH_3$)

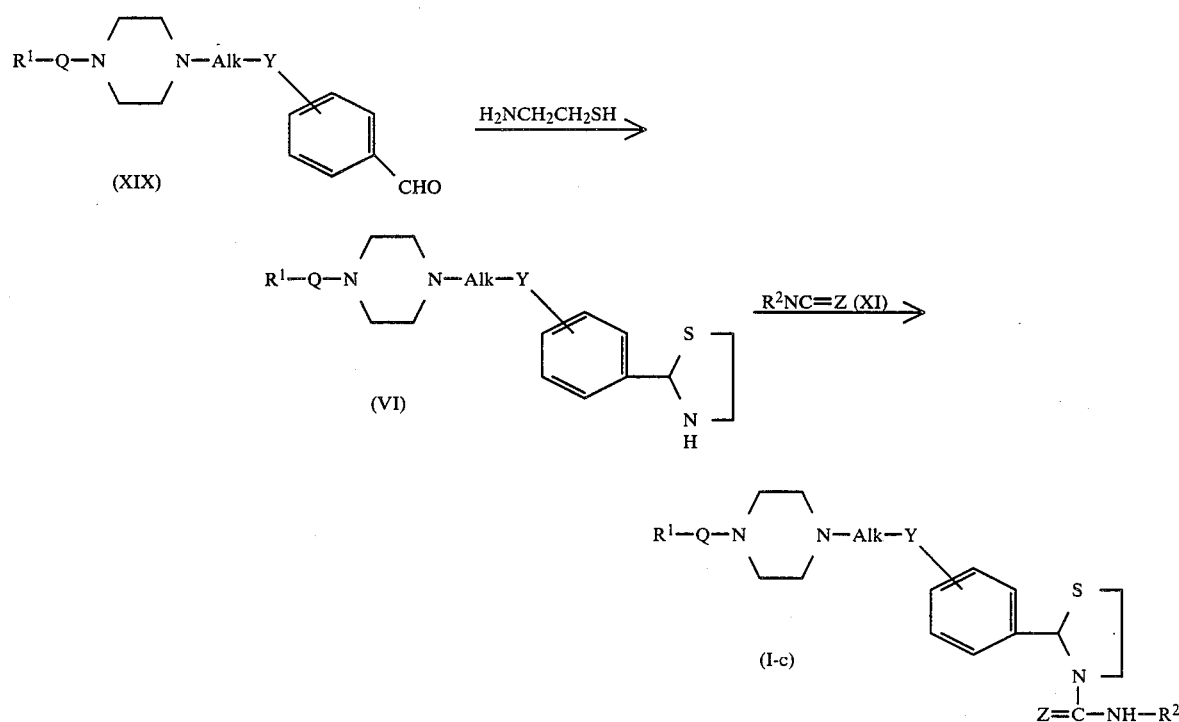

| Ex. Nos. | $R^1$ | Q and Alk | Y | position* | Z | Properties |
|---|---|---|---|---|---|---|
| 103 | 2-F-phenyl | Q = Single bond<br>Alk = —(CH$_2$)$_4$— | " | " | " | Yield: 75.2%<br>M.p. 104–106° C. (recrystallized from ethyl acetate-n-hexane)<br>Oxalate:<br>M.p. 153–156° C. (decomp.)<br>(recrystallized from acetone) |
| 104 | 4-CH$_3$-phenyl | Q = Single bond<br>Alk = —(CH$_2$)$_4$— | " | " | " | Yield: 63.5%<br>M.p. 132–135° C. (recrystallized from ethanol)<br>Oxalate:<br>M.p. 143–148° C. (decomp.)<br>(recrystallized from methanol-ethanol) |
| 105 | 4-CH$_3$O-phenyl | Q = Single bond<br>Alk = —(CH$_2$)$_4$— | " | " | " | Yield: 76.5%<br>M.p. 113–116° C. (recrystallized from ethanol)<br>Oxalate:<br>M.p. 172–176° C. (decomp.) |
| 106 | 4-CH$_3$S-phenyl | Q = Single bond<br>Alk = —(CH$_2$)$_4$— | " | " | " | Yield: 76.5%<br>M.p. 124–127.5° C. (recrystallized from ethyl acetate-n-hexane)<br>Fumarate:<br>M.p. 127–131° C. (decomp.)<br>(recrystallized from acetone) |
| 107 | 4-NO$_2$-phenyl | Q = Single bond<br>Alk = —(CH$_2$)$_4$— | " | " | " | Yield: 59.1%<br>M.p. 158–161° C. (recrystallized from chloroform-methanol)<br>Fumarate:<br>M.p. 144–148° C. (decomp.)<br>(recrystallized from acetone-ether) |
| 108 | phenyl | Q = Single bond<br>Alk = —(CH$_2$)$_5$— | " | " | " | M.p. 121.5–123.5° C. (recrystallized from isopropyl alcohol-isopropyl ether)<br>Oxalate:<br>M.p. 173–175° C. (decomp.)<br>(recrystallized from methanol-ethanol-ether) |

TABLE 8-continued ($R^2 = CH_3$)

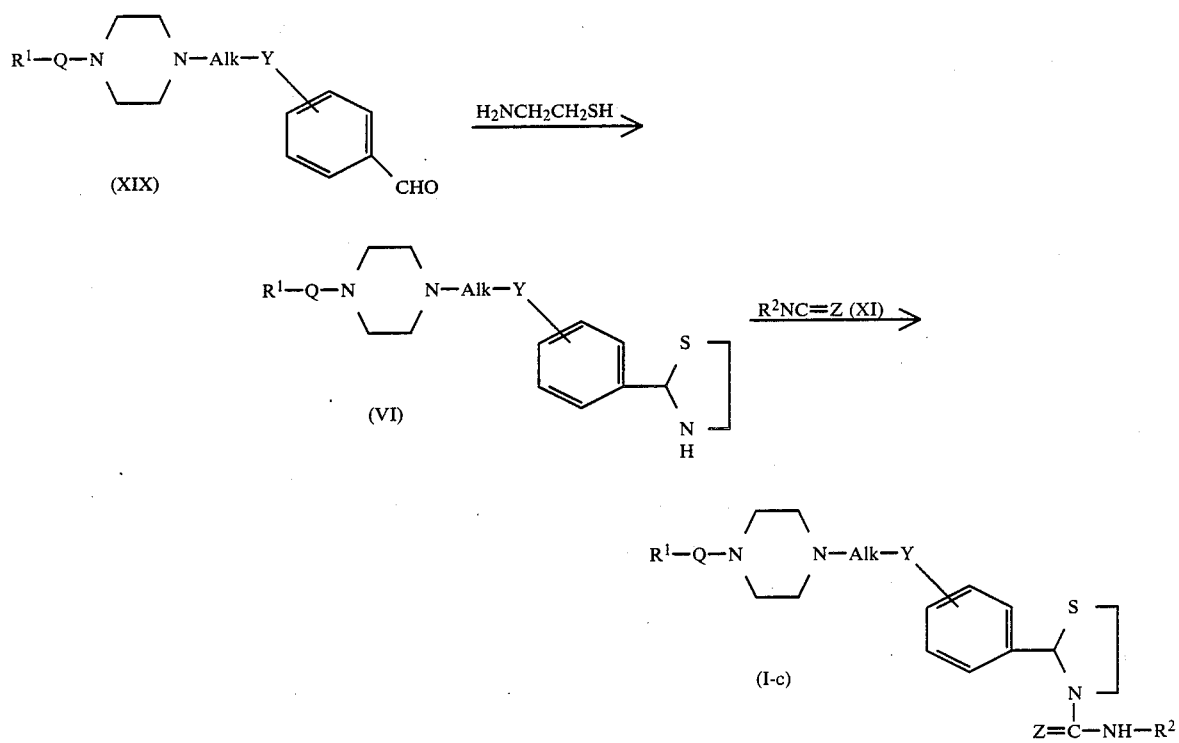

| Ex. Nos. | $R^1$ | Q and Alk | Y | position* | Z | Properties |
|---|---|---|---|---|---|---|
| 109 | CH₃O—⟨phenyl⟩— | Q = Single bond<br>Alk = —(CH₂)₅— | " | " | " | Yield: 69.6%<br>M.p. 138–139° C. (recrystallized from ethanol)<br>Dioxalate:<br>M.p. 170–173° C. (decomp.)<br>(recrystallized from methanol) |
| 110 | ⟨phenyl⟩ | Q = Single bond<br>Alk = —(CH₂)₂— | " | " | " | M.p. 132–134° C. (recrystallized from ethanol-ethyl-acetate-n-hexane)<br>Dihydrochloride hemihydrate:<br>M.p. 199–201° C. (decomp.)<br>(recrystallized from methanol-ethanol-isopropyl alcohol) |
| 111 | ⟨phenyl⟩ | Q = Single bond<br>Alk = —(CH₂)₃— | " | " | " | M.p. 88–96° C. (recrystallized from ethyl acetate-n-hexane)<br>Difumarate:<br>M.p. 182.5–184.5° C. (decomp.)<br>(recrystallized from isopropyl ether-ethanol) |
| 112 | ⟨phenyl⟩ | Q = —CH=CHCH₂—<br>Alk = —(CH₂)₃— | " | " | " | Yield: 66.3%<br>M.p. 101.5–103° C. (recrystallized from ethyl acetate-n-hexane)<br>Trihydrochloride:<br>M.p. 201–203.5° C. (decomp.)<br>(recrystallized from methanol-ether) |
| 113 | ⟨phenyl⟩ | Q = Single bond<br>Alk = —(CH₂)₃— | " | 3 | " | Yield: 72%<br>oil<br>Fumarate:<br>M.p. 144–148° C. (decomp.)<br>(recrystallized from acetone-ethanol-ether) |

TABLE 8-continued ($R^2$ = $CH_3$)

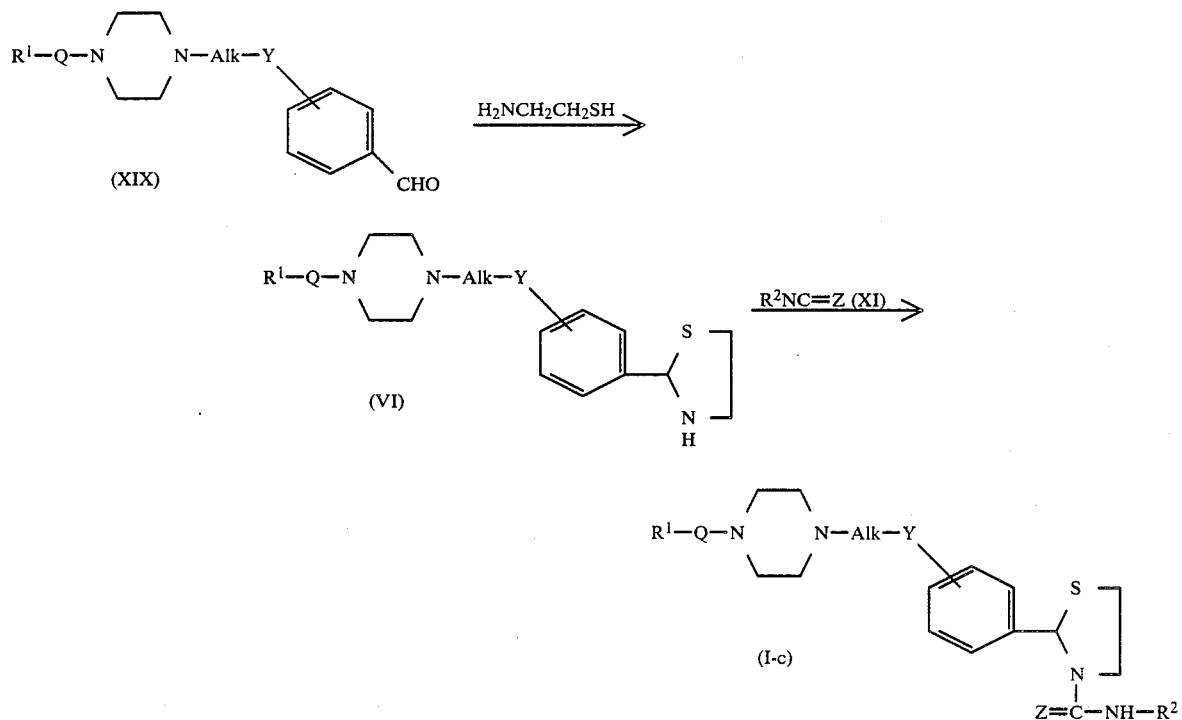

| Ex. Nos. | $R^1$ | Q and Alk | Y | position* | Z | Properties |
|---|---|---|---|---|---|---|
| 114 | phenyl | Q = Single bond<br>Alk = —(CH$_2$)$_3$— | " | 4 | " | Yield: 69%<br>M.p. 146–149° C. (recrystallized from isopropyl alcohol)<br>Oxalate:<br>M.p. 115–120° C. (decomp.)<br>(recrystallized from methanol-ether) |

*Same as defined in the footnote of Table 3

TABLE 9

(Q = Single bond, Alk = —(CH$_2$)$_2$— (Example Nos. 115–120),
or —(CH$_2$)$_3$— (Example Nos. 121–122))

| Ex. Nos. | $R^1$ | Y | position* | Z | $R^2$ | Properties |
|---|---|---|---|---|---|---|
| 115 | 3-F-phenyl | O | 2 | O | $C_2H_5$ | Yield: 75.2%<br>M.p. 116–118° C. (recrystallized from ethyl acetate-n-hexane)<br>Oxalate:<br>M.p. 197–198° C. (decomp.)<br>(recrystallized from water-acetone-ether) |
| 116 | 3-F-phenyl | " | " | " | n-$C_4H_9$ | Yield: 70.7%<br>M.p. 93–95.5° C. (recrystallized from isopropyl ether-n-hexane)<br>Fumarate:<br>M.p. 165–167° C. (decomp.)<br>(recrystallized from ethanol-isopropyl ether) |
| 117 | phenyl | " | " | S | cyclohexyl | Yield: 51.1%<br>M.p. 131–134° C. (recrystallized from ethyl acetate-n-hexane)<br>Oxalate monohydrate:<br>M.p. 162–164° C. (decomp.)<br>(recrystallized from methanol-ether) |

TABLE 9-continued (Q = Single bond, Alk = —(CH$_2$)$_2$— (Example Nos. 115–120), or —(CH$_2$)$_3$— (Example Nos. 121–122))

| Ex. Nos. | R$^1$ | Y | position* | Z | R$^2$ | Properties |
|---|---|---|---|---|---|---|
| 118 | 3-F-C$_6$H$_4$ | " | " | " | C$_2$H$_5$ | Yield: 97.2%<br>oil<br>Oxalate:<br>M.p. 148–151° C. (decomp.)<br>(recrystallized from acetone) |
| 119 | 3-F-C$_6$H$_4$ | " | " | " | n-C$_4$H$_9$ | Yield: 94.3%<br>oil<br>Fumarate hemihydrate:<br>M.p. 168–170.5° C. (decomp.)<br>(recrystallized from acetone-n-hexane) |
| 120 | 3-F-C$_6$H$_4$ | " | " | " | C$_6$H$_5$ | Yield: 61.7%<br>M.p. 124–126° C. (recrystallized from ethyl acetate-n-hexane)<br>Fumarate:<br>M.p. 161.5–164° C. (decomp.)<br>(recrystallized from ethanol-methanol) |
| 121 | 3-F-C$_6$H$_4$ | " | " | " | C$_2$H$_5$ | Yield: 98.6%<br>pale yellow caramel<br>Oxalate:<br>M.p. 176–178° C. (decomp.)<br>(recrystallized from acetone) |
| 122 | 3-F-C$_6$H$_4$ | " | " | " | n-C$_4$H$_9$ | Yield: 97.1%<br>pale yellow oil<br>Oxalate:<br>M.p. 177.5–178.5° C. (decomp.)<br>(recrystallized from acetone) |

*Same as defined in the footnote of Table 3

EXAMPLE 123

3.69 g of 2-{2-[2-(4-phenylpiperazin-1-yl)ethyloxy]phenyl}thiazolidine are dissolved in 40 ml of tetrahydrofuran, and 0.62 g of methyl isocyanate is added thereto at room temperature. The mixture is stirred at the same temperature for 2 hours. The mixture is concentrated under reduced pressure to remove solvent. Water is added to the residue, and crystalline precipitates are collected by filtration. The crystals are washed with ethanol and ether, and then recrystallized from a mixture of ethyl acetate and n-hexane. 3.82 g of N-methyl-2-{2-[2-(4-phenylpiperazin-1-yl)ethyloxy]phenyl}thiazolidin-3-carboxamide are obtained. Yield: 89.7%.

The physico-chemical properties of this product are identical with those of the product obtained in Example 1.

EXAMPLES 124 TO 131

The following compounds are obtained from the corresponding thiazolidine and isocyanate (or isothiocyanate) compounds in the same manner as described in Example 123.

TABLE 10

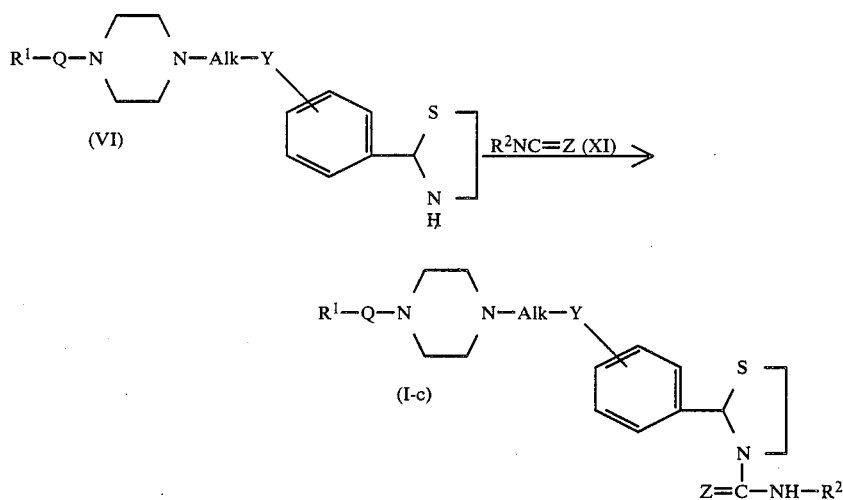

(Q = Single bond, Alk = —(CH$_2$)$_2$—)

| Ex. Nos. | R$^1$ | Y | position* | Z | R$^2$ | Properties |
|---|---|---|---|---|---|---|
| 124 | 3-F-C$_6$H$_4$ | O | 2 | O | CH$_3$ | Yield: 89.5% <br> M.p. 156–157° C. (recrystallized from acetone-n-hexane) <br> Oxalate: <br> M.p. 173–175° C. (decomp.) <br> (recrystallized from acetone) |
| 125 | C$_6$H$_5$ | " | " | S | CH$_3$CO | Yield: 56.4% <br> M.p. 139–140.5° C. (recrystallized from ethyl acetate-n-hexane) <br> Oxalate: <br> M.p. 156–157° C. (decomp.) <br> (recrystallized from acetone) |
| 126 | C$_6$H$_5$ | S | 2 | O | CH$_3$CO | Yield: 89.6% <br> oil <br> IR$\lambda_{max}^{CHCl_3}$ (cm$^{-1}$): 1710, 1690 <br> Oxalate: <br> M.p. 116–120° C. (decomp.) <br> (recrystallized from acetone) |
| 127 | 3-F-C$_6$H$_4$ | O | " | S | " | M.p. 151–152° C. (recrystallized from ethanol-ether) <br> Oxalate: <br> M.p. 121–122° C. (decomp.) <br> (recrystallized from ethanol-ether) |
| 128 | 3-Cl-C$_6$H$_4$ | " | " | O | " | Yield: 58.8% <br> M.p. 140–143° C. (recrystallized from ethyl acetate-n-hexane) <br> Oxalate hemihydrate: <br> M.p. 138–143° C. (decomp.) <br> (recrystallized from acetone) |
| 129 | 3-F-C$_6$H$_4$ | " | " | " | C$_2$H$_5$CO | Yield: 94% <br> M.p. 108–109° C. (recrystallized from ethyl acetate-ether) <br> Oxalate hemihydrate: <br> M.p. 157–158° C. (decomp.) <br> (recrystallized from acetone-ether) |
| 130 | 3-F-C$_6$H$_4$ | " | " | " | n-C$_4$H$_9$CO | Yield: 68.0% <br> M.p. 60–65° C. (recrystallized from isopropyl ether) <br> Oxalate: <br> M.p. 159–161° C. (decomp.) <br> (recrystallized from acetone) |

TABLE 10-continued

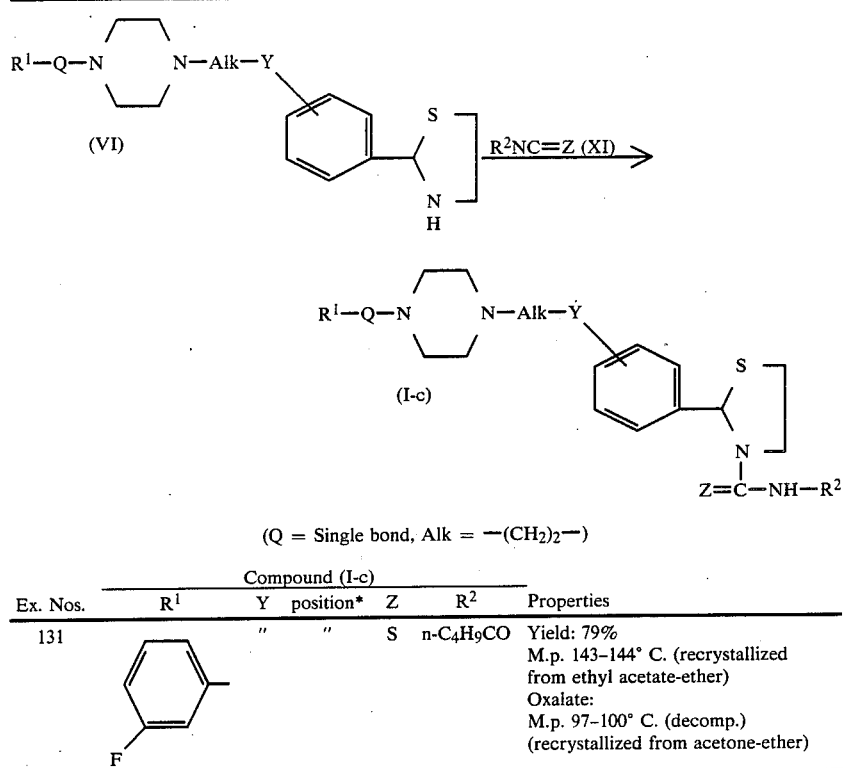

(Q = Single bond, Alk = —(CH$_2$)$_2$—)

| Ex. Nos. | Compound (I-c) R$^1$ | Y | position* | Z | R$^2$ | Properties |
|---|---|---|---|---|---|---|
| 131 | ![3-fluorophenyl] | " | " | S | n-C$_4$H$_9$CO | Yield: 79%<br>M.p. 143–144° C. (recrystallized from ethyl acetate-ether)<br>Oxalate:<br>M.p. 97–100° C. (decomp.)<br>(recrystallized from acetone-ether) |

*Same as defined in the footnote of Table 3

EXAMPLE 132

A mixture of 1.12 g of potassium isocyanate, 10 ml of water and 2 ml of acetic acid is added to a solution of 2.68 g of 2-{2-[2-(4-(3-fluorophenyl)piperazin-1-yl)ethyloxy]phenyl}thiazolidine in 20 ml of ethanol, and the mixture is stirred at room temperature for 2 hours. A mixture of 0.56 g of potassium isocyanate and 0.5 ml of acetic acid is added to said mixture, and the mixture is stirred at the same temperature for 2 hours. The mixture is made alkaline with sodium bicarbonate and concentrated under reduced pressure to remove solvent. The residue is extracted with ethyl acetate. The extract is washed with a saturated sodium chloride solution, dried and then concentrated under reduced pressure to remove solvent. The residue is purified by silica gel chromatograph (solvent, ethyl acetate), and the resultant product is recrystallized from a mixture of ethyl acetate and ether. 2.6 g of 2-{2-[2-(4-(3-fluorophenyl)piperazin-1-yl)ethyloxy]phenyl}thiazolidine-3-carboxamide are obtained.

M.p. 142°–143° C.
Oxalate:
M.p. 104°–105° C. (decomp.) (recrystallized from methanol-ether).

EXAMPLE 133

A solution of 1.07 g of sodium isocyanate in 20 ml of water is added to a solution of 3.03 g of 2-{2-[2-(4-phenylpiperazin-1-yl)ethyloxy]phenyl}thiazolidine in 40 ml of ethanol, and 2.46 g of acetic acid are added thereto. The mixture is stirred at room temperature for 2 hours. 200 ml of water are added to the mixture, and the aqueous mixture is made alkaline with potassium carbonate. The aqueous mixture is extracted with ethyl acetate and chloroform, successively. The extracts are combined, washed with water, dried and then concentrated under reduced pressure to remove solvent. The residue is recrystallized from ethyl acetate. 2.78 g of 2-{2-[2-(4-phenylpiperazin-1-yl)ethyloxy]phenyl}thiazolidine-3-carboxamide are obtained. Yield: 82.2%.

M.p. 137°–139° C.
Oxalate:
M.p. 146°–150.5° C. (decomp.) (recrystallized from acetone-methanol).

EXAMPLES 134 TO 135

The following compounds are obtained from the corresponding thiazolidine compounds and sodium isocyanate in the same manner as described in Example 133.

(134) 2-{2-[2-(4-(3-chlorophenyl)piperazin-1-yl)ethyloxy]phenyl}thiazolidine-3-carboxamide
Yield: 70.4%.
M.p. 141°–143° C. (recrystallized from ethyl acetate).
Oxalate:
M.p. 111°–115° C. (decomp.) (recrystallized from acetone-methanol).

(135) 2-{2-[2-(4-phenylpiperazin-1-yl)ethylthio]phenyl}thiazolidine-3-carboxamide
Yield: 58.4%.
M.p. 141°–143.5° C. (recrystallized from ethyl acetate). Oxalate hemihydrate:
M.p. 174°–177° C. (decomp.) (recrystallized from acetone).

EXAMPLE 136

A mixture of 0.63 g of benzamide, 0.73 g of phosgene and 50 ml of methylene chloride is refluxed for 3 hours, and the mixture is concentrated under reduced pressure to remove solvent. 30 ml of tetrahydrofuran and 1.2 g of triethylamine are added to the residue (i.e., benzoyl isocyanate), and a solution of 1.5 g of 2-{2-[2-(4-(3-fluorophenyl)piperazin-1-yl)ethyloxy]phenyl}thiazolidine in 10 ml of tetrahydrofuran is added thereto. The mixture is stirred at room temperature for 18 hours. Ethyl acetate is added to the mixture, and the mixture is washed with water, dried and then concentrated under reduced pressure to remove solvent. The residue is purified by silica gel chromatography (solvent, chloroform:ethyl acetate=7:3). The eluate is concentrated under reduced pressure to remove solvent, and the residue is recrystallized from a mixture of ethyl acetate and n-hexane. 0.87 g of N-benzoyl-2-{2-[2-(4-(3-fluorophenyl)piperazin-1-yl)ethyloxy]phenyl}thiazolidine-3-carboxamide is obtained.

M.p. 125°–127° C.
Sodium salt:
M.p. 118°–123° C.

EXAMPLE 137

0.9 g of ethoxycarbonyl isocyanate is added to a solution of 2 g of 2-{2-[2-(4-(3-fluorophenyl)piperazin-1-yl)ethyloxy]phenyl}thiazolidine in 30 ml of tetrahydrofuran, and the mixture is stirred at room temperature for 18 hours. 3.1 g of ethoxycarbonyl isocyanate are added to the mixture, and the mixture is stirred at room temperature for 2 hours. Water is added to the mixture, and the aqueous mixture is made alkaline with potassium carbonate. The aqueous mixture is extracted with ethyl acetate, and the extract is washed with water, dried and then concentrated under reduced pressure to remove solvent. The residue is purified by silica gel chromatography (solvent, benzene:ethyl acetate=1:1). 1.05 g of N-ethoxycarbonyl-2-{2-[2-(4-(3-fluorophenyl)piperazin-1-yl)ethyloxy]phenyl}thiazolidine-3-carboxamide are obtained as an amorphous powder.

IR $\nu_{max}^{nujol}$ (cm$^{-1}$): 3260, 1760, 1670.
Sodium salt:
M.p. 213°–217° C.

EXAMPLE 138

1.94 g of 2-{2-[2-(4-(3-fluorophenyl)piperazin-1-yl)ethyloxy]phenyl}thiazolidine are dissolved in anhydrous acetone, and 0.73 g of methanesulfonyl isocyanate is added thereto at room temperature. After the mixture is stirred for 30 minutes, the mixture is concentrated under reduced pressure to remove solvent. The residue is collected by filtration, and washed with water and ether, successively. The crude product thus obtained is recrystallized from a mixture of acetone and ether. 1.56 g of N-methanesulfonyl-2-{2-[2-(4-(3-fluorophenyl)piperazin-1-yl)ethyloxy]phenyl}thiazollidine-3-carboxamide are obtained.

M.p. 138°–140° C. (decomp.). Hemioxalate hemihydrate:
M.p. 171°–172° C. (decomp.).

EXAMPLE 139

0.68 g of diethylphosphoryl isothiocyanate is added to a solution of 1.23 g of 2-{2-[2-(4-(3-fluorophenyl)piperazin-1-yl)ethyloxy]phenyl}thiazolidine in 20 ml of acetone, and the mixture is stirred for one day. The mixture is concentrated under reduced pressure to remove solvent. The residue is extracted with chloroform, and the extract is washed with a saturated sodium chloride solution, dried and concentrated under reduced pressure to remove solvent. The residue is purified by silica gel chromatography (solvent, chloroform:methanol=40:1), and the resultant product is recrystallized from ethyl acetate and ether. 1.49 g of N-diethyl phosphoryl-2-{2-[2-(4-(3-fluorophenyl)piperazin-1-yl)ethyloxy]phenyl}thiazolidine-3-carbothioamide are obtained. Yield: 81%.

M.p. 128°–129° C.
Oxalate:
M.p. 79°–81° C. (decomp.) (recrystallized from acetone-ether).

EXAMPLE 140

0.1 g of sodium hydride (60% oil dispersion) is added to a solution of one g of N-methyl-2-{2-[2-(4-(3-fluorophenyl)piperazin-1-yl)ethyloxy]phenyl}thiazolidine-3-carboxamide in 30 ml of dimethylformamide, and a solution of 0.19 g of acetyl chloride in 5 ml of ether is added thereto. After the mixture is stirred at 50° C. for 20 hours, the mixture is concentrated under reduced pressure to remove solvent. Water is added to the residue, and the aqueous mixture is extracted with ethyl acetate. The extract is washed with water, dried and then concentrated under reduced pressure to remove solvent. The residue is purified by silica gel chromatography (solvent, ethyl acetate:n-hexane=4:1). 0.32 g of N-acetyl-N-methyl-2-{2-[2-(4-(3-fluorophenyl)piperazin-1-yl)ethyloxy]phenyl}thiazolidine-3-carboxamide is obtained as an oil.

IR $\nu_{max}^{liq}$ (cm$^{-1}$): 1670.
Mass (m/e): 486, 386.
Oxalate:
M.p. 110°–117° C. (decomp.) (recrystallized from acetone-methanol-n-hexane).

EXAMPLES 141 TO 142

The following compounds are obtained from the corresponding thiazolidine and acyl compounds in the same manner as described in Example 140.

(141) N-acetyl-N-methyl-2-{2-[2-(4-(3-fluorophenyl)-piperazin-1-yl)ethyloxy]phenyl}thiazolidine-3-carbothioamide Yield: 77.2%, oil.
IR $\nu_{max}^{neat}$ (cm$^{-1}$): 1670, 1610.
Mass (m/e): 502(M+), 429, 386, 207.
Oxalate:
M.p. 106°–109° C. (decomp.) (recrystallized from acetone-ether).

(142) N-acetyl-N-methyl-2-{2-[3-(4-phenylpiperazin-1-yl)propylthio]phenyl}thiazolidine-3-carbothioamide Yield: 52.0%, oil.
IR $\nu_{max}^{CHCl_3}$ (cm$^{-1}$): 1670.

Oxalate:

M.p. 135°–142° C. (decomp.) (recrystallized from acetone).

EXAMPLE 143

A mixture of 2.22 g of N-methyl-2-{2-[2-(4-(3-fluorophenyl)piperazin-1-yl)ethyloxy]phenyl}thiazolidine-3-carboxamide, 1.39 g of propionyl chloride, 2.53 g of triethylamine and 50 ml of toluene is refluxed for 2.5 days with stirring. The mixture is concentrated under reduced pressure to remove solvent. Water is added to the residue, and the aqueous mixture is extracted with ethyl acetate. The extract is washed with a saturated sodium bicarbonate solution and a saturated sodium chloride solution, successively. The ethyl acetate solution is dried and then concentrated under reduced pressure to remove solvent. The residue is purified by silica gel chromatography (solvent, chloroform:ethyl acetate=3:1). 0.30 g of N-methyl-N-propionyl-2-{2-[2-(4-(3-fluorophenyl)piperazine-1-yl)ethyloxy]phenyl}thiazolidine-3-carboxamide is obtained as an oil.

IR $\nu_{max}^{neat}$ (cm$^{-1}$): 1680–1640, 1600, 1575.

Mass (m/e): 500 (M$^+$).

Oxalate:

M.p. 125°–127° C. (crystallized from acetone-ether).

EXAMPLE 144

The following compound is obtained from the corresponding thiazolidine and benzoyl compounds in the same manner as described in Example 143.

(144) N-benzoyl-N-methyl-2-{2[2-(4-(3-fluorophenyl)piperazin-1-yl)ethyloxy]phenyl}thiazolidine-3-carbothioamide Yield: 81.6%.

M.p. 119°–121° C. (recrystallized from ethyl acetate-n-hexane).

IR $\nu_{max}^{CHCl_3}$ (cm$^{-1}$): 1650, 1603, 1580, 1485, 835.

Oxalate:

M.p. 102°–112° C. (recrystallized from ethanol-ether).

EXAMPLE 145

(1) 1.08 g of 2-{2-[2-(4-(3-fluorophenyl)piperazin-1-yl)ethyloxy]phenyl}thiazolidine-3-carboxamide are dissolved in 20 ml of tetrahydrofuran, and 0.76 g of triethylamine is added thereto. A solution of 0.59 g of acetyl chloride in one ml of tetrahydrofuran is added to the mixture under ice-cooling, and the mixture is stirred at room temperature for 3 days. 0.59 g of acetyl chloride and 0.76 g of triethylamine are added to the mixture, and the mixture is stirred at room temperature for 24 hours. The mixture is concentrated under reduced pressure to remove solvent. The residue is dissolved in ethyl acetate, and the solution is washed with a saturated sodium chloride solution, an aqueous sodium bicarbonate solution and a sodium chloride solution, successively. The ethyl acetate solution is dried and concentrated under reduced pressure to remove solvent. The residue is purified by silica gel chromatography (solvent, chloroform:ethyl acetate=2:1). The eluate is concentrated under reduced pressure to remove solvent, and the residue is recrystallized from a mixture of chloroform and ether. 0.72 g of N,O-diacetyl-2-{2-[2-(4-(3-fluorophenyl)piperazin-1-yl)ethyloxy]phenyl}thiazolidine-3-carboximidic acid is obtained. Yield: 56%.

M.p. 114°–115° C.

Oxalate:

M.p. 157°–158° C. (decomp.) (recrystallized from ethanol).

(2) 0.59 g of N,O-diacetyl-2-{2-[2-(4-(3-fluorophenyl)piperazin-1-yl)ethyloxy]phenyl}thiazolidine-3-carboximidic acid is dissolved in a mixture of 15 ml of ethanol and 5 ml of tetrahydrofuran, and 1.34 ml of 10% aqueous sodium hydroxide solution is added thereto under ice-cooling. The mixture is stirred for 15 minutes, and the mixture is neutralized with 10% hydrochloric acid. The mixture is concentrated under reduced pressure to remove solvent. The residue is extracted with ethyl acetate, and the extract is washed with an aqueous sodium chloride solution, dried and then concentrated under reduced pressure to remove solvent. The residue is recrystallized from a mixture of ethyl acetate and ether. 0.49 g of N-acetyl-2-{2-[2-(4-(3-fluorophenyl)piperazin-1-yl)ethyloxy]phenyl}thiazolidine-3-carboxamide is obtained.

Yield: 90%.

M.p. 142°–143° C.

Oxalate:

M.p. 165°–166° C. (decomp.) (recrystallized from ethanol).

EXAMPLE 146

(1) 0.311 g of acetyl chloride is added to a mixture of 1.49 g of 2-{2-[2-(4-phenylpiperazin-1-yl)ethyloxy]phenyl}thiazolidine-3-carboxamide, 1.27 g of triethylamine and 60 ml of benzene at 50° C., and the mixture is stirred at 80° C. for 1.5 hours. 0.563 g of acetyl chloride and 0.728 g of triethylamine are added to the mixture, and the mixture is stirred at 80° C. for 2.5 hours. The mixture is washed with water, dried and then concentrated under reduced pressure to remove solvent. The residue is purified by silica gel chromatography (solvent, benzene:ethyl acetate=1:1). The eluate is concentrated under reduced pressure to remove solvent, and the residue is recrystallized from ether. 1.25 g of N,O-diacetyl-2-{2-[2-(4-phenylpiperazin-1-yl)ethyloxy]phenyl}thiazolidine-3-carboximidic acid are obtained.

Yield: 70%.

M.p. 120°–123.5° C.

(2) A mixture of 1.19 g of N,O-diacetyl-2-{2-[2-(4-phenylpiperazin-1-yl)ethyloxy]phenyl}thiazolidine-3-carboximidic acid, 20 ml of ethanol, 0.287 g of sodium hydroxide, 2.7 ml of water and 20 ml of tetrahydrofuran is stirred for 1.5 hours under ice-cooling. The mixture is neutralized with 10% hydrochloric acid, and the mixture is extracted with ethyl acetate. The extract is washed with water, dried and then concentrated under reduced pressure to remove solvent. The residue is purified by silica gel chromatography (solvent, ethyl acetate:chloroform=5:1). The eluate is concentrated under reduced pressure to remove solvent, and the residue is recrystallized from a mixture of ethyl acetate and n-hexane. 0.72 g of N-acetyl-2-{2-[2-(4-phenylpiperazin-1-yl)ethyloxy]phenyl}thiazolidine-3-carboxamide is obtained.

Yield: 66.1%.

M.p. 137°–139° C.

Hemioxalate hemihydrate:

M.p. 164°–168° C. (decomp.) (recrystallized from acetone).

EXAMPLE 147

A mixture of 2.87 g of N-acetyl-2-{2-[2-(4-(3-fluorophenyl)piperazin-1-yl)ethyloxy]phenyl}thiazolidine-3-carbothioamide, 7.3 ml of 10% aqueous sodium hydroxide solution and 60 ml of ethanol is refluxed for 20 hours and then concentrated under reduced pressure to remove solvent. The residue is extracted with ethyl acetate, and the extract is washed with a saturated sodium chloride solution, dried and then concentrated under reduced pressure to remove solvent. The residue is purified by silica gel chromatography (solvent, chloroform:ethyl acetate=2:1). 2.36 g of 2-{2-[2-(4-(3-fluorophenyl)piperazin-1-yl)ethyloxy]phenyl}thiazolidine-3-carbothioamide are obtained. Yield: 90%.

M.p. 136°–137° C. (recrystallized from ether).

Hemifumarate:

M.p. 164°–165° C. (recrystallized from ethanol-ether).

EXAMPLE 148

(1) 5.33 g of (±)-N-methyl-2-{2-[2-(4-phenylpiperazin-1-yl)ethyloxy]phenyl}thiazolidine-3-carbothioamide are added to a suspension of 0.64 g of sodium hydride (50% oil dispersion) in 55 ml of dimethylformamide under ice-cooling, and the mixture is stirred at the same temperature for 10 minutes and further stirred at room temperature for 30 minutes. A solution of 4.00 g of (−)-1-(2-naphthylsulfonyl)pyrrolidine-2-carbonyl chloride in 40 ml of dimethylformamide is added to the mixture under ice-cooling, and the mixture is stirred at the same temperature for 30 minutes and further stirred at room temperature for 2 hours. Ice-water is added to the mixture, and the aqueous mixture is extracted with ethyl acetate. The extract is washed with a saturated sodium bicarbonate solution and water, dried and then concentrated under reduced pressure to remove solvent. The residue is chromatographed on the column of silica gel (solvent, benzene:ethyl acetate=3:2), whereby the following compounds are obtained, respectively.

(+)-N-methyl-N-[1-(2-naphthylsulfonyl)pyrrolidine-2-carbonyl]-2-{2-[2-(4-phenylpiperazin-1-yl)ethyloxy]phenyl}thiazolidine-3-carbothioamide Yield: 1.10 g.

M.p. 191°–192° C. (recrystallized from ethyl acetate-n-hexane).

$[\alpha]_D^{20}$+27.2° (c=0.206, chloroform).

A mixture of N-methyl-N-[1-(2-naphthylsulfonyl)-pyrrolidine-2-carbonyl]-2-{2-[2-(4-phenylpiperazin-1-yl)ethyloxy]phenyl}thiazolidine-3-carbothioamide and 2-[2-(4-phenylpiperazin-1-yl)ethyloxy]benzaldehyde.

Yield: 0.88 g, caramel.

(2) 1.06 g of (+)-N-methyl-N-[1-(2-naphthylsulfonyl)pyrrolidine-2-carbonyl]-2-{2-[2-(4-phenylpiperazin-1-yl)ethyloxy]phenyl}thiazolidine-3-carbothioamide obtained in pargraph (1) are dissolved in a mixture of 40 ml of tetrahydrofuran and 40 ml of methanol, and a solution of 120 mg of sodium hydroxide in 3 ml of water is added thereto under water-cooling and stirring. The mixture is stirred at room temperature for 16 hours and then concentrated under reduced pressure to remove solvent. Water is added to the mixture, and the aqueous mixture is extracted with methylene chloride. The extract is washed with water, dried and concentrated under reduced pressure to remove solvent. The residue is purified by silica gel chromatography (solvent, benzene:ethyl acetate=3:2), and the resultant product is recrystallized from a mixture of ethyl acetate and n-hexane. 600 mg of (+)-N-methyl-2-{2-[2-(4-phenylpiperazin-1-yl)ethyloxy]phenyl}thiazolidine-3-carbothioamide are obtained.

Yield: 93.3%.

M.p. 144°–145.5° C.

$[\alpha]_D^{20}$+145.7° (c=0.365, chloroform).

Fumarate hemihydrate:

M.p. 138°–144° C. (decomp.) (recrystallized from acetone-n-hexane).

$[\alpha]_D^{20}$+65.0° (c=0.150, methanol).

(3) 0.88 g of a mixture of N-methyl-N-[1-(2-naphthylsulfonyl)pyrrolidine-2-carbonyl]-2-{2-[2-(4-phenylpiperazin-1-yl)ethyloxy]phenyl}thiazolidine-3-carbothioamide and 2-[2-(4-phenylpiperazin-1-yl)ethyloxy]benzaldehyde obtained in paragraph (1) is dissolved in a mixture of 35 ml of tetrahydrofuran and 35 ml of methanol, and a solution of 100 mg of sodium hydroxide in 3 ml of water is added thereto under water-cooling and stirring. The mixture is stirred at room temperature for 24 hours and then concentrated under reduced pressure to remove solvent. Water is added to the residue, and the aqueous mixture is extracted with ethyl acetate. The extract is washed with water, dried and concentrated under reduced pressure to remove solvent. The residue is purified by silica gel chromatography (solvent, benzene:ethyl acetate=3:2), and the resultant product is recrystallized from a mixture of ethyl acetate and n-hexane. 108 mg of (−)-N-methyl-2-{2-[2-(4-phenylpiperazin-1-yl)ethyloxy]phenyl}thiazolidine-3-carbothioamide are obtained.

M.p. 143°–145° C.

$[\alpha]_D^{20}$−139.8° (c=0.265, chloroform).

EXAMPLE 149

(1) 0.64 g of sodium hydride (50% oil dispersion), 5.33 g of (±)-N-methyl-2-{2-[2-(4-phenylpiperazin-1-yl)ethyloxy]phenyl}thiazolidine-3-carbothioamide, (+)-1-(2-naphthylsulfonyl)pyrrolidine-2-carbonyl chloride and 95 ml of dimethylformamide are treated in the same manner as described in Example 148-(1), whereby the following compounds are obtained, respectively.

(−)-N-methyl-N-[1-(2-naphthylsulfonyl)pyrrolidine-2-carbonyl]-2-{2-[2-(4-phenylpiperazin-1-yl)ethyloxy]phenyl}thiazolidine-3-carbothioamide Yield: 1.08 g.

M.p. 191°–192° C. (recrystallized from ethyl acetate-n-hexane).

$[\alpha]_D^{20}$−26.5° (c=0.200, chloroform).

A mixture of N-methyl-N-[1-(2-naphthylsulfonyl)-pyrrolidine-2-carbonyl]-2-{2-[2-(4-phenylpiperazin-1-yl)ethyloxy]phenyl}thiazolidine-3-carbothioamide and 2-[2-(4-phenylpiperazin-1-yl)ethyloxy]benzaldehyde Yield: 1.04 g, caramel.

(2) 1.05 g of (−)-N-methyl-N-[1-(2-naphthylsulfonyl)pyrrolidine-2-carbonyl]-2-{2-[2-(4-phenylpiperazin-1-yl)ethyloxy]phenyl}thiazolidine-3-carbothioamide, 40 ml of tetrahydrofuran, 40 ml of methanol, 120 mg of sodium hydroxide and 3 ml of water are treated in the same manner as described in Example 148-(2). 600 mg of (−)-N-methyl-2-{2-[2-(4-phenylpiperazin-1-yl)ethyloxy]phenyl}thiazolidine-3-carbothioamide are obtained. Yield: 94.2%.

M.p. 144°–145.5° C. (recrystallized from ethyl acetate-n-hexane).

$[\alpha]_D^{20} - 145.4°$ (c=0.216, chloroform).

Fumarate hemihydrate:

M.p. 138°–144° C. (decomp.) (recrystallized from acetone-n-hexane).

$[\alpha]_D^{20} - 67.3°$ (c=0.110, methanol).

(3) 1.04 g of a mixture of N-methyl-N-[1-(2-naphthylsulfonyl)pyrrolidine-2-carbonyl]-2-{2-[2-(4-phenylpiperazin-1-yl)ethyloxy]phenyl}thiazolidine-3-carbothioamide and 2-[2-(4-phenylpiperazin-1-yl)ethyloxy]benzaldehyde obtained in paragraph (1), 30 ml of tetrahydrofuran, 30 ml of methanol, 120 mg of sodium hydroxide and 3 ml of water are treated in the same manner as described in Example 148-(3). 205 mg of (+)-N-methyl-2-{2-[2-(4-phenylpiperazin-1-yl)ethyloxy]phenyl}thiazolidine-3-carbothioamide are obtained.

M.p. 144°–145° C. (recrystallized from ethyl acetate-n-hexane).

$[\alpha]_D^{20} + 141.7°$ (c=0.206, chloroform).

Preparation of Starting Compounds

Preparation 1

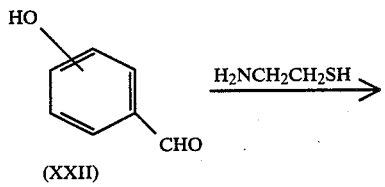
(XXII)

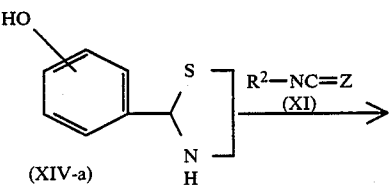
(XIV-a)

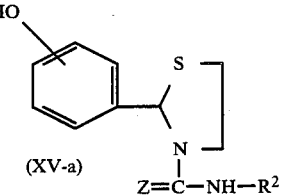
(XV-a)

wherein $R^2$ and Z are the same as defined above.

The reaction of the compound (XXII) and cysteamine or a salt thereof may be conducted in the same manner as in case of the reaction of the compound (XIX) and cysteamine, and the subsequent reaction of the compounds (XIV-a) and (XI) may be carried out in the same manner as described in Process (F).

The practical embodiments of the above-mentioned reactions are as follows:

A mixture of 5.65 g of cysteamine hydrochloride, 2 g of sodium hydroxide and 150 ml of ethanol is refluxed for 15 minutes. A solution of 6.1 g of salicylaldehyde in 30 ml of ethanol is added to said mixture, and the mixture is refluxed for 2 hours. The mixture is concentrated under reduced pressure to remove solvent. Benzene is added to the residue, and the mixture is concentrated under reduced pressure to remove solvent. 120 ml of tetrahydrofuran are added to the residue, and the mixture is stirred at room temperature for 1.5 hours. 3.5 g of methyl isocyanate are added to said mixture, and the mixture is stirred at room temperature for 30 minutes and further refluxed for one hour. The mixture is concentrated under reduced pressure to remove solvent. Water is added to the residue, and crystalline precipitates are collected by filtration. The crystals are washed with water and ethyl acetate, dried and then recrystallized from ethanol. 8.97 g of N-methyl-2-(2-hydroxyphenyl)thiazolidine-3-carboxamide are obtained. Yield: 75.4%.

M.p. 186°–188° C. (decomp.).

The following compounds are obtained from the corresponding starting compounds in the same manner as described above.

TABLE 11

| Compound (XV-a) | | | |
|---|---|---|---|
| position* | Z | $R^2$ | Properties |
| 2 | S | $CH_3$ | M.p. 179–182.5° C. (decomp.) (recrystallized from ethanol) |
| 4 | O | " | Yield: 68.1% M.p. 218–220° C. (recrystallized from ethanol) |
| " | S | " | Yield: 71.6% M.p. 151–152.5° C. (recrystallized from ethyl acetate) |

*Position means the position of the HO— group which is substituted on the benzene ring (the carbon atom of the benzene ring which carries a thiazolidine group is taken as the 1-position).

Preparation 2

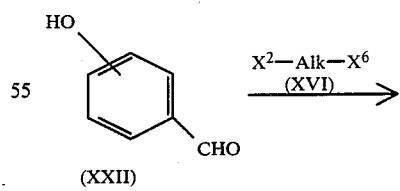
(XXII)

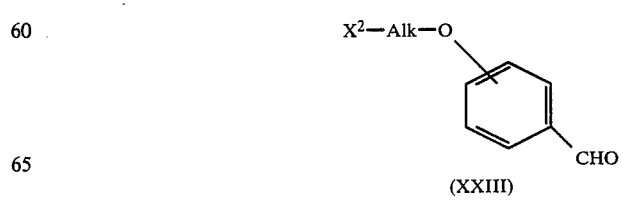
(XXIII)

wherein Alk, $X^2$ and $X^6$ are the same as defined above.

This reaction may be readily conducted at 0° to 100° C. in the presence of an acid acceptor such as those described in Processes (A) to (D).

The practical embodiments of the above-mentioned reaction are as follows.

40.0 g of 2-hydroxybenzaldehyde, 84 g of 1-chloro-2-tosyloxyethane and 50 g of potassium carbonate are added to 270 ml of dimethylformamide, and the mixture is stirred at room temperature for 3 days. After the reaction, half of the solvent is removed under reduced pressure. About 600 ml of water are added to the residue, and the mixture is extracted with ether. The extract is washed with 10% sodium hydroxide solution and water, dried and then concentrated under reduced pressure to remove solvent. The residue is distilled at 116°–118° C./0.2–0.3 mmHg to give 2-(2-chloroethyloxy)benzaldehyde (51.9 g, yield: 86%) as a colorless oil. The properties of this compound are the same as those disclosed in J.O.C., 18, 1380–1402 (1953).

The following compounds are obtained from the corresponding starting compounds in the same manner as described above.

TABLE 12

(Compound Nos. 1, 2, 3 and 5: $X^6$ = Br, No. 4: $X^6$ = tosyloxy)
Compound (XXIII)

| Nos. | $X^2$ | Alk | Position | Properties |
|---|---|---|---|---|
| 1 | Cl | —(CH$_2$)$_3$— | 2 | Yield: 85%<br>The physical properties are the same as those disclosed in Japanese Patent Publication (unexamined) No. 21126/1974 |
| 2 | Cl | —(CH$_2$)$_4$— | " | Yield: 95%<br>B.p. 150–153° C. (0.4 mmHg)<br>IR$\nu_{max}^{liq}$ (cm$^{-1}$): 1680, 1590, 760 |
| 3 | Br | —(CH$_2$)$_5$— | " | Yield: 72%<br>B.p. 148–157° C. (0.35 mmHg)<br>IR$\nu_{max}^{liq}$ (cm$^{-1}$): 1680, 1590 |
| 4 | Cl | —(CH$_2$)$_2$— | 4 | Yield: 59.5%<br>b.p. 116–118° C./0.25 mmHg |
| 5 | Cl | —(CH$_2$)$_3$— | " | Yield: 76.6%<br>b.p. 130–135° C./0.35 mmHg<br>IR$\nu_{max}^{liq}$ (cm$^{-1}$): 1680 |

*Position means the position of the $X^2$—Alk—O— group which is substituted on the benzene ring (the carbon atom of benzene ring which carries a formyl group is taken as the 1-position).

Preparation 3

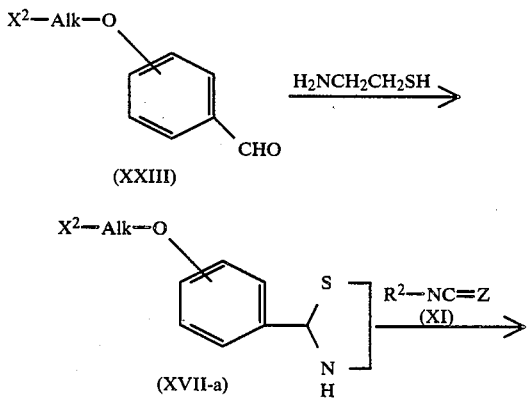

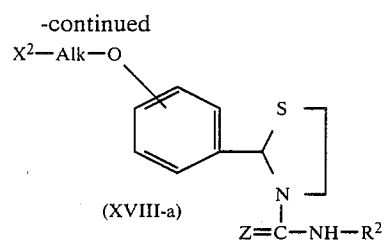

wherein $R^2$, Alk, Z and $X^2$ are the same as defined above.

The reaction of the compound (XXIII) and cysteamine or a salt thereof may be conducted in the same manner as in case of the reaction of the compound (XIX) and cysteamine, and the subsequent reaction of the compounds (XVII-a) and (XI) may be carried out in the same manner as described in Process (F).

The practical embodiments of the above-mentioned reactions are as follows:

A mixture of 11 g of 2-(2-chloroethyloxy)benzaldehyde, 6.81 g of cysteamine hydrochloride, 2.4 g of sodium hydroxide and 60 ml of ethanol is stirred at room temperature for 5 hours. The mixture is concentrated under reduced pressure to remove solvent. The residue is dissolved in 60 ml of tetrahydrofuran, and 3.42 g of methyl isocyanate are added thereto. After the mixture is stirred at room temperature for 15 hours, the mixture is concentrated under reduced pressure to remove solvent. Water is added to the residue, and crystalline precipitates are collected by filtration. The crystals are washed with water and recrystallized from ethanol. 12.68 g of N-methyl-2-[2-(2-chloroethyloxy)phenyl]-thiazolidine-3-carboxamide are obtained. Yield: 70%.

M.p. 166°–167° C.

The following compounds are obtained from the corresponding starting compounds in the same manner as described above.

TABLE 13

($R^2$ = CH$_3$)
Compound (XVIII-a)

| $X^2$ | Alk | Position* | Z | Properties |
|---|---|---|---|---|
| Cl | —(CH$_2$)$_2$— | 2 | S | Yield: 71%<br>M.p. 153–154.5° C. (recrystallized from ethanol) |
| Cl | —(CH$_2$)$_3$— | " | O | Yield; 63%<br>M.p. 128–130° C. (recrystallized from methanol - ether) |
| Cl | " | " | S | Yield: 52.8%<br>M.p. 118–120° C. (recrystallized from ethyl acetate - n-hexane) |
| Cl | —(CH$_2$)$_4$— | " | " | M.p. 137–143° C. (recrystallized from ethanol) |
| Br | —(CH$_2$)$_2$— | 4 | O | Yield: 71.9%<br>M.p. 96–98.5° C. (recrystallized from ethyl acetate - ether - n-hexane) |
| Cl | " | " | S | Yield: 50.3%<br>M.p. 114–116° C. (recrystallized from ethanol) |
| Cl | —(CH$_2$)$_3$— | " | O | Yield: 87.2%<br>M.p. 75–78° C. (recrystallized from ethyl acetate - ether - n-hexane) |
| Cl | " | " | S | Yield: 84.1%<br>M.p. 127.5–128.5° C. (recrystallized |

TABLE 13-continued (R² = CH₃)

Compound (XVIII-a)

| $X^2$ | Alk | Position* | Z | Properties |
|---|---|---|---|---|
|  |  |  |  | from ethanol) |

*Position means the position of the $X^2$—Alk—O— group which is substituted on the benzene ring (the carbon atom of benzene ring which carries a thiazolidine group is taken as the 1-position).

Preparation 4

A mixture of 5 g of N-methyl-2-(4-hydroxyphenyl)-thiazolidine-3-carbothioamide, 4.6 g of 1-chloro-2-tosyloxyethane, 4 g of potassium carbonate and 20 ml of dimethylformamide is stirred at room temperature for 2 days and further stirred at 50° C. for 20 hours. The mixture is concentrated under reduced pressure to remove solvent. Water is added to the residue, and the aqueous mixture is extracted with ethyl acetate. The extract is washed with an aqueous 10% sodium hydroxide solution and water, and dried and then concentrated under reduced pressure to remove solvent. The residue is purified by silica gel chromatography (solvent, ethyl acetate:chloroform=2:8), and the resultant product is recrystallized from ethanol. 3.07 g of N-methyl-2-[4-(2-chloroethyloxy)phenyl]thiazolidine-3-carbothioamide are obtained. Yield: 51.9%.

M.p. 114°–116° C.

The following compounds are obtained from the corresponding starting compounds in the same manner as described above.

TABLE 14

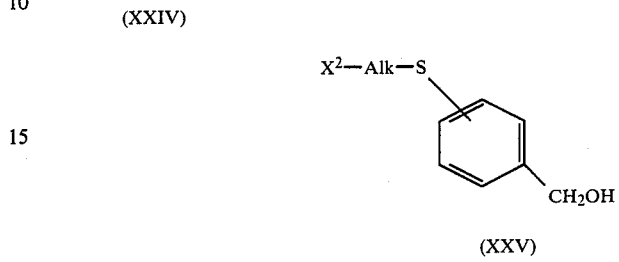

($X^2$ = Cl, Y = O, Z = S, $R^2$ = CH₃, $R^3$ = H, $X^6$ = Br)

Compound (IV)

| Alk | position* | Properties |
|---|---|---|
| —(CH₂)₃— | 4 | Yield: 62.7% |
|  |  | M.p. 127.5–128.5° C. (recrystallized from ethanol) |
| —(CH₂)₄— | 4 | M.p. 132–134° C. (recrystallized from ethanol) |

*Position means the position of the $X^2$—Alk—Y— group which is substituted on the benzene ring (the carbon atom of benzene ring which carries a thiazolidine group is taken as the 1-position).

Preparation 5

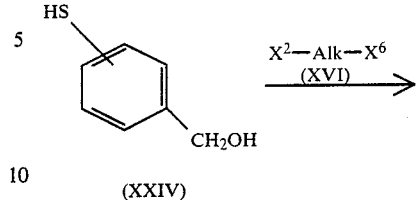

wherein Alk, $X^2$ and $X^6$ are the same as defined above.

This reaction may be readily conducted in the same manner as described in Preparation 2.

The practical embodiments of the above-mentioned reaction are as follows:

A mixture of 11.9 g of 2-(hydroxymethyl)thiophenol, 35.44 g of 1-bromo-3-chloropropane, 11.58 g of potassium carbonate and 150 ml of dimethylformamide is stirred at room temperature for 2 hours. Insoluble materials are filtered off, and the filtrate is concentrated under reduced pressure to remove solvent. Water is added to the residue, and the aqueous mixture is extracted with ethyl acetate. The extract is wahsed with water, dried and concentrated under reduced pressure to remove solvent. The residue is distilled under reduced pressure. 16.8 g of 2-(3-chloropropylthio)benzylalcohol are obtained as colorless oil. Yield: 93%.

B.p. 148°–159° C. (0.25 mmHg).

IR $\nu_{max}^{liq}$ (cm⁻¹): 3350, 1580, 1430, 1030, 750.

30 g of 2-(hydroxymethyl)thiophenol and 76.8 g of 1-bromo-2-chloroethane are treated in the same manner as described above, whereby 32.8 g of 2-(2-chloroethylthio)benzylalcohol are obtained. Yield: 75.5%.

B.p. 143°–148° C. (0.6 mmHg).

Preparatin 6

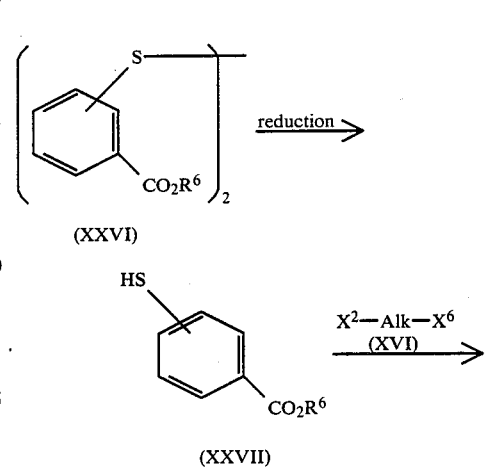

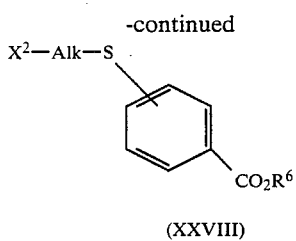

(XXVIII)

wherein $R^6$ is a lower alkyl group and Alk, $X^2$ and $X^6$ are the same as defined above.

The compound (XXVII) may be obtained by reducing the compound (XXVI) with a reducing agent such as sodium borohydride or zinc and acetic acid at 0° to 100° C., and the subsequent reaction of the compounds (XXVII) and (XVI) may be conducted in the same manner as described in Preparation 2. Reduction of the compound (XXVIII) with a reducing agent such as lithium aluminum hydride or lithium borohydride at 0° to 30° C. gives the compound (XXV).

The practical embodiments of the above-mentioned reactions are as follows:

(a) 33.4 g of bis(4-methoxycarbonylphenyl)disulfide are suspended in a mixture of 200 ml of dioxane and 120 ml of methanol, and 5.7 g of sodium borohydride are added thereto under ice-cooling and stirring. 6 g of sodium hydride (60% oil dispersion) are added to the mixture, and a solution of 37.8 g of 1-bromo-3-chloropropane in 120 ml of dioxane is added thereto. The mixture is stirred at room temperature for one hour and further refluxed for one hour. 4 g of sodium borohydride, 4 g of sodium hydride (50% oil dispersion) and 8 g of 1-bromo-3-chloropropane are added to the mixture, and the mixture is refluxed for 30 minutes. The mixture is poured into ice-water, and the aqueous mixture is extracted with chloroform. The extract is washed with water, dried and concentrated under reduced pressure to remove solvent. The residue is distilled under reduced pressure. 31.9 g of methyl 4-(3-chloropropylthio)benzoate are obtained as pale yellow oil. Yield: 65%.

B.p. 155°-164° C. (0.3 mmHg).

5 g of lithium aluminum hydride are suspended in 200 ml of tetrahydrofuran, and a solution of 31.9 g of methyl 4-(3-chloro-propylthio)benzoate in 200 ml of tetrahydrofuran is added thereto at 5° to 15° C. The mixture is stirred at the same temperature for 45 minutes. Water is added to the mixture at a temperature of below 20° C., and insoluble materials are filtered off. The filtrate is concentrated under reduced pressure to remove solvent, and the residue is distilled under reduced pressure. 24.1 g of 4-(3-chloropropylthio)benzylalcohol are obtained as an oil. Yild: 85%.

B.p. 144°-154° C. (0.35 mmHg).

(b) 40.1 g of bis(4-methoxycarbonylphenyl)disulfide, "g of 1-bromo-2-chloroethane, 13 g of sodium borohydride, 13.6 g of sodium hydride (60% oil dispersion), 100 ml of methanol and 320 ml of dixoane are treated in the same manner as described in paragraph (a), whereby 36 g of methyl 4-(2-chloroethylthio)benzoate are obtained as crude product. The crude product (36 g) is treated with 4.63 g of lithium aluminum hydride, whereby 16.3 g of 4-(2-chloroethylthio)benzylalcohol are obtained as crude product. A mixture of the crude product (16.3 g) thus obtained, one ml of 10% hydrochloric acid and 100 ml of ethanol is stirred at 50° C. for 1.5 hours. The mixture is concentrated under reduced pressure to remove solvent. Water is added to the residue, and the aqueous mixture is extracted with ethyl acetate. The extract is washed with an aqueous sodium bicarbonate solution and water, dried and then concentrated under reduced pressure to remove solvent. The residue is purified by silica gel chromatography (solvent, chloroform). 10 g of 4-(2-chloroethylthio)benzylalcohol are obtained as an oil.

Mass (m/e): 202, 204, 153, 123, 107.

Preparation 7

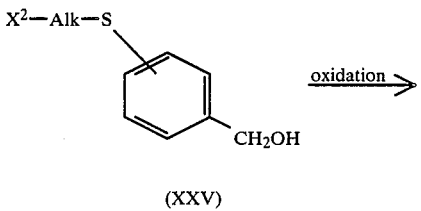

(XXIX)

wherein Alk and $X^2$ are the same as defined above.

The oxidation may be carried out by treating the compound (XXV) with dimethylsulfoxide and oxalyl chloride in the presence of a tertiary amine at $-60°$ to 30° C. or by treating said compound with manganese dioxide.

The practical embodiments of the above-mentioned reaction are as follows:

A solution of 27.8 g of dimethylsulfoxide in 50 ml of methylene chloride is added to a solution of 22.6 g of oxalyl chloride in 450 ml of methylene chloride at $-60°$ C. during one hour, and a solution of 32.7 g of 2-(2-chloroethylthio)benzylalcohol in 50 ml of methylene chloride is added thereto. The mixture is stirred for 15 minutes, and a solution of 71.8 g of triethylamine in 50 ml of methylene chloride is added to the mixture at $-60°$ C. The mixture is stirred at the same temperature for 5 minutes and further stirred at room temperature for one hour. Water is added to the mixture, and the methylene chloride layer is collected therefrom. The methylene chloride solution is washed with water, dried and concentrated under reduced pressure to remove solvent. The residue is distilled under reduced pressure. 29.7 g of 2-(2-chloroethylthio)benzaldehyde are obtained as an oil. Yield: 91.6%.

B.p. 135°-140° C. (0.4 mmHg).

$IR\nu_{max}^{liq}$ (cm$^{-1}$): 1690.

The following compounds are obtained from the corresponding starting compounds in the same manner as described above.

TABLE 15

| Compound (XXIX) | | | |
|---|---|---|---|
| $X^2$ | Alk | position* | Properties |
| Cl | $-(CH_2)_3-$ | 2 | Yield: 93.7%<br>B.p. 149–151° C. (0.7 mmHg)<br>$IR\nu_{max}^{liq}$ (cm$^{-1}$): 1690 |
| Cl | " | 4 | Yield: 92%<br>oil<br>$IR\nu_{max}^{liq}$ (cm$^{-1}$): 1680, 1660 |
| Cl | $-(CH_2)_2-$ | " | Yield: 93%<br>oil |

*Position means the position of the $X^2$—Alk—S— group which is substituted on the benzene ring (the carbon atom of benzene ring which carries a formyl group is taken as the 1-position).

Preparation 8

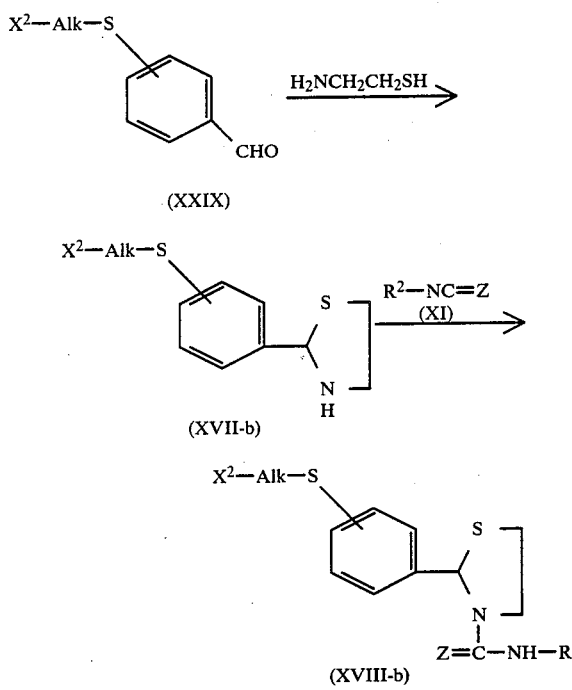

wherein $R^2$, Alk, Z and $X^2$ are the same as defined above.

The reaction of the compound (XXIX) and cysteamine or its salt may be conducted in the same manner as in case of the reaction of the compound (XIX) and cysteamine, and the subsequent reactions of the compounds (XVII-b) and (XI) may be carried out in the same manner as described in Process (F).

The practical embodiments of the above-mentioned reactions are as follows:

3.34 g of sodium hydroxide and 9.21 g of cysteamine hydrochloride are added to a solution of 14.8 g of 2-(2-chloroethylthio)benzaldehyde in 300 ml of ethanol, and the mixture is stirred at room temperature for 16 hours. The mixture is concentrated under reduced pressure to remove solvent, and 300 ml of tetrahydrofuran and 5.04 g of methyl isocyanate are added to the residue. The mixture is stirred at room temperature for 20 hours and then concentrated under reduced pressure to remove solvent. Water is added to the residue, and the aqueous mixture is extracted with chloroform. The extract is washed with water, dried and concentrated under reduced pressure to remove solvent. The residue is purified by silica gel chromatography (solvent, chloroform- :ethanol=50:1). 11.3 g of N-methyl-2-[2-(2-chloroethyl- thio)phenyl]thiazolidine-3-carboxamide are obtained.

M.p. 123°–125° C.

The following compounds are obtained from the corresponding starting compounds in the same manner as described above.

TABLE 16

| Compound (XVIII-b) | | | | | |
|---|---|---|---|---|---|
| $X^2$ | Alk | Position* | $R^2$ | Z | Properties |
| Cl | $-(CH_2)_2-$ | 2 | $CH_3$ | S | M.p. 134–136° C. |
| Cl | $-(CH_2)_3-$ | " | " | O | Yield: 76.3%<br>M.p. 116–118° C.<br>(recrystallized from ethanol-ether) |
| Cl | " | " | " | S | Yield: 73.6%<br>M.p. 140–142° C.<br>(recrystallized from ethanol) |
| Cl | $-(CH_2)_2-$ | 4 | " | " | Yield: 51%<br>oil<br>Mass (m/e): 332, 334, 258, 198 |
| Cl | " | " | " | O | Yield: 72%<br>oil<br>Mass (m/e): 316, 318, 257, 198 |
| Cl | $-(CH_2)_3-$ | " | " | " | M.p. 102–105° C. |
| Cl | " | " | " | S | Yield: 60%<br>M.p. 120.5–122.5° C. |

*Position means the position of the $X^2$—Alk—S— group which is substituted on the benzene ring (the carbon atom of benzene ring which carries a thiazolidine group is taken as the 1-position).

Preparation 9

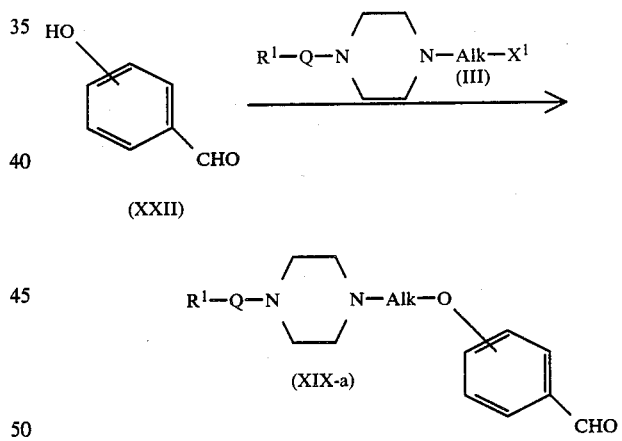

wherein $R^1$, Q, Alk, and $X^1$ are the same as defined above.

This reaction may be conducted in the same manner as described in Process (A).

The practical embodiments of the above-mentioned reaction are as follows:

A mixture of 3.88 g of 2-hydroxybenzaldehyde sodium salt, 7.00 g of 1-(3-chloropropyl)-4-phenylpiperazine dihydrochloride, 6.80 g of potassium carbonate and 50 ml of dimethylformamide is stirred at 60° to 70° C. for 15 hours under nitrogen atmosphere, and is concentrated under reduced pressure to remove solvent. Water is added to the residue, and the aqueous mixture is extracted with ether. The extract is washed with water, dried and concentrated under reduced pressure to remove solvent. The residue is purified by silica gel chromatography (solvent, chloroform:methanol=99:1). 5.42 g of 2-[3-(4-phenylpiperazin-1-yl)propyloxy]benzaldehyde are obtained as an oil.

Yield: 74.4%.

The physico-chemical properties of this product are identical with those of the compound described in Indian. J. Chem. Sect B., 21B, pp 435–439 (1982).

The following compounds are obtained from the corresponding starting compounds in the same manner as described above.

TABLE 17

(Q = Single bond, Alk = —(CH$_2$)$_3$—, X$^1$ = Cl)

Compound (XIX-a)

| R$^1$ | position* | Properties |
|---|---|---|
| 3-Cl-C$_6$H$_4$— | 2 | Yield: 60.9%<br>M.P. 86–90° C.; IR$\nu_{max}^{nujol}$ (cm$^{-1}$): 1680 |
| 3-F-C$_6$H$_4$— | " | Yield: 62.9%<br>M.p. 65–70° C.; IR$\nu_{max}^{nujol}$ (cm$^{-1}$): 1680 |
| 3-CH$_3$-C$_6$H$_4$— | " | Yield: 58.9%<br>M.p. 53–54° C.; IR$\nu_{max}^{nujol}$ (cm$^{-1}$): 1690 |
| C$_6$H$_5$— | 3 | The physico-chemical properties of these compounds are identical with those of the compounds described in Indian. J. Chem. Sect B., 21B, pp 435–439 (1982). |
| C$_6$H$_5$— | 4 | |

*Position means the position of the R$^1$—Q—N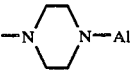N—Alk—O— group which is substituted on the benzene ring (the carbon atom of benzene ring which carries a formyl group is taken as the 1-position).

Preparation 10

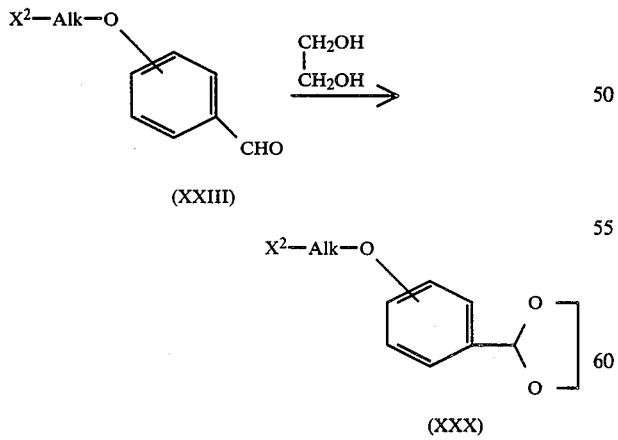

wherein Alk and X$^2$ are the same as defined above.

This reaction may be conducted in the presence of an acid such as phosphoric acid or hydrochloric acid at 80° to 140° C.

The practical embodiments of the above-mentioned reaction are as follows:

To a solution of 46.5 g of 2-(2-chloroethyloxy)benzaldehyde and 33.2 g of ethylene glycol in 500 ml of benzene in added 0.5 ml of 85% phosphoric acid, and the mixture is refluxed with stirring for about 18 hours while removing the produced water. After the reaction, the reaction mixture is cooled with ice and is made alkaline with saturated sodium bicarbonate solution to separate into two layers. The benzene layer is taken, washed with saturated saline solution, dried and then distilled to remove the solvent. The crude product thus obtained is distilled to give 56 g of 2-(2-chloroethyloxy)benzaldehyde ethyleneacetal (yield: 97%) as a colorless oil. b.p. 130°–135° C./0.3 mmHg.

IR$\nu_{max}^{liq}$ (cm$^{-1}$): 1600, 1490, 760.

The following compounds are obtained from the corresponding starting compounds in the same manner as described above.

TABLE 18

Compound (XXX)

| X$^2$ | Alk | Position* | Properties |
|---|---|---|---|
| Cl | —(CH$_2$)$_3$— | 2 | Yield: 94%<br>B.p. 136–137° C. (0.2 mmHg)<br>IR$\nu_{max}^{liq}$ (cm$^{-1}$): 1600, 1490, 750 |
| Cl | —(CH$_2$)$_4$— | " | Yield: 90%<br>B.p. 154–167° C. (0.4 mmHg)<br>IR$\nu_{max}^{liq}$ (cm$^{-1}$): 1600, 1490, 750 |
| Br | —(CH$_2$)$_5$— | " | Yield: 88%<br>B.p. 160–165° C. (0.35 mmHg)<br>IR$\nu_{max}^{liq}$ (cm$^{-1}$): 1600, 1490, 1250, 1070 750 |
| Cl | —(CH$_2$)$_3$— | 4 | Yield: 84.5%<br>B.p. 151–156° C. (0.3 mmHg)<br>IR$\nu_{max}^{liq}$ (cm$^{-1}$): 1610, 1250, 1080 |

*Position means the position of the X$^1$—Alk—O— group which is substituted on the benzene ring (the carbon atom of benzene ring that carries an acetal group is taken as the 1-position).

Preparation 11

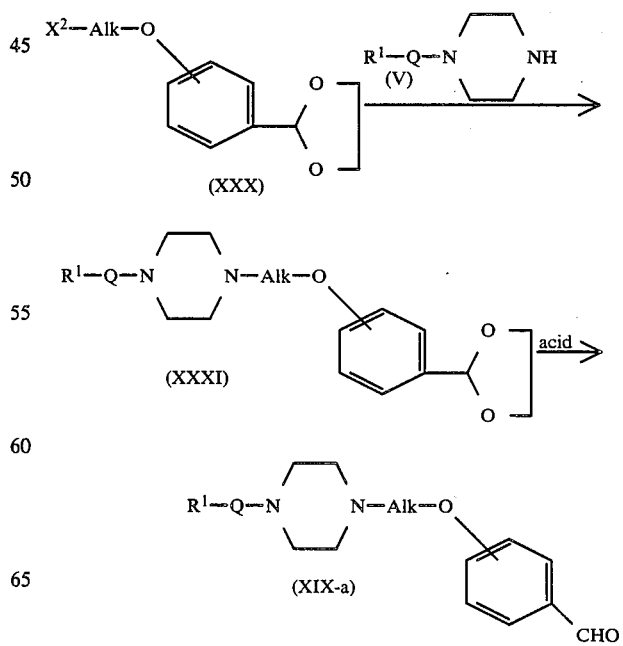

wherein $R^1$, Q, Alk and $X^2$ are the same as defined above.

The reaction of the compounds (XXX) and (V) may be conducted in the same manner as described in Process (B), and the subsequent acid treatment of the compound (XXXI) may be carried out at 0° to 100° C. by the use of such an acid as hydrochloric acid, sulfuric acid or hydrobromic acid.

The practical embodiments of the above-mentioned reactions are as follows:

A suspension of 2.29 g of 2-(2-chloroethyloxy)benzaldehyde ethyleneacetal, 1.73 g of N-phenylpiperazine, 1.50 g of anhyrous potassium carbonate and 15 ml of dimethylformamide is stirred at 70°-80° C. for about 18 hours under argon atmosphere. The reaction mixture is concentrated under reduced pressure to remove dimethylformamide. Water is added to the residue, and the aqueous mixture is extracted with ether. The extract is washed with water, dried and concentrated under reduced pressure to remove solvent. The residue is dissolved in 10 ml of methanol, and 10% hydrochloric acid is added thereto. The mixture is heated at 60° to 70° C. for 10 to 20 minutes, and then is made alkaline with 10% sodium hydroxide solution and extracted with ether. The extract is washed with water, dried and concentrated under reduced pressure to remove solvent. The residue is purified by silica gel chromatography (solvent, ethyl acetate:chloroform=2:8). 1.33 g of 2-[2-(4-phenylpiperazin-1-yl)ethyloxy]benzaldehyde are obtained as a colorless oil.

$IR\nu_{max}^{liq}$ (cm$^{-1}$); 1685.

The following compounds are obtained from the corresponding starting compounds in the same manner as described above.

TABLE 19

($X^2$ is Cl when Alk is —(CH$_2$)$_2$—, —(CH$_2$)$_3$— or —(CH$_2$)$_4$—; or $X^2$ is Br when Alk is —(CH$_2$)$_5$—)

Compound (XIX-a)

| $R^1$ | Q | Alk | position* | Properties |
|---|---|---|---|---|
| 2-F-phenyl | Single bond | —(CH$_2$)$_2$— | 2 | Yield: 62%, oil; $IR\nu_{max}^{liq}$ (cm$^{-1}$): 1680 |
| 3-F-phenyl | " | " | " | Yield: 64%; M.p. 76–78° C. (recrystallized from ether-n-hexane) |
| 4-F-phenyl | " | " | " | Yield: 67%; M.p. 68–74° C. |
| 2-Cl-phenyl | " | " | " | oil; $IR\nu_{max}^{liq}$ (cm$^{-1}$): 1680 |
| 3-Cl-phenyl | " | " | " | oil; $IR\nu_{max}^{liq}$ (cm$^{-1}$): 1680 |
| 4-Cl-phenyl | " | " | " | Yield: 65%; M.p. 95–105° C. (recrystallized from ether) |
| 2-CH$_3$-phenyl | " | " | " | oil; $IR\nu_{max}^{liq}$ (cm$^{-1}$): 1680, 1590 |

TABLE 19-continued (X² is Cl when Alk is —(CH₂)₂—, —(CH₂)₃— or —(CH₂)₄—; or
X² is Br when Alk is —(CH₂)₅—)

Compound (XIX-a)

| R¹ | Q | Alk | position* | Properties |
|---|---|---|---|---|
| 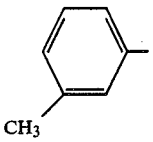 CH₃ | " | " | " | oil<br>IR$\nu_{max}^{liq}$ (cm⁻¹): 1680, 1590 |
| 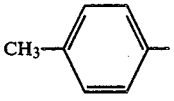 CH₃ | " | " | " | oil<br>IR$\nu_{max}^{liq}$ (cm⁻¹): 1680, 1590, 1230 |
| 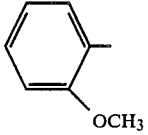 OCH₃ | " | " | " | Yield: 57%<br>M.p. 78–80° C. |
| 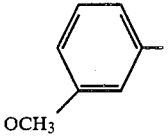 OCH₃ | " | " | " | Yield: 51%, oil<br>IR$\nu_{max}^{liq}$ (cm⁻¹): 1680, 1590 |
| 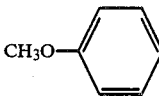 CH₃O | " | " | " | oil<br>IR$\nu_{max}^{liq}$ (cm⁻¹): 1680 |
| 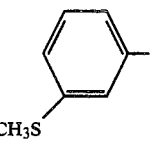 CH₃S | " | " | " | Yield: 64%, oil<br>IR$\nu_{max}^{liq}$ (cm⁻¹): 1680 |
| 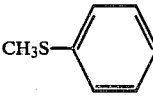 CH₃S | " | " | " | Yield: 64%<br>M.p. 85–90° C. (recrystallized from ethanol) |
| 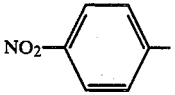 NO₂ | " | " | " | M.p. 139–142° C. (recrystallized from ethyl acetate-n-hexane) |
| 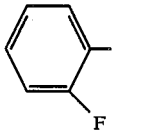 F | " | —(CH₂)₃— | " | Yield: 68%<br>M.p. 81–84° C. |
| 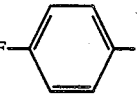 F | " | " | " | Yield: 80%<br>M.p. 54–57° C. |
| 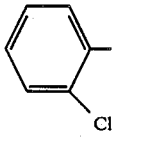 Cl | " | " | " | Yield: 54%, oil<br>IR$\nu_{max}^{liq}$ (cm⁻¹): 1680 |

TABLE 19-continued ($X^2$ is Cl when Alk is $-(CH_2)_2-$, $-(CH_2)_3-$ or $-(CH_2)_4-$; or
$X^2$ is Br when Alk is $-(CH_2)_5-$)

Compound (XIX-a)

| $R^1$ | Q | Alk | position* | Properties |
|---|---|---|---|---|
| 4-Cl-C$_6$H$_4$- | " | " | " | oil<br>IR$\nu_{max}^{liq}$ (cm$^{-1}$): 1680 |
| 2-CH$_3$-C$_6$H$_4$- | " | " | " | Yield: 63%, oil<br>IR$\nu_{max}^{liq}$ (cm$^{-1}$): 1680 |
| 4-CH$_3$-C$_6$H$_4$- | " | " | " | Yield: 89%<br>M.p. 46–51° C. |
| 2-OCH$_3$-C$_6$H$_4$- | " | " | " | Yield: 67%<br>M.p. 104–108° C. |
| 3-OCH$_3$-C$_6$H$_4$- | " | " | " | oil<br>IR$\nu_{max}^{liq}$ (cm$^{-1}$): 1680, 1590 |
| 4-CH$_3$O-C$_6$H$_4$- | " | " | " | Yield: 52%<br>M.p. 58–62° C. |
| 3-SCH$_3$-C$_6$H$_4$- | " | " | " | Yield: 70%<br>M.p. 53–56° C. (recrystallized from isopropyl ether-ether) |
| 4-CH$_3$S-C$_6$H$_4$- | " | " | " | Yield: 81%<br>M.p. 82–84.5° C. (recrystallized from ethyl acetate-n-hexane) |
| 4-NO$_2$-C$_6$H$_4$- | " | " | " | Yield: 62%<br>M.p. 121–123.5° C. |
| 2-F-C$_6$H$_4$- | " | $-(CH_2)_4-$ | " | Yield: 96.2%, oil<br>IR$\nu_{max}^{liq}$ (cm$^{-1}$): 1680, 1590, 1500 |
| 3-F-C$_6$H$_4$- | " | " | " | oil<br>IR$\nu_{max}^{liq}$ (cm$^{-1}$): 1680 |

TABLE 19-continued

| | (X² is Cl when Alk is —(CH₂)₂—, —(CH₂)₃— or —(CH₂)₄—; or X² is Br when Alk is —(CH₂)₅—) | | | |
|---|---|---|---|---|
| | Compound (XIX-a) | | | |
| R¹ | Q | Alk | position* | Properties |
| CH₃—⟨phenyl⟩— | " | " | " | Yield: 75%, oil<br>$IR\nu_{max}^{liq}$ (cm⁻¹): 1680, 1590, 1230 |
| CH₃O—⟨phenyl⟩— | " | " | " | M.p. 59–63° C. (recrystallized from isopropyl ether-ether) |
| CH₃S—⟨phenyl⟩— | " | " | " | Yield: 62%<br>M.p. 77–80.5° C. (recrystallized from ethyl acetate-n-hexane) |
| NO₂—⟨phenyl⟩— | " | " | " | Yield: 51%<br>M.p. 118–120° C. (recrystallized from ethyl acetate-n-hexane) |
| ⟨phenyl⟩— | " | —(CH₂)₅— | " | Yield: 61%, oil<br>$IR\nu_{max}^{liq}$ (cm⁻¹): 1680, 1590 |
| CH₃O—⟨phenyl⟩— | " | " | " | M.p. 55–58° C. |
| ⟨phenyl⟩— | —CH₂— | —(CH₂)₂— | " | Yield: 76.1%, oil<br>$IR\nu_{max}^{liq}$ (cm⁻¹): 1680, 1590 |
| ⟨phenyl⟩— | " | —(CH₂)₃— | " | Yield 66.7%, oil<br>$IR\nu_{max}^{liq}$ (cm⁻¹): 1680, 1590 |
| ⟨phenyl⟩— | —CH=CH—CH₂— | " | " | Yield: 78.3%, oil<br>$IR\nu_{max}^{liq}$ (cm⁻¹): 1685, 1595, 750 |

*Same as defined in the footnote of Table 17

Preparation 12

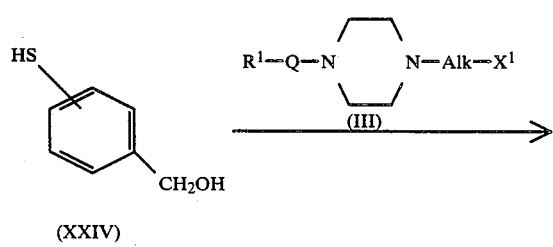

(XXIV)

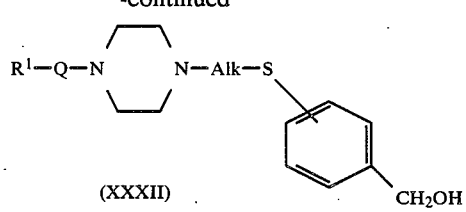

(XXXII)

wherein R¹, Q, Alk and X¹ are the same as defined above.

The reaction may be conducted in the same manner as described in Process (A).

The practical embodiments of the above-mentioned reaction are as follows:

A mixture of 1.56 g of 2-(hydroxymethyl)thiophenol, 3.77 g of 1-(3-chloropropyl)-4-phenylpiperazine dihydrochloride, 5.02 g of potassium carbonate and 40 ml of dimethylformamide is stirred at 50° C. for 6 hours. Insoluble materials are filtered off, and the filtrate is concentrated under reduced pressure to remove solvent. Water is added to the residue, and the aqueous mixture is extracted with ethyl acetate. The extract is washed with water, dried and concentrated under reduced pressure to remove solvent. The residue is digested with n-hexane and collected by filtration. 3.42 g of 2-[3-(4-phenylpiperazin-1-yl)propylthio]benzylalcohol are obtained. Yield: 91%.

M.p. 99°–103° C. (recrystallized from isopropyl ether-ethyl acetate)

Preparation 13

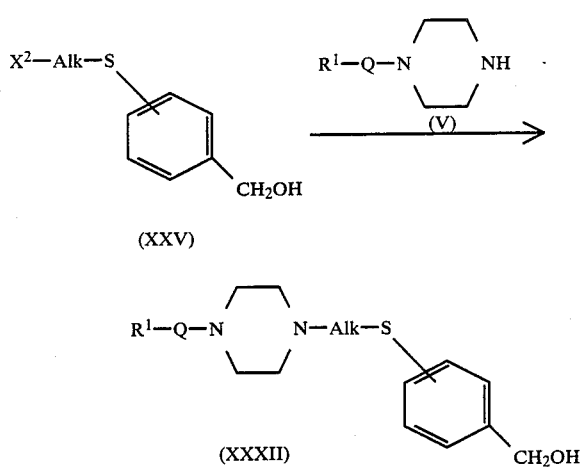

wherein $R^1$, Q, Alk, and $X^2$ are the same as defined above.

This reaction may be conducted in the same manner as described in Process (B).

The practical embodiments of the above-mentioned reaction are as follows:

A mixture of 2.6 g of 2-(3-chloropropylthio)benzylalcohol, 1.95 g of N-phenylpiperazine, 1.66 g of potassium carbonate and 30 ml of dimethylformamide is stirred at 50° C. for 7 hours. 0.39 g of N-phenylpiperazine is added to the mixture, and the mixture is stirred at 60° C. for 15 hours and further stirred at 70° C. for 4 hours. Insoluble materials are filtered off, and the filtrate is concentrated under reduced pressure to remove solvent. Water is added to the residue, and the aqueous mixture is extracted with ethyl acetate. The extract is washed with water, dried and concentrated under reduced pressure to remove solvent. The residue is purified by silica gel chromatography (solvent, chloroform-:methanol=20:1). 2.4 g of 2-[3-(4-phenylpiperazin-1-yl)propylthio]benzylalchol are obtained. Yield: 58%.

M.p. 99°–103° C. (recrystallized from isopropyl ether-ethyl acetate). 12.16 g of 2-(2-chloroethylthio)-benzylalcohol, 9.73 g of N-phenylpiperazine, 9.12 g of potassium carbonate and 80 ml of dimethylformamide are treated in the same manner as described above. 6.03 g of 2-[2-(4-phenylpiperazin-1-yl)ethylthio]benzylalcohol are obtained. M.p. 72°–74° C. (recrystallized from isopropyl ether).

Preparation 14

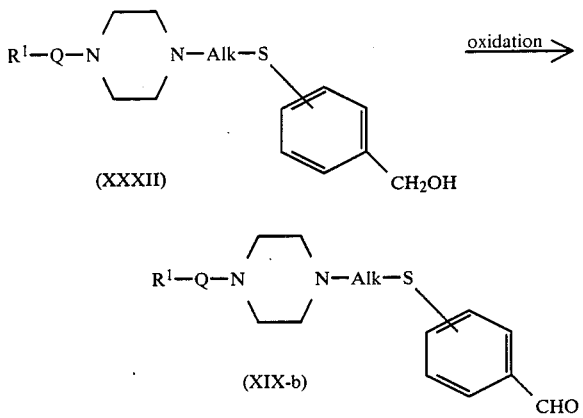

wherein $R^1$, Q and Alk are the same as defined above.

The oxidation may be carried out under the same conditions as described in Preparation 7.

The practical embodiments of the above-mentioned reaction are as follows:

A solution of 1.1 g of dimethylsulfoxide in 5 ml of methylene chloride is added to a solution of 0.894 g of oxalyl chloride in 20 ml of methylene chloride at −50° C. A solution of 2.19 g of 2-[3-(4-phenylpiperazin-1-yl)propylthio]benzylalcohol in 10 ml of methylene chloride is added to the mixture at −50° C., and the mixture is stirred at the same temperature for 15 minutes. 3.24 g of triethylamine are added to the mixture, and the mixture is stirred at −50° C. for 5 minutes and further stirred at room temperature for one hour. The mixture is poured into water, and the aqueous mixture is extracted with methylene chloride. The extract is washed with water, dried and concentrated under reduced pressure to remove solvent. The residue is purified by silica gel chromatography (solvent, ethyl acetate:chloroform=1:6). 1.97 g of 2-[3-(4-phenylpiperazin-1-yl)propylthio]benzaldehyde are obtained as an oil. Yield: 90.5%.

IR$\nu_{max}^{liq}$ (cm$^{-1}$): 2800, 1680, 1600, 1230, 750.

6.0 g of 2-[2-(4-phenylpiperazin-1-yl)ethylthio]benzylalcohol, 2.60 g of oxalyl chloride, 3.2 g of dimethylsulfoxide and 9.3 g of triethylamine are treated in the same manner as described above. 5.55 g of 2-[2-(4-phenylpiperazin-1-yl)ethylthio]benzaldehyde are obtained. Yield: 93%.

M.p. 73°–76° C.

Preparation 15

2.21 g of sodium hydroxide are added to a solution of 5.75 g of cysteamine hydrochloride in 200 ml of ethanol, and a solution of 14.28 g of 2-[2-(4-phenylpiperazin-1-yl)ethyloxy]benzaldehyde in 100 ml of ethanol is added thereto. After the mixture is stirred at room temperature for 2 hours, the mixture is concentrated under reduced pressure to remove solvent. The residue is dissolved in ethyl acetate, and the solution is washed with water, dried and then concentrated under reduced pressure to remove solvent. The residue is recrystallized from ether. 15.54 g of 2-{2-[2-(4-phenylpiperazin-1-yl)ethyloxy]phenyl}thiazolidine are obtained.

Yield: 91.4%.

M.p. 77°-86° C.

The following compounds are obtained from the corresponding starting compounds in the same manner as described above.

TABLE 20

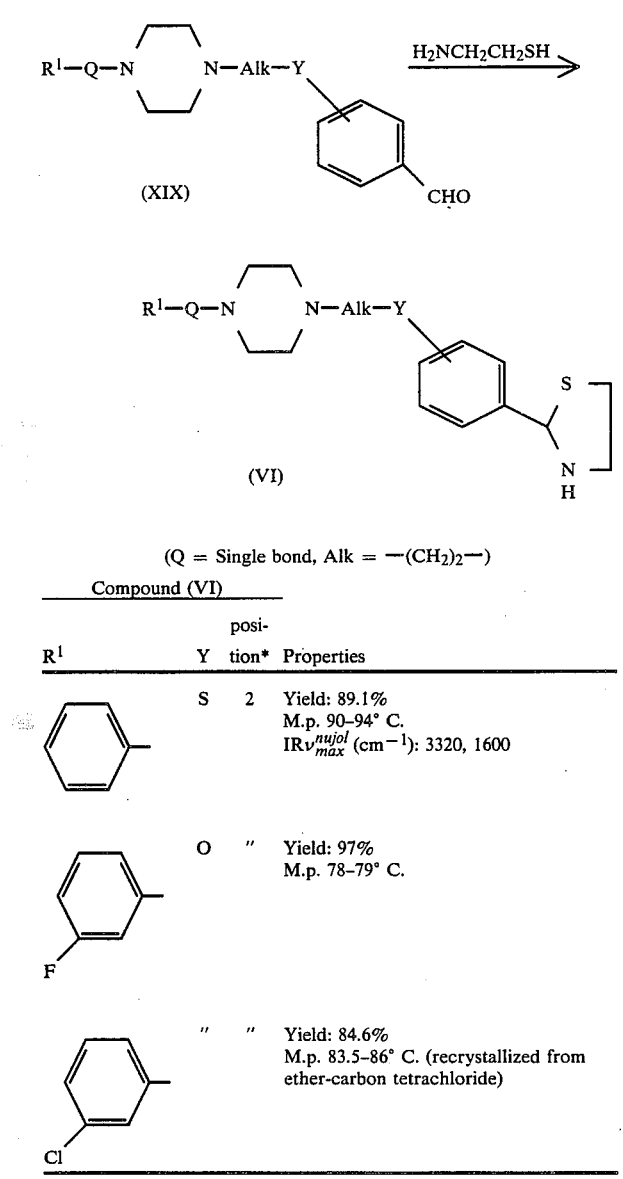

(Q = Single bond, Alk = —(CH₂)₂—)

*Position means the position of the R¹—Q—N N—Alk—Y— group which is substituted on the benzene ring (the carbon atom of benzene ring which carries a thiazolidine group is taken as the 1-position).

What we claim is:

1. A thiazolidine compound of the formula:

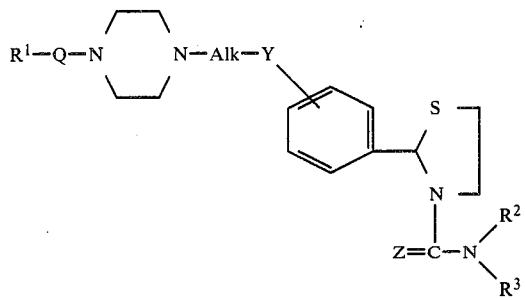

wherein R¹ is a phenyl group which is unsubstituted or substituted with one substituent selected from the group consisting of halogen atom, an alkyl group having one to 5 carbon atoms, an alkylthio group having one to 5 carbon atoms and an alkoxy group having one to 5 carbon atoms; Q is a single bond, an alkylene group having one to 5 carbon atoms or an alkenylene group having 2 to 6 carbon atoms; R² and R³ are the same or different and each is a hydrogen atom, an alkyl group having one to 5 carbon atoms, a cycloalkyl group having 3 to 7 carbon atoms, an alkanoyl group having 2 to 6 carbon atoms, an alkoxycarbonyl group having 2 to 6 carbon atoms, an alkylsulfonyl group having one to 5 carbon atoms, a benzoyl group, a phenyl group or a di(alkyl)-phosphoryl group having 2 to 6 carbon atoms; Alk is an alkylene group having one to 5 carbon atoms; and Y and Z are the same or different and each is an oxygen atom or sulfur atom, or a pharmaceutically acceptable salt thereof.

2. A thiazolidine compound of the formula:

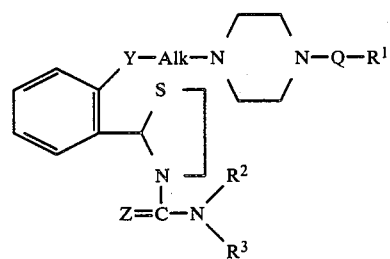

wherein R¹ is a phenyl group which is unsubstituted or substituted with one substituent selected from the group consisting of a halogen atom, an alkyl group having one to 5 carbon atoms, an alkylthio group having one to 5 carbon atoms and an alkoxy group having one to 5 carbon atoms; Q is a single bond, an alkylene group having one to 5 carbon atoms or an alkenylene group having 2 to 6 carbon atoms; R² and R³ are the same or different and each is a hydrogen atom, an alkyl group having one to 5 carbon atoms, a cycloalkyl group having 3 to 7 carbon atoms, an alkanoyl group having 2 to 6 carbon atoms, an alkoxycarbonyl group having 2 to 6 carbon atoms, an alkylsulfonyl group having one to 5 carbon atoms, a benzoyl group, a phenyl group or a di(alkyl)-phosphoryl group having 2 to 6 carbon atoms; Alk is an alkylene group having one to 5 carbon atoms; and Y and Z are the same or different and each is an oxygen atom or sulfur atom, or a pharmaceutically acceptable salt thereof.

3. The compound claimed in claim 1, in which R¹ is phenyl which is unsubstituted or substituted with one subtituent selected from the group consisting of fluorine, chlorine, alkyl having one to 3 carbon atoms, alkoxy having one to 3 carbon atoms, alkylthio having one to 3 carbon atoms and nitro; Q is a single bond, alkylene having one to 3 carbon atoms or propenylene, Alk is alkylene having 2 to 5 carbon atoms; and R² is hydrogen atom, alkyl having one to 4 carbon atoms, cycloalkyl having 4 to 6 carbon atoms, alkanoyl having 2 to 5 carbon atoms, alkoxycarbonyl having 2 to 4 carbon atoms, benzoyl, phenyl or di(alkyl)phosphoryl having 2 to 6 carbon atoms and R³ is hydrogen atom or alkyl having one to 4 carbon atoms; or R² is alkyl having one to 4 carbon atoms and R³ is alkanoyl having 2 to 5 carbon atoms or benzoyl.

4. The compound claimed in claim 3, in which R¹ is phenyl, fluorophenyl or methylphenyl, Q is a single bond, Alk is ethylene, R² is hydrogen atom or methyl and R³ is hydrogen atom, methyl or acetyl.

5. The compound claimed in claim 2, in which R¹ is phenyl which is unsubstituted or substituted with one substituent selected from the group consisting of chlorine, fluorine, alkyl having one to 3 carbon atoms, alkoxy having one to 3 carbon atoms, alkylthio having one to 3 carbon atoms and nitro; Q is a single bond, alkylene having one to 3 carbon atoms or propenylene; Alk is alkylene having 2 to 5 carbon atoms; and R² is hydrogen atom, alkyl having one to 4 carbon atoms, cycloalkyl having 4 to 6 carbon atoms, alkanoyl having 2 to 5 carbon atoms, alkoxycarbonyl having 2 to 4 carbon atoms, benzoyl, phenyl or di(alkyl)phosphoryl having 2 to 6 carbon atoms and R³ is hydrogen atom or alkyl having one to 4 carbon atoms; or R² is alkyl having one to 4 carbon atoms and R³ is alkanoyl having 2 to 5 carbon atoms or benzoyl.

6. The compound claimed in claim 5, in which R¹ is phenyl, fluorophenyl, chlorophenyl, methylphenyl or methoxyphenyl; Q is a single bond; Alk is ethylene or trimethylene; R² is hydrogen atom or alkyl having one to 3 carbon atoms and R³ is hydrogen atom, alkyl having one to 3 carbon atoms or alkanoyl having 2 to 4 carbon atoms.

7. The compound claimed in claim 5, in which R¹ is phenyl, fluorophenyl or methylphenyl, Q is a single bond, Alk is ethylene, R² is hydrogen atom or methyl and R³ is hydrogen atom, methyl or acetyl.

8. The compound claimed in claim 7, in which Y is oxygen atom and Z is oxygen atom or sulfur atom.

9. The compound claimed in claim 7, in which R¹ is phenyl or fluorophenyl, R² is methyl, R³ is hydrogen atom or acetyl and Y and Z are oxygen atom.

10. The compound in claim 8 which is N-methyl-2-{2-[2-(4-phenylpiperazin-1-yl)ethyloxy]phenyl}thiazolidine-3-carbothioamide or a pharmaceutically acceptable salt thereof.

11. The compound claimed in claim 8 which is N-methyl-2-{2-[2-(4-(2-fluorophenyl)piperazin-1-yl)ethyloxy]phenyl}thiazolidine-3-carbothioamide or a pharmaceutically acceptable salt thereof.

12. The compound claimed in claim 9 which is N-methyl-2-{2-[2-(4-phenylpiperazin-1-yl)ethyloxy]phenyl}thiazolidine-3-carboxamide or a pharmaceutically acceptable salt thereof.

13. The compound claimed in claim 9 which is (−)-N-methyl-2-{2-[2-(4-phenylpiperazin-1-yl)ethyloxy]phenyl}thiazolidine-3-carboxamide or a pharmaceutically acceptable salt thereof.

14. The compound claimed in claim 9 which is (+)-N-methyl-2-{2-[2-(4-phenylpiperazine-1-yl)ethyloxy]phenyl}thiazolidine-3-carboxamide or a pharmaceutically acceptable salt thereof.

15. The compound cliamed in claim 9 which is N-acetyl-N-methyl-2-{2-[2-(4-(3-fluorophenyl)piperazine-1-yl)ethyloxy]phenyl}thiazolidine-3-carboxamide or a pharmaceutically acceptable salt thereof.

16. A pharmaceutical composition exhibiting a cardiotonic effect which comprises a therapeutically effective amount of a thiazolidine compound of the formula:

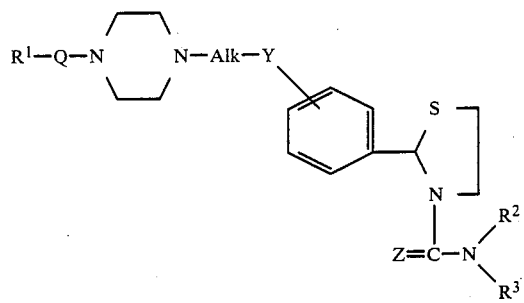

wherein R¹ is a phenyl group which is unsubstituted or substituted with one substituent selected from the group consisting of a halogen atom, an alkyl group having one to 5 carbon atoms, an alkylthio group having one to 5 carbon atoms and an alkoxy group having one to 5 carbon atoms; Q is a single bond, an alkylene group having one to 5 carbon atoms or an alkenylene group having 2 to 6 carbon atoms; R² and R³ are the same or different and each is a hydrogen atom, an alkyl group having one to 5 carbon atoms, a cycloalkyl group having 3 to 7 carbon atoms, an alkanoyl group having 2 to 6 carbon atoms, an alkoxycarbonyl group having 2 to 6 carbon atoms, an alkylsulfonyl group having one to 5 carbon atoms, a benzoyl group, a phenyl group or a di(alkyl)-phosphoryl group having 2 to 6 carbon atoms; Alk is an alkylene group having one to 5 carbon atoms; and Y and Z are the same or different and each is an oxygen atom or sulfur atom, or a pharmaceutically acceptable salt thereof, and a pharmaceutically acceptable carrier therefor.

17. A method of producing a cardiotonic effect on a warm-blooded animal comprising administering to said warm-blooded animal an effective amount of a thiazolidine compound of the formula:

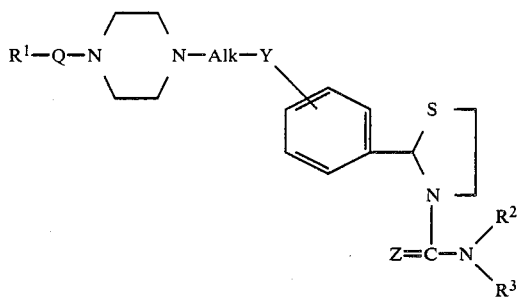

wherein R¹ is a phenyl group which is unsubstituted or substituted with one substituent selected from the group consisting of a halogen atom, an alkyl group having one to 5 carbon atoms, an alkylthio group having one to 5 carbon atoms and an alkoxy group having one to 5 carbon atoms; Q is a single bond, an alkylene group having one to 5 carbon atoms or an alkenylene group having 2 to 6 carbon atoms; R² and R³ are the same or different and each is a hydrogen atom, an alkyl group having one to 5 carbon atoms, a cycloalkyl group having 3 to 7 carbon atoms, an alkanoyl group having 2 to 6 carbon atoms, an alkoxycarbonyl group having 2 to 6 carbon atoms, an alkylsulfonyl group having one to 5 carbon atoms, a benzoyl group, a phenyl group or a di(alkyl)-phosphoryl group having 2 to 6 carbon atoms; Alk is an alkylene group having one to 5 carbon atoms; and Y and Z are the same or different and each is an oxygen atom or sulfur atom, or a pharmaceutically acceptable salt thereof.

18. A method according to claim 17 wherein the effective amount is in a range of 0.001 to 10 mg/kg/day.

* * * * *